(12) United States Patent
Noble et al.

(10) Patent No.: US 11,872,398 B2
(45) Date of Patent: *Jan. 16, 2024

(54) PATIENT-CUSTOMIZED ELECTRODE ARRAYS BASED ON PATIENT-SPECIFIC COCHLEAR INFORMATION, AND DESIGNING/SELECTING METHODS AND APPLICATIONS OF SAME

(71) Applicant: VANDERBILT UNIVERSITY, Nashville, TN (US)

(72) Inventors: Jack H. Noble, Nashville, TN (US); Robert F. Labadie, Nashville, TN (US); Benoit M. Dawant, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/340,303

(22) Filed: Jun. 7, 2021

(65) Prior Publication Data
US 2021/0361944 A1 Nov. 25, 2021

Related U.S. Application Data

(63) Continuation of application No. 16/607,507, filed as application No. PCT/US2018/029037 on Apr. 24, 2018, now Pat. No. 11,027,129.
(Continued)

(51) Int. Cl.
*A61N 1/36* (2006.01)
*A61B 34/10* (2016.01)
(Continued)

(52) U.S. Cl.
CPC .......... *A61N 1/36039* (2017.08); *A61B 5/055* (2013.01); *A61B 5/1076* (2013.01);
(Continued)

(58) Field of Classification Search
CPC ........ A61B 2034/105; A61B 2034/107; A61B 2034/108; A61B 2034/2055;
(Continued)

(56) References Cited

U.S. PATENT DOCUMENTS

2012/0071890 A1* 3/2012 Taylor .................. A61B 5/6817
606/129

* cited by examiner

*Primary Examiner* — Manuchehr Rahmjoo
(74) *Attorney, Agent, or Firm* — Locke Lord LLP; Tim Tingkang Xia, Esq.

(57) ABSTRACT

A method for designing a patient-customized EA or selecting an existing EA that fits the patient best includes segmenting shapes of SOIs of the cochlea in a pre-operative CT image using a shape model; defining a 3D curve of interest within the shape model of the SOIs as a sequence of points-; automatically transforming the defined 3D curve to the pre-operative CT image so as to obtain a structure curve in the cochlea; determining a length and curvatures of the structure curve at the sequence of points; and designing a patient-customized EA or selecting an existing EA based on the determined length and curvatures of the structure curve such that after the EA shape model, which estimates the resting state shape of the EA, is rigidly registered to the structure curve in the cochlea, the EA shape model has a registration error smaller than a preset value.

14 Claims, 26 Drawing Sheets

Related U.S. Application Data

(60) Provisional application No. 62/540,669, filed on Aug. 3, 2017, provisional application No. 62/489,005, filed on Apr. 24, 2017.

(51) Int. Cl.

| | | |
|---|---|---|
| *A61B 5/055* | (2006.01) | |
| *A61B 5/107* | (2006.01) | |
| *A61N 1/05* | (2006.01) | |
| *G06T 7/181* | (2017.01) | |
| *G06T 7/12* | (2017.01) | |
| *G06T 11/00* | (2006.01) | |
| *A61B 6/03* | (2006.01) | |

(52) U.S. Cl.
CPC ............ *A61B 34/10* (2016.02); *A61N 1/0541* (2013.01); *G06T 7/12* (2017.01); *G06T 7/181* (2017.01); *G06T 11/005* (2013.01); *A61B 6/032* (2013.01); *A61B 2034/105* (2016.02); *A61B 2034/107* (2016.02); *A61B 2034/108* (2016.02); *A61B 2505/05* (2013.01); *A61B 2562/043* (2013.01); *G06T 2207/30008* (2013.01); *G06T 2211/424* (2013.01)

(58) Field of Classification Search
CPC .......... A61B 2505/05; A61B 2562/043; A61B 34/10; A61B 5/055; A61B 5/1072; A61B 5/1076; A61B 5/686; A61B 6/03; A61B 6/032; A61B 6/12; A61B 6/5217; A61N 1/0541; A61N 1/36036; A61N 1/36039; A61N 1/37518; G06T 11/005; G06T 2207/30008; G06T 2211/424; G06T 7/12; G06T 7/181; G16H 20/40; G16H 50/50
See application file for complete search history.

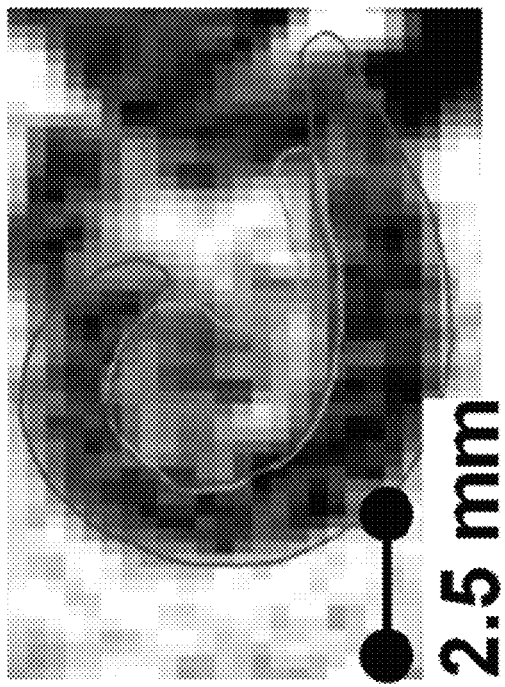
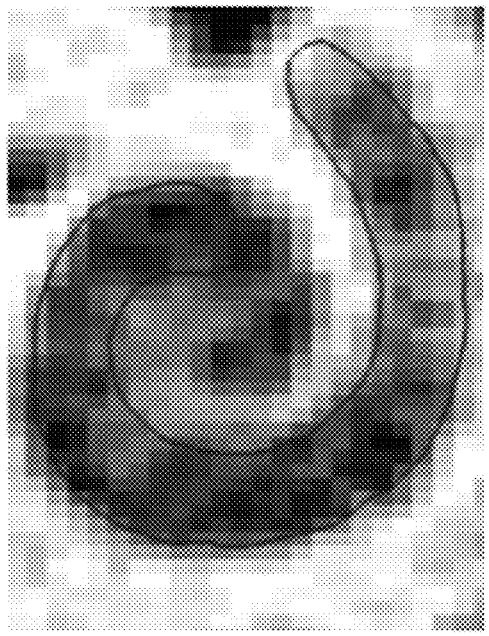
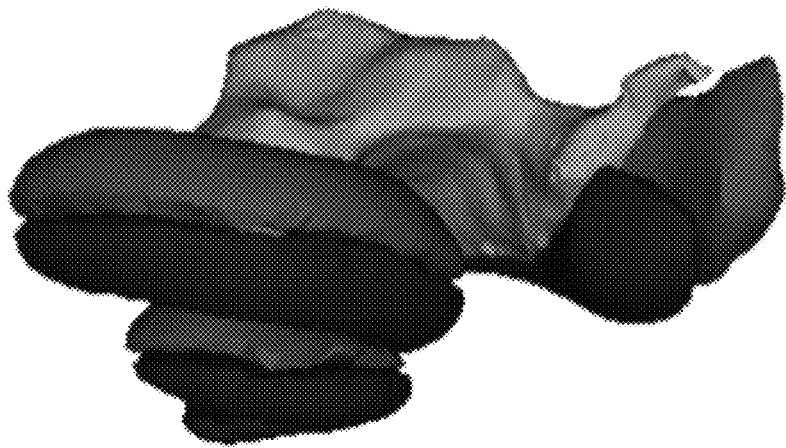
FIG. 3B
FIG. 3C
FIG. 3A

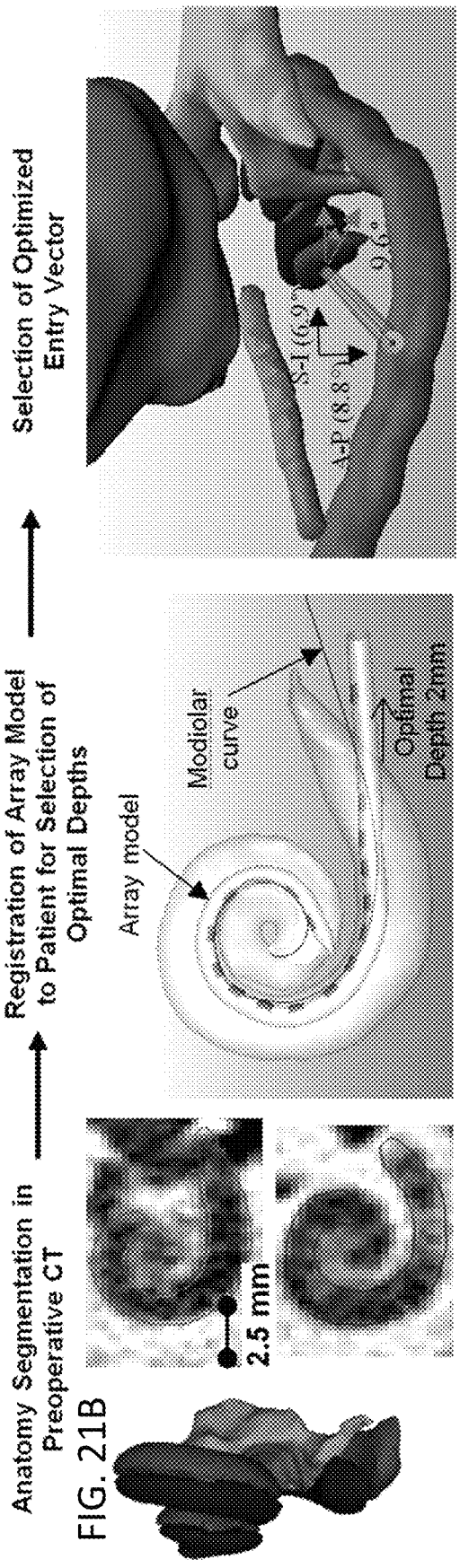

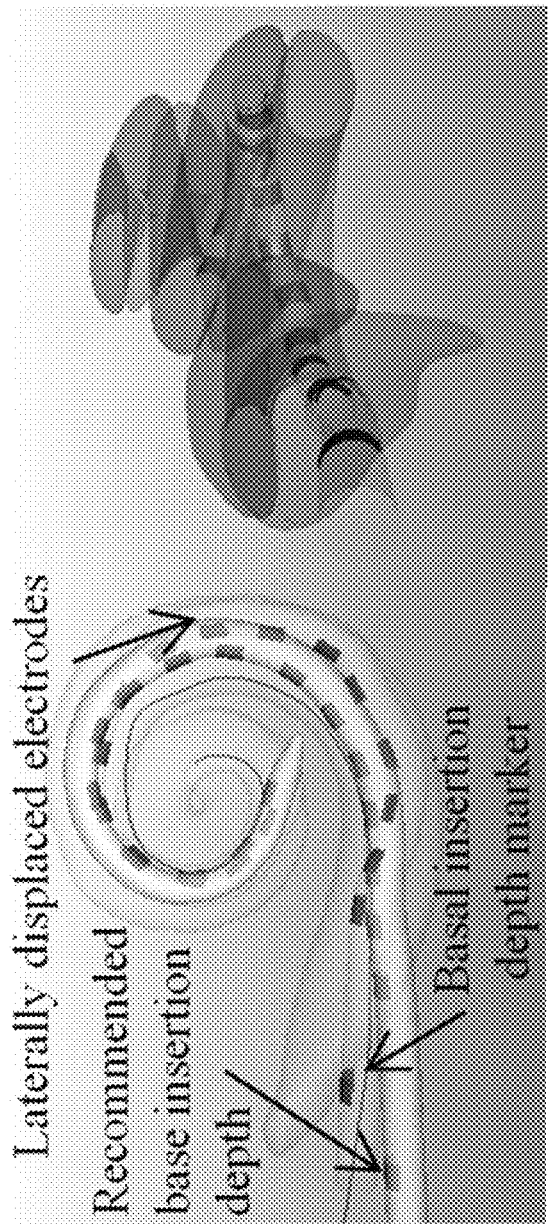
FIG. 22A
FIG. 22B
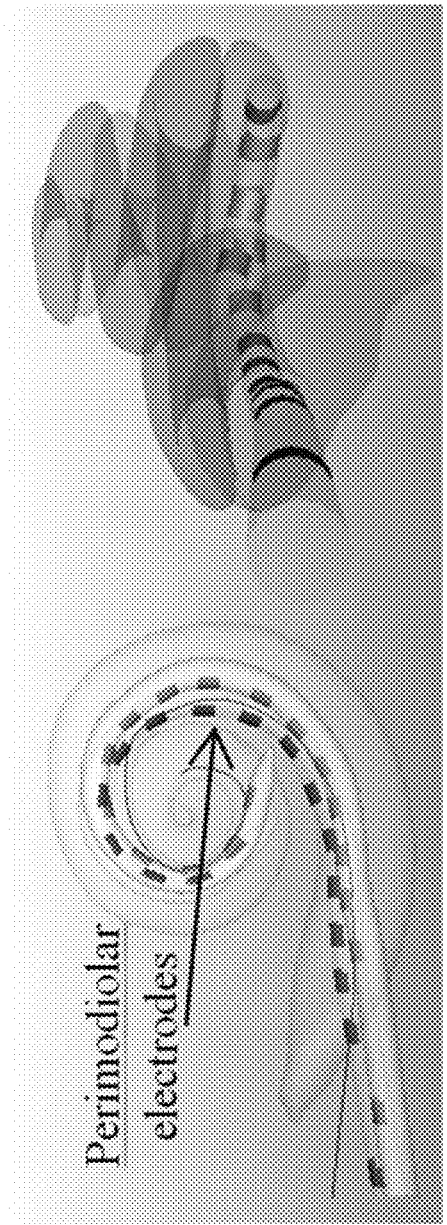
FIG. 22C
FIG. 22D

PATIENT-CUSTOMIZED ELECTRODE ARRAYS BASED ON PATIENT-SPECIFIC COCHLEAR INFORMATION, AND DESIGNING/SELECTING METHODS AND APPLICATIONS OF SAME

CROSS-REFERENCE TO RELATED PATENT APPLICATIONS

This application is a continuation application of U.S. patent application Ser. No. 16/607,507, filed Oct. 23, 2019, now allowed, which is a national stage entry of PCT Application Serial No. PCT/US2018/029037, filed Apr. 24, 2018, which itself claims priority to and the benefit of, pursuant to 35 U.S.C. § 119(e), U.S. Provisional Patent Application Serial Nos. 62/489,005, filed Apr. 24, 2017, and 62/540,669 filed Aug. 3, 2017, which are incorporated herein in their entireties by reference.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [12] represents the 12th reference cited in the reference list, namely, Noble, J. H., Gifford, R. H., Labadie, R. F., Dawant, B. M., 2012, "Statistical Shape Model Segmentation and Frequency Mapping of Cochlear Implant Stimulation Targets in CT," N. Ayache et al. (Eds.): MICCAI 2012, Part II, LNCS 7511, pp. 421-428. 2012.

STATEMENT AS TO RIGHTS UNDER FEDERALLY-SPONSORED RESEARCH

This invention was made with government support under Contract No. R01DC008408 and R01DC014462 awarded by the National Institute on Deafness and Other Communication Disorders (NIDCD). The government has certain rights in the invention.

FIELD OF THE INVENTION

The invention relates generally to cochlear implants, and more particularly, to patient-customized electrode arrays, and methods for designing a patient-customized electrode array (EA) or selecting an existing EA that fits the patient best, based on patient-specific cochlear information, and applications of same.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Cochlear implants (CIs) are considered standard of care treatment for severe-to-profound sensory-based hearing loss [1]. Cochlear and Advanced Bionics, two of the three FDA approved CI manufacturers, report having sold over 400K and over 100K CIs worldwide, respectively. CIs restore hearing by applying electric potential to neural stimulation sites in the cochlea with a surgically implanted electrode array. Implants available today produce remarkable results for the vast majority of recipients with average postoperative word and sentence recognition approximating 60% and 70% correct, respectively, for unilaterally implanted recipients and 70% and 80% correct for bilateral recipients [2-6]. Despite this success, a significant number of users receive marginal benefit, and restoration to normal fidelity is rare even among the best performers. Research by many groups over the last few decades has shown that atraumatic placement and proper positioning of the array within the cochlea are crucial for maximizing post-implantation hearing performance and speech recognition [7-10]. Despite the overwhelming evidence that sub-optimal array placement is linked with poorer outcomes, few technologies have been introduced in the past few decades that improve the surgical placement of the array with most focused on electrode array design and generic insertion guidelines applied to entire populations rather than individuals, despite the fact that no single array design could lead to optimal placement for most individuals due to the large inter-patient variations in the size and shape of the cochlea that have been well documented [13-14]. With today's technology, optimal placement of arrays remains the exception, rather than the norm, and average speech recognition scores with CIs are approximately the same as those achieved in the 1990's.

The use of patient-specific information to optimize placement has received relatively minimal attention, and no patient-specific approaches are in widespread use today. One factor that has limited development in this area is that it has been difficult to measure patient-specific differences cochlear anatomy because the cochlea is difficult to image. Although the computed tomography (CT) is the clinical modality that affords the highest clinical resolution, intracochlear structures are so small that they are not visible in CT images. This technological barrier has prevented precise and accurate quantification of patient-specific cochlear anatomy. In addition to lack of precision, procedures available have been labor intensive, posing a barrier for clinical adoption of patient-specific analyses.

Therefore, a heretofore unaddressed need exists in the art to address the aforementioned deficiencies and inadequacies.

SUMMARY OF THE INVENTION

One of the objectives of the invention is to design a patient-customized electrode array (EA) or select an existing EA that fits the patient best, based on information of the patient-specific cochlea size and/or shape.

In one aspect, the present invention relates to a method for designing a patient-customized EA or selecting an existing EA that fits the patient best, based on information of the patient-specific cochlea size and/or shape. In one embodiment, the method comprises segmenting shapes of structures of interest (SOIs) of a cochlea of the patient in a pre-operative CT image of the cochlea using a shape model, wherein the EA is to be placed in the cochlea; defining a 3D curve of interest within the shape model of the SOIs as a sequence of points, $\{P_i\}$, wherein i=1, 2, 3, . . . N, N is an integer greater than zero; automatically transforming the defined 3D curve to the pre-operative CT image so as to obtain a structure curve in the cochlea; determining a length and curvatures of the structure curve at the sequence of points $\{P_i\}$, and designing a patient-customized EA or selecting an existing EA based on the determined length and curvatures of the structure curve such that after the EA shape model, which estimates the resting state shape of the EA, is rigidly registered to the structure curve in the cochlea, the EA shape model has a registration error smaller than a preset value.

In one embodiment, the method further comprises determining a patient-customized insertion plan for electrode insertion using the registered EA shape model, wherein the patient-customized insertion plan comprises at least a recommended depth.

In one embodiment, when inserted, the base depth of electrode insertion of the EA matches the recommended depth.

In one embodiment, the EA comprises a plurality of electrodes, $\{E_i\}$, wherein the i-th electrode $E_i$ is to be placed in a location corresponding to the i-th point $P_i$ of the structure curve in the cochlea, wherein i=1, 2, 3, . . . N, N is an integer greater than zero.

In one embodiment, the curvature of the EA at the i-th electrode $E_i$ is characterized with a curvature $R_i$ that matches the curvature of the i-th point Pi of the structure curve in the cochlea.

In one embodiment, the i-th electrode $E_i$ is a flat electrode, or a curved electrode that is characterized with a curvature that matches the curvature of the i-th point $P_i$ of the structure curve in the cochlea.

In one embodiment, the structure curve is a modiolar curve in the cochlea, and wherein the EA is a pre-curved EA.

In one embodiment, the structure curve is a lateral wall curve in the cochlea, and wherein the EA is a straight EA. In one embodiment, the straight EA has a length determined such that when placed along the lateral wall curve, an angular insertion depth of the distal electrode reaches about 500°, while a proximal electrode falls safely within the cochlea being greater than 30°.

In one embodiment, the SOIs are temporal bone anatomy. In one embodiment, the SOIs are intra-cochlear structures.

In one embodiment, the shape model is a non-rigid statistical shape model created with μCT images of a plurality of cochlea specimens in which intra-cochlear structures are visible.

In one embodiment, the defined 3D structure curve is automatically transformed to the pre-operative CT image using a thin plate spline registration.

In one embodiment, the EA shape model is rigidly registered to the structure curve in the cochlea using an iterative closest point registration, thereby placing the resting state shape of the EA within the SOIs in the cochlea such that the EA matches the structure curve in the cochlea.

In one embodiment, the segmenting step comprises automatically fitting the shape model to an external boundary of the cochlea that is visible in the pre-operative CT, thereby allowing highly accurate estimation of positions and shapes of intra-cochlear structures of the cochlea that are not visible in the pre-operative CT.

In another aspect, the present invention relates to a non-transitory computer-readable medium storing instructions which, when executed by a processor, cause a computer or system to perform a method for designing a patient-customized electrode array (EA) or selecting an existing EA that fits the patient best, based on information about the patient-specific cochlea size and/or shape.

In one embodiment, the method includes segmenting shapes of SOIs of a cochlea of the patient in a pre-operative CT image of the cochlea using a shape model, wherein the EA is to be placed in the cochlea; defining a 3D curve of interest within the shape model of the SOIs as a sequence of points, $\{P_i\}$, wherein i=1, 2, 3, . . . N, N is an integer greater than zero; automatically transforming the defined 3D curve to the pre-operative CT image so as to obtain a structure curve in the cochlea; determining a length and curvatures of the structure curve at the sequence of points $\{P_i\}$, and designing a patient-customized EA or selecting an existing EA based on the determined length and curvatures of the structure curve such that after the EA shape mode, which estimates the resting state shape of the EA,1 is rigidly registered to the structure curve in the cochlea, the EA shape model has a registration error smaller than a preset value.

In one embodiment, the method further comprises determining a patient-customized insertion plan for electrode insertion using the registered EA shape model, wherein the patient-customized insertion plan comprises at least a recommended depth.

In one embodiment, when inserted, the base depth of electrode insertion of the EA matches the recommended depth.

In one embodiment, the EA comprises a plurality of electrodes, $\{E_i\}$, wherein the i-th electrode $E_i$ is to be placed in a location corresponding to the i-th point $P_i$ of the structure curve in the cochlea, wherein i=1, 2, 3, . . . N, N is an integer greater than zero.

In one embodiment, the curvature of the EA at the i-th electrode Ei is characterized with a curvature that matches the curvature of the i-th point $P_i$ of the structure curve in the cochlea.

In one embodiment, the i-th electrode $E_i$ is a flat electrode, or a curved electrode that is characterized with a curvature that matches the curvature of the i-th point $P_i$ of the structure curve in the cochlea.

In one embodiment, the structure curve is a modiolar curve in the cochlea, and wherein the EA is a pre-curved EA.

In one embodiment, the structure curve is a lateral wall curve in the cochlea, and wherein the EA is a straight EA. In one embodiment, the straight EA has a length determined such that when placed along the lateral wall curve, an angular insertion depth of the distal electrode reaches about 500°, while a proximal electrode falls safely within the cochlea being greater than 30°.

In one embodiment, the SOIs are temporal bone anatomy.

In one embodiment, the shape model is created with μCT images of a plurality of cochlea specimens in which intra-cochlear structures are visible.

In one embodiment, the defined 3D structure curve is automatically transformed to the pre-operative CT image using a thin plate spline registration.

In one embodiment, the EA shape model is rigidly registered to the structure curve in the cochlea using an iterative closest point registration, thereby placing the resting state shape of the EA within the SOIs in the cochlea such that the EA matches the structure curve in the cochlea.

In one embodiment, the segmenting step comprises automatically fitting the shape model to an external boundary of the cochlea that is visible in the pre-operative CT, thereby allowing highly accurate estimation of positions and shapes of intra-cochlear structures of the cochlea that are not visible in the pre-operative CT.

In yet another aspect, the present invention relates to a method for designing a patient-customized EA or selecting an existing EA that fits the patient best, based on information of the patient-specific cochlea size and/or shape. In one embodiment, the method includes acquiring information of the patient-specific cochlear size and/or shape of the cochlea; and selecting/designing the patient-customized EA based on the acquired information of the patient-specific cochlear size and/or shape of the cochlea.

In one embodiment, the acquiring step comprises segmenting shapes of SOIs of a cochlea of the patient in a pre-operative CT image of the cochlea using a shape model, wherein the EA is to be placed in the cochlea; defining a 3D curve of interest within the shape model of the SOIs as a sequence of points, $\{P_i\}$, wherein i=1, 2, 3, ... N, N is an integer greater than zero; automatically transforming the defined 3D curve to the pre-operative CT image so as to obtain a structure curve in the cochlea; and determining a length and curvatures of the structure curve at the sequence of points $\{P_i\}$.

In one embodiment, the selecting/designing step comprises designing a patient-customized EA or selecting an existing EA based on the determined length and curvatures of the structure curve in cochlea such that after the EA shape model, which estimates the resting state shape of the EA, is rigidly registered to the structure curve in the cochlea, the EA shape model has a registration error smaller than a preset value.

In one embodiment, the SOIs are a temporal bone anatomy or a lateral wall in the cochlea.

In one embodiment, the structure curve is a modiolar curve or a lateral wall curve in the cochlea.

In one aspect, the present invention relates to a patient-customized EA. In one embodiment, the patient-customized EA has a plurality of electrodes, $\{E_i\}$, assembled in a pre-curved form, wherein the curvature of the EA at the i-th electrode $E_i$ is characterized with a curvature that matches the curvature of the i-th point $P_i$ of the structure curve in the cochlea of a patient where the i-th electrode $E_i$ is to be placed, wherein i=1, 2, 3, ... N, N is an integer greater than zero.

In one embodiment, the structure curve is a modiolar curve in the cochlea.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

FIG. 1B is a rendering of the auditory nerve bundles of the SG in green. FIGS. 1C-1D are a surface representing the modiolar wall interface between the nerves of the SG and the intra-cochlear cavities is color coded with the tonotopic place frequencies of the SG in Hz. FIG. 1D also shows the implanted electrodes of an Advanced Bionics CI, numbered 1-16. An illustration of broad overlapping excitation patterns from each electrode is rendered transparently with varying colors across electrodes. Similar results can be generated with the 12 electrode MED-EL CI and the 22 electrode Cochlear CI.

FIG. 3A shows automatically segmented surfaces of the scala tympani (red), scala vestibuli (blue), and modiolus (green) of a cochlea, according to one embodiment of the present invention. FIGS. 3B-3C show a corresponding pre-operative CT image with superimposed structure contours.

FIGS. 9A and 9C are posterior-to-anterior views, and FIGS. 9B and 9D are lateral-to-medial views.

FIGS. 11A-11B and 11D-11E are posterior-to-anterior views, and FIGS. 11C and 11F are medial-to-lateral views.

FIG. 13A shows Cochlear® lateral wall electrode with axial orientation wing (solid white arrow) and depth markers (dotted arrows). FIG. 13A shows a surgical forceps with tool reference frame (red arrow) complete with optical tracking spheres and FIG. 13A shows an infrared optical tracker (NDI Polaris Krios; Waterloo, Ontario).

In FIG. 15C, red is ST and blue is SV.

FIGS. 21A-21E show three steps in the proposed image-guided insertion planning process, according to one embodiment of the present invention. FIG. 21A shows automatically segmented surfaces of the scala tympani (red), scala vestibuli (blue), and modiolus (green).

FIGS. 21B-21B are slices in the corresponding pre-operative CT scan with superimposed structure contours. FIG. 21D shows the array model (contacts in green) registered to the modiolar curve (blue) of the patient's scala tympani (white), as well as the overall insertion depth recommended based on this registered model. FIG. 21D shows the view down the control trajectory (green circle) implemented for case No. 12 relative to the facial nerve (magenta), chorda tympani (green), ossicles (aqua), and external auditory canal (yellow). The optimal trajectory, which is collinear with the basal turn, is shown as the yellow cylinder. The angle of the control trajectory relative to the optimal trajectory is shown for the S-I and A-P directions. The angle between the control and optimal electrode orientation is also shown.

FIGS. 22A-22D show the modiolar curve (blue), registered model array (green), and actual final electrode position (red) for case No. 3 in FIG. 22A and No. 18 in FIG. 22C noting that insertion to the generic insertion depth in (a) caused the electrode to become laterally displaced while the electrode in (c) has better perimodiolar position. A lateral-to-medial view of case No. 3 (FIG. 22B) and No. 18 (FIG. 22D) show full ST positioning in FIG. 22D and a scalar translocation in FIG. 22B.

DETAILED DESCRIPTION OF THE INVENTION

Figure 1B:
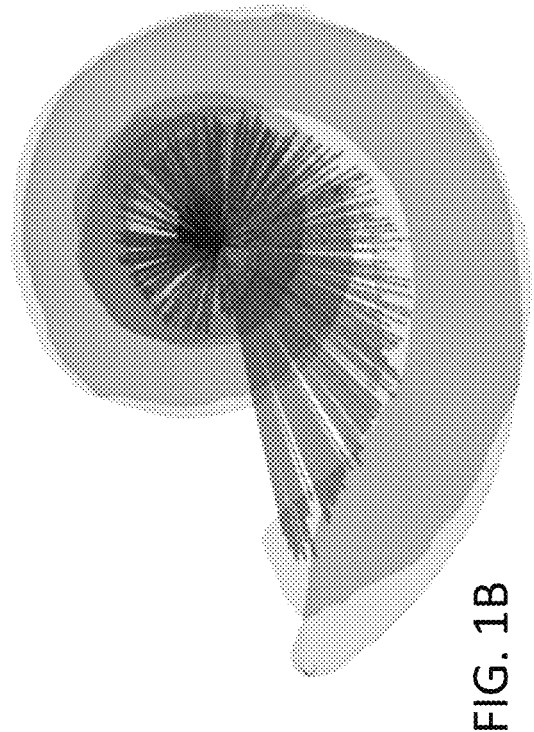
FIGS. 1A-1D show the scala tympani (ST) (red) and scala vestibule (SV) (blue), the two principal cavities of a cochlea.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the FIGS. is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to. As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the terms "electrode array", its acronym "EA" and "array" are exchangeable and refer to an array of electrodes of a cochlear implant (CI) to be placed in a cochlea of a patient.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Figure 1D:
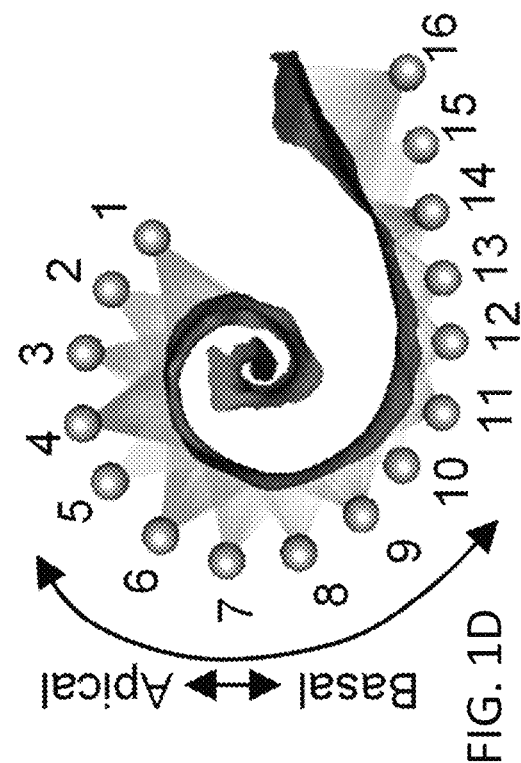
Figure 1A:
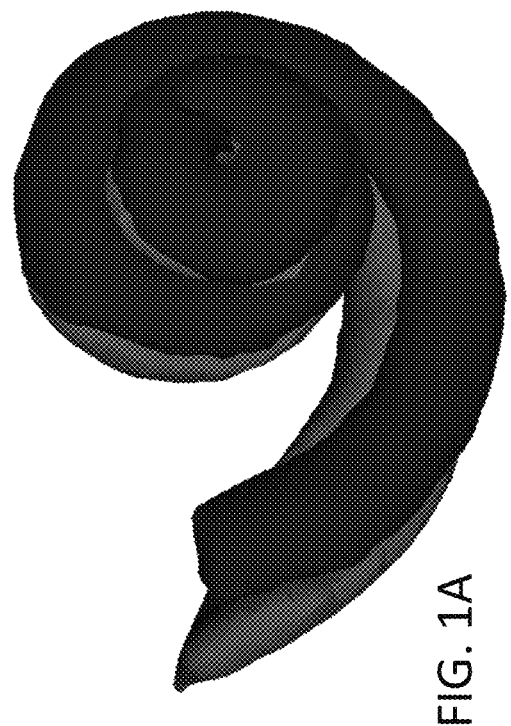

The CI uses an implanted electrode array (EA) to stimulate spiral ganglion (SG) neurons to induce hearing sensation (FIGS. 1A-1B). To date, the CI arguably has been the most successful neural prosthesis. During surgery, a surgeon performs a mastoidectomy, or removal of the bone behind the external ear, to gain access to the scala tympani (ST), one of the three intra-cochlear cavities and the one best-suited for placement of the EA. The EA is threaded into the ST at a tangential angle attempting to minimize stress on intracochlear tissue. The EA is threaded through either the round window (RW) by incising the membrane or via a separate cochleostomy site. The surgeon advances the EA until a depth marker on the EA reaches the entry site, which indicates the generically recommended insertion depth has been reached. As the interior of the cochlea is invisible to the surgeon, the intra-cochlear path of the EA and final positioning of the EA are generally unknown, yet retrospective studies show positioning to be a factor that significantly affects outcomes [8-10]. Advancements that permit improving placement have been incremental and have focused on design of EAs and surgical techniques that are generically applied to the entire population, despite the fact that no single array design is optimal for most individuals due to the large inter-patient variations in the size and shape of the cochlea that have been well studied [13-14]. Because of this, improvements to this technology have not led to significant improvement in speech recognition since the 1990's. Due to the small size of the electrodes (approximately $0.3 \times 0.3 \times 0.1$ $mm^3$) and their location within the dense bone surrounding the cochlea, the only techniques available for intra-operative imaging are x-ray-based modalities with known radiation risk. The magnet integrated in the CI precludes the use of MRI. It is thus not surprising that few methods that use patient-specific information to optimize placement for individuals have been introduced, and none are in widespread use. Our studies show that optimal placement of EAs is the exception rather than the norm. 60% word recognition is the CI population average [2-6] and would be the expected performance of an unaided individual experiencing severe hearing loss (HL) in the range of 71-80 dBHL [59]. Our data suggest that a CI recipient who achieves average word recognition and has average positioning of a pre-curved EA could have a very different outcome with relatively small changes to the position of the EA. With optimal positioning of the EA, this individual would be expected to achieve 79% word recognition, matching performance of an unaided listener with only moderate HL (51-60 dB). Conversely, the individual would be expected to achieve 39% word recognition with a sub-optimally positioned EA, corresponding to profound HL (>90 dBHL). As such, techniques for better positioning of the EA have significant quality-of-life and socioeconomic impact for CI recipients and society.

Figures 2A, 2B:
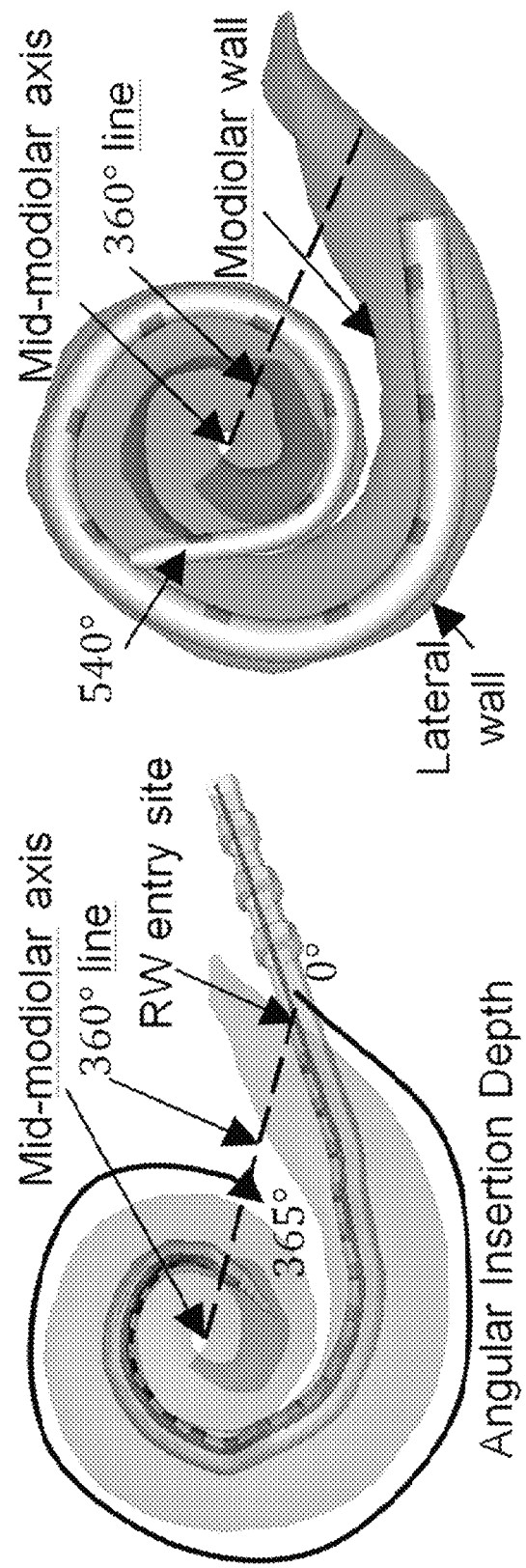
FIGS. 2A-2B show perimodiolar-positioned, pre-curved array placement and lateral wall-positioned, straight array placement, respectively, according to one embodiment of the present invention. Insertion depth of the array is measured in angle around the mid-modiolar axis to the most distal contact and is 365° on the perimodiolar-positioned, pre-curved array placement and 540° on the lateral wall-positioned, straight array placement.

The three FDA-approved CI manufacturers offer a range of device models which vary predominately in the intracochlear EA. For the vast majority of CI recipients, selection of the CI model and EA is based on surgeon and/or patient preference, and no data-driven approach exists for determining what device might lead to the best outcome for a specific patient. The various EAs differ in width, length, number of electrodes, electrode spacing, and shape. The shapes that are available can be broadly divided into two classes—straight and pre-curved EAs, as shown in FIGS. 2A-2B. A straight EA is designed such that its path within the cochlea is guided by the walls of the cochlea as it is threaded into the ST. The optimal positioning for a straight EA is along the outer (lateral) wall of the ST with the most apical electrode inserted to a depth of at least 500° [48]. Pre-curved EAs are designed such that the resting state shape of the EA roughly matches the coil of an average human cochlea. In practice, pre-curved EAs are loaded onto a straightening stylet. As the EA is threaded into the cochlea via advancing it off the stylet, the EA resumes its resting coiled shape; this technique is often referred to as advance-off-stylet (AOS). As shown in our preliminary results, optimal placement for pre-curved EAs is perimodiolar placement, i.e., the electrodes are positioned close to the inner (modiolar) wall, within the ST. This places the electrodes closer to the spiral ganglion cells that are stimulated by the electrodes to induce hearing sensation and is thought to provide both more discrete stimulation with less interference from neighboring electrodes and to use less energy. Clearly, the path of insertion and final positioning of the EA are highly dependent not only on the surgical technique and the selection of the EA model but also on the size and shape of the patient's cochlea, which are known to be highly variable across subjects [13-14]. The traditional one-size-fits-all approach does not consider the patient-specific anatomy when selecting the EA model or determining the surgical approach.

Figure 1C:
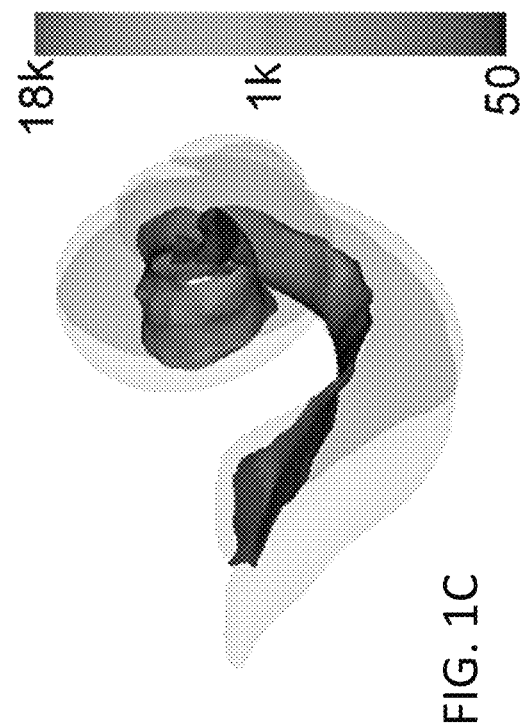

Only recently have large scale studies been done by the inventors and other groups to begin to better understand the relationship between outcomes and intra-cochlear EA positioning. Studying this has been problematic because it is difficult to determine the intra-cochlear location of the electrodes because the patient-specific shape of cochlear anatomy is challenging to image. Although CT is the clinical modality that affords the highest clinical resolution, intra-cochlear structures are so small that they are not visible in CT images. This technological barrier has prevented precise and accurate quantification of patient-specific cochlear anatomy. Further, procedures available have been highly labor intensive, making their use in large scale studies impractical. Research by the inventors has led to the development of automated image analysis algorithms that rely on a high-resolution micro-CT (µCT) atlas of cadaveric cochlear anatomy to identify patient-specific cochlear anatomy in the patient's clinical CT image with a high degree of accuracy [11-12]. Because these techniques are accurate and completely automated, they remove both the technical and labor barriers for determining patient-specific cochlea shape. Coupled with the use of automated methods the inventors have developed for accurately localizing EAs [15-16], these techniques facilitate measuring intra-cochlear CI electrode position of a large group of subjects. The studies of the inventors have confirmed several factors regarding the intra-cochlear positioning of the EA that affect outcomes. One factor is known as "channel interaction", which arises due to the non-selective nature of electrical stimulation relative to natural hearing. In natural hearing, a nerve pathway is activated when the characteristic frequency (CF) associated with that pathway is present in the incoming sound. Normal-hearing individuals have approximately 30,000 neural fibers. Neural pathways are tonotopically ordered by decreasing CF along the length of the cochlear duct, and this finely tuned spatial organization is well known (FIG. 1C) [17]. CIs are notoriously bad at reproducing the selective activation of specific neural regions that occurs naturally. Rather, electrical stimulation creates broad excitation patterns as illustrated in FIG. 1D. When the EA is placed farther away from the neural regions, broader excitation patterns are created. Broader patterns create more excitation overlap with neighboring electrodes, which creates so-called channel interaction artifacts, which are known to have a negative effect on hearing outcomes [18]. This is especially problematic for EAs that have electrodes spaced close together as is common for pre-curved EAs. In ongoing studies by our group, we have developed techniques to mitigate some of the effects of channel interaction by identifying electrodes that likely create channel interaction artifacts and deactivating them [19]. The studies of the inventors have shown that this approach leads to significantly improved hearing outcomes, which provides confirmation that channel interaction is indeed problematic [20, 21].

A better strategy for reducing channel interaction artifacts that does not require deactivation would be placing the electrodes as close as possible to the neural regions they activate, aka, perimodiolar placement of the EA. This is the intended result when using pre-curved EAs, but as our data show in the following section, successful perimodiolar positioning of pre-curved EAs is not the norm. Placing the electrodes within the ST cavity of the cochlea is also a factor associated with better hearing outcomes [8-10]. It is thought that trauma to the basilar and Reisnner's membranes as well as the increased potential for cross-turn stimulation are the likely causes for poorer outcomes when electrodes translocate from ST to scala vestibuli (SV). Further, several studies have indicated that poorer outcomes are seen when EAs are placed too deep [8] or too shallow [22-23]. In the ongoing studies by the inventors, more data continue to be collected in our CI imaging database, which continue to provide confirmation of such relationships between electrode location and outcome and permit discovery of yet unknown factors affecting outcomes.

In this invention, we develop and validate pre-operative CT image-analysis and intra-operative guidance techniques for optimizing selection and placement of currently available CI electrode arrays on a patient-personalized basis, with the ultimate goal of improving outcomes.

CI Image Analysis Techniques:

Several groups have developed CI imaging strategies, including development of CT acquisition sequences that provide enhanced visualization of the external walls of the cochlea [24-25]. However, these approaches do not permit identifying intra-cochlear anatomy. Skinner et al. developed an approach that permits estimation of the location of intra-cochlear anatomy by rigidly-registering a high resolution histological atlas of one cochlea specimen, where intra-cochlear anatomy can be visualized, to CT images of new subjects [26]. This was a major step forward, but the methods are labor intensive, making their use in large scale studies prohibitive. Further, the limited accuracy that is achievable when rigidly registering a single cochlea atlas given the high variability in intra-cochlear anatomy [14] hinders its applicability. Our approach is to segment the ST and SV using a shape model such as a non-rigid statistical shape model [27] created with micro CT (µCT) images of 9 *cochleae* specimens in which intra-cochlear structures are visible [11-12]. The shape model can also be a rigid shape model or a rigid statistical shape model. These models are then automatically fit to the external boundary of the patient cochlea that is visible in conventional CT. FIGS. 3A-3C shows a portion of a pre-operative CT scan and the results obtained with our segmentations presented as 3D surfaces and 2D contours. In the studies, we have found average errors of 0.33 mm using our non-rigid model in estimating the position of membrane separating the ST and SV (this is used to determine which scala (ST vs SV) the electrode is in), whereas even with perfect registration a rigid model such as that proposed by [26] has average errors of 0.67 mm [28], which is substantial considering the widths of the ST and SV are about 1 mm. Factoring in errors that occur due to the manual rigid registration step proposed by [26] would increase these errors even further.

Figure 4:
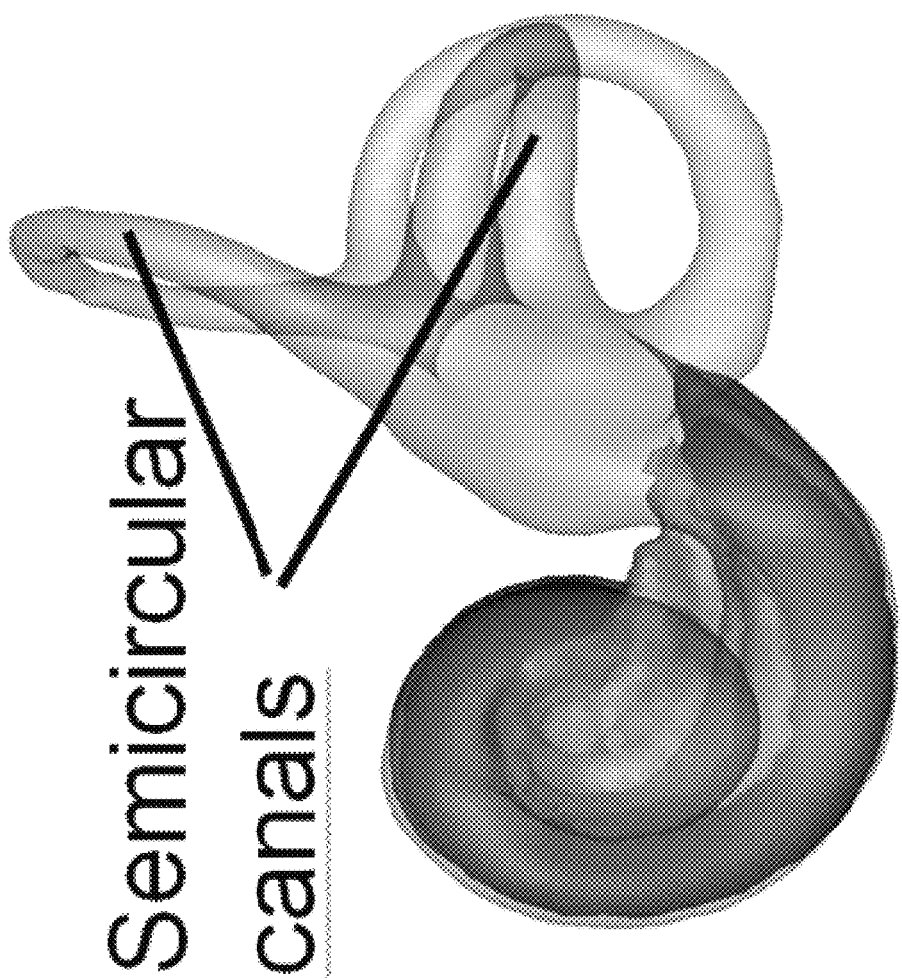
FIG. 4 shows surfaces of the labyrinth (gold), scala tympani (red), scala vestibuli (blue), and modiolus (green) of a cochlea.

Direct fitting of the models to the external walls of the cochlea can only be done in pre-implantation CT because the beam hardening artifacts caused by the EA largely obscure the edges of the cochlea in post-implantation CT. A different type of approach needs to be used if a pre-operative CT scan is not available. In [29] we show there is a high level of symmetry between left and right ear anatomy in individuals, and for unilateral CI recipients we present a method to segment the anatomy of the contralateral ear and project it onto the implanted ear using the transformation that registers the left and right semi-circular canals, as shown in FIG. 4, which are typically not affected by artifacts. In [30] we have developed another algorithm that permits the segmentation of the inner ear in bilateral recipients who do not have a pre-operative CT scan. In these cases a model of the labyrinth constructed using a labyrinth shape library is fit to the post-operative CT scan, relying on the semicircular canals as landmarks. This model is then used to estimate the location of the ST and SV.

Relationship Between Electrode Position and Outcome

Figure 11C:
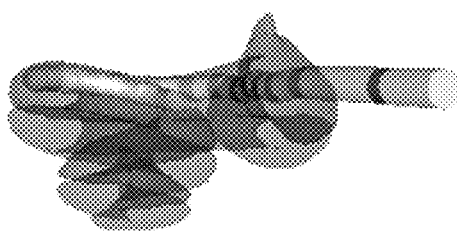
FIGS. 11A-11C show the plan (FIG. 11A) and the resulting electrode location (FIGS. 11B and 11C) for a group A (optimal plan) specimen, according to one embodiment of the present invention.
Figure 11F:
FIGS. 11D-11F show the plan (FIG. 11D) and the resulting electrode location (FIGS. 11E and 11F) for a group B (suboptimal plan) specimen. Surfaces are ST (red) and SV (blue).
Figure 11B:
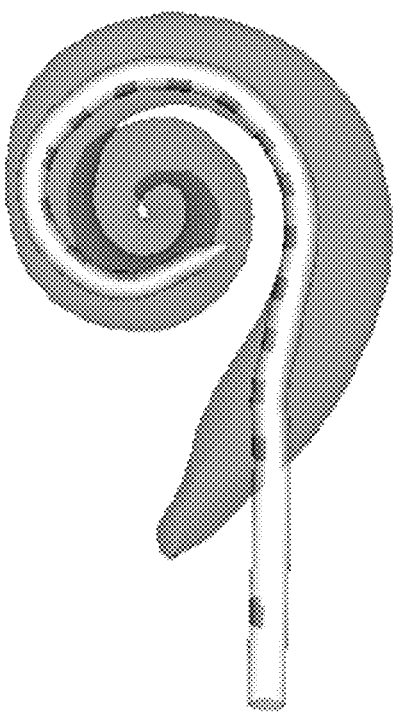
Figure 11E:
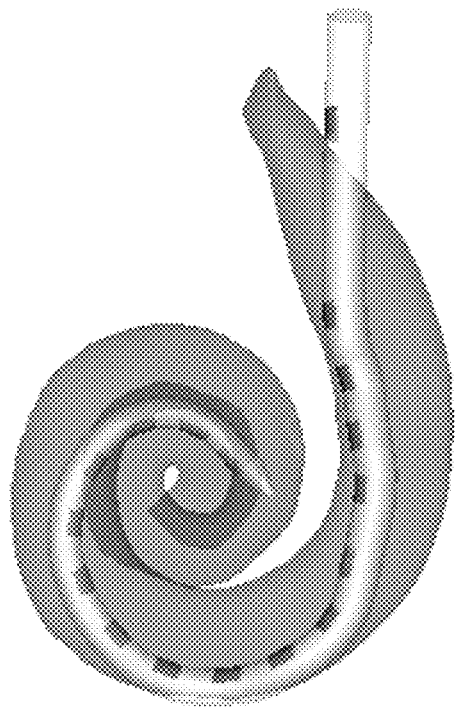

Work from the inventors and several other groups has shown that electrode placement affects hearing outcomes including several studies that suggest that depth of insertion affects outcomes [8, 22-23]. Finley et al. used the approach of Skinner et al. [26] to find the angular position of electrodes and whether an electrode is in the ST or SV in 14 subjects [31]. They then built a linear regression model that suggests that angular position, age, and the total number of electrodes in the SV are predictive of consonant-noun-consonant (CNC) [32] word recognition scores. The inventors have reported that translocation of the EA from ST to SV occurs in approximately 42% of cases where pre-curved EAs are used [9]. An example case is shown below in FIG. 11F. Using the approach of Skinner et al. [26] on 114 subjects, Holden et al. [8] report that better outcomes are correlated with more electrodes inserted in the ST and with electrodes inserted to a more perimodiolar position. In our work using the CI image analysis techniques on 116 implants, we also observe better CNC word scores (48.9% vs 36.1%) in patients with the EA inserted completely within the ST [9].

Measuring modiolar positioning: We have recently confirmed that achieving successful perimodiolar positioning of pre-curved EAs is associated with significantly better outcomes in a study with 54 ears [33]. Here we present an expanded analysis on 83 ears. Electrode location for each subject was found in the post-implant CT using automated electrode localization methods we have developed (see red electrodes in FIG. 5A) [15-16]. The average distance M between the location of the electrodes and the modiolus was used as a measure of EA perimodiolar positioning. General linear models (GLMs) were used to detect the relationship between the principal factors believed to affect outcomes in prior studies [8] (M, scalar location, depth of insertion, age, and length of CI use) and standard audiological metrics including CNC [32] word recognition scores and BKB-SIN [36], which measures the lowest signal-to-noise ratio (SNR) at which sentences can be understood in noise; thus a lower score is better. $M$ ($p<0.01$), scalar location ($p<0.05$), and age ($p<0.01$) were found to be significant factors for both CNC (GLM correlation $r=0.46$, $p<1e-4$) and BKB-SIN ($r=0.58$, $p<1e-7$). These GLMs predict very different outcome with relatively small changes to the position of the EA. A 0.25 mm reduction in $\overline{M}$ is associated with improvement of 11% in CNC and 3.4 dB in BKB-SIN. Scalar translocation is associated with decline of 10% in CNC score and 3.6 dB in BKB-SIN. Average $\overline{M}$ and scalar location are predicted to lead to population average CNC scores of 60% and BKB-SIN of 11.6 dB for 46 year old individuals. An individual of the same age with ST location and an excellent $\overline{M}=0.15$ mm is predicted to score 79% CNC and 5.9 dB. Conversely, a sub-optimal positioning of the EA with $\overline{M}=0.86$ mm with a scalar translocation is predicted to score 39% CNC and 18.5 dB. These results show that successful perimodiolar placement of pre-curved EAs within the ST leads to significantly better hearing outcomes. Average $\overline{M}$ across all subjects was 0.47 mm, which suggests that most individuals have a number of electrodes that are distant to the modiolus where they are not most effective. Thus, advances that permit achieving better perimodiolar placement of pre-curved EAs could significantly improve hearing outcomes.

Pre-Operative Planning of Electrode Placement Procedures

In one aspect, the invention develops pre-operative planning and decision support techniques. While pre-operative CT images are acquired at most centers to visually evaluate the surgical anatomy (e.g., the course of the facial nerve), they are not typically used in making device selections or decisions about electrode insertion techniques. In certain embodiments, analysis of temporal bone anatomy in the pre-operative CT image is used to plan the surgical approach (RW vs cochleostomy (CO) cochlea entry site), including recommending an approach vector, EA base insertion depth, and AOS depth and orientation for pre-curved EAs.

Figure 5A:
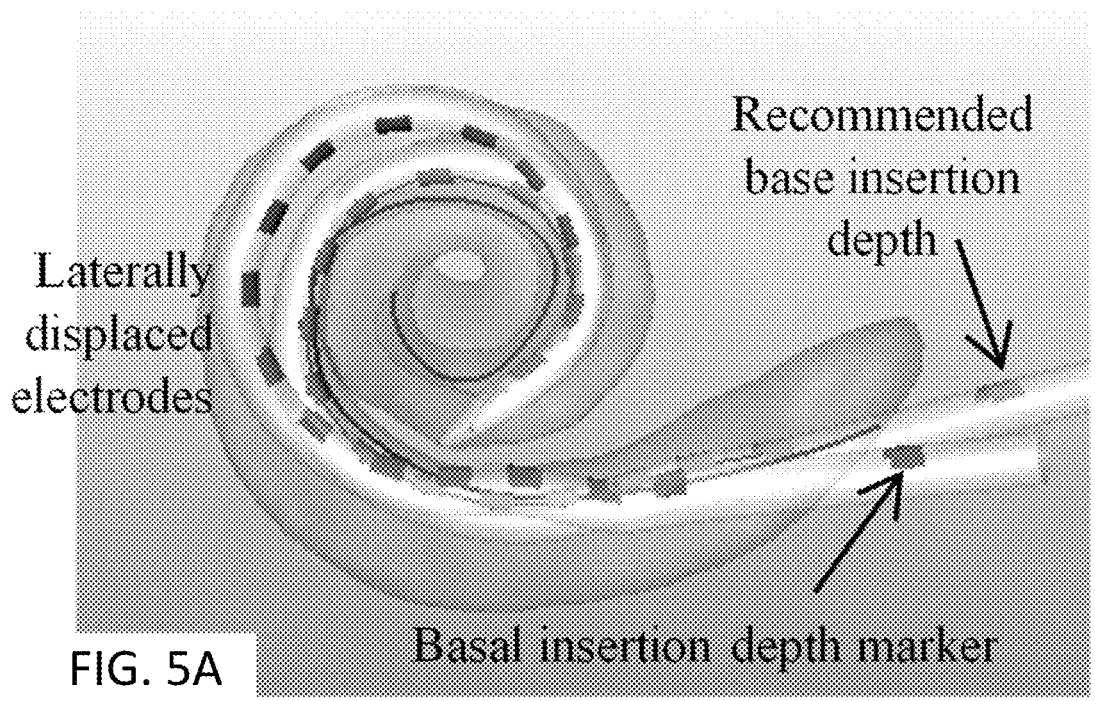
FIGS. 5A-5B show the modiolar curve (blue), registered model array (green), and actual electrode position (red) for two subjects, respectively, according to one embodiment of the present invention, noting that insertion to the generic insertion depth in FIG. 5A caused the electrode to become laterally displaced while the electrode in FIG. 5B has better perimodiolar position but has under-inserted depth of the tip of the array.
Figure 5B:
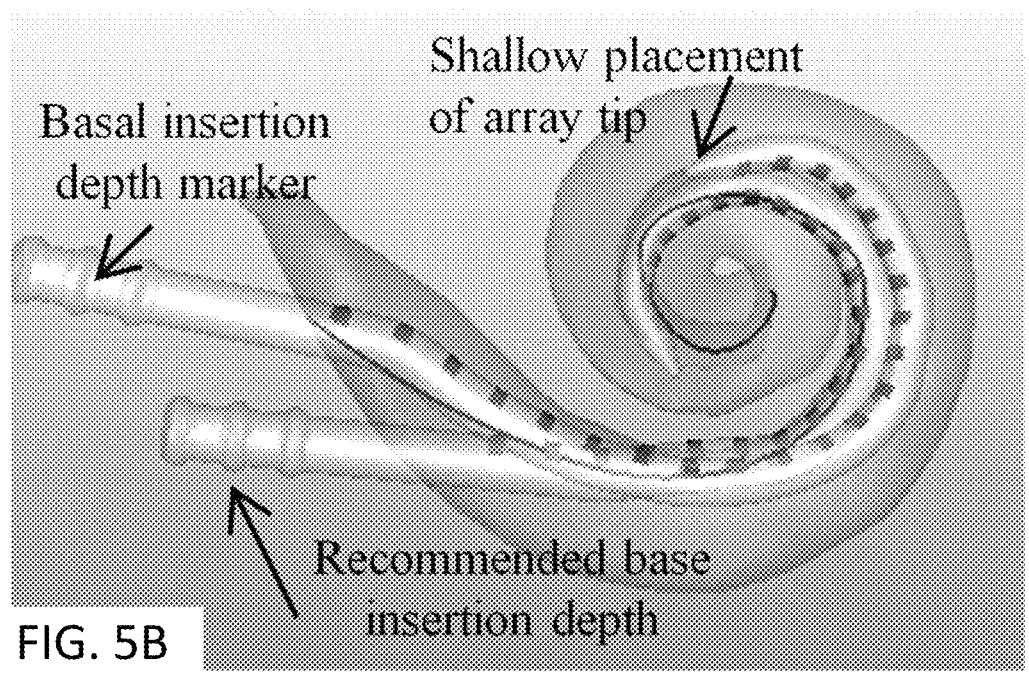
Figure 6:
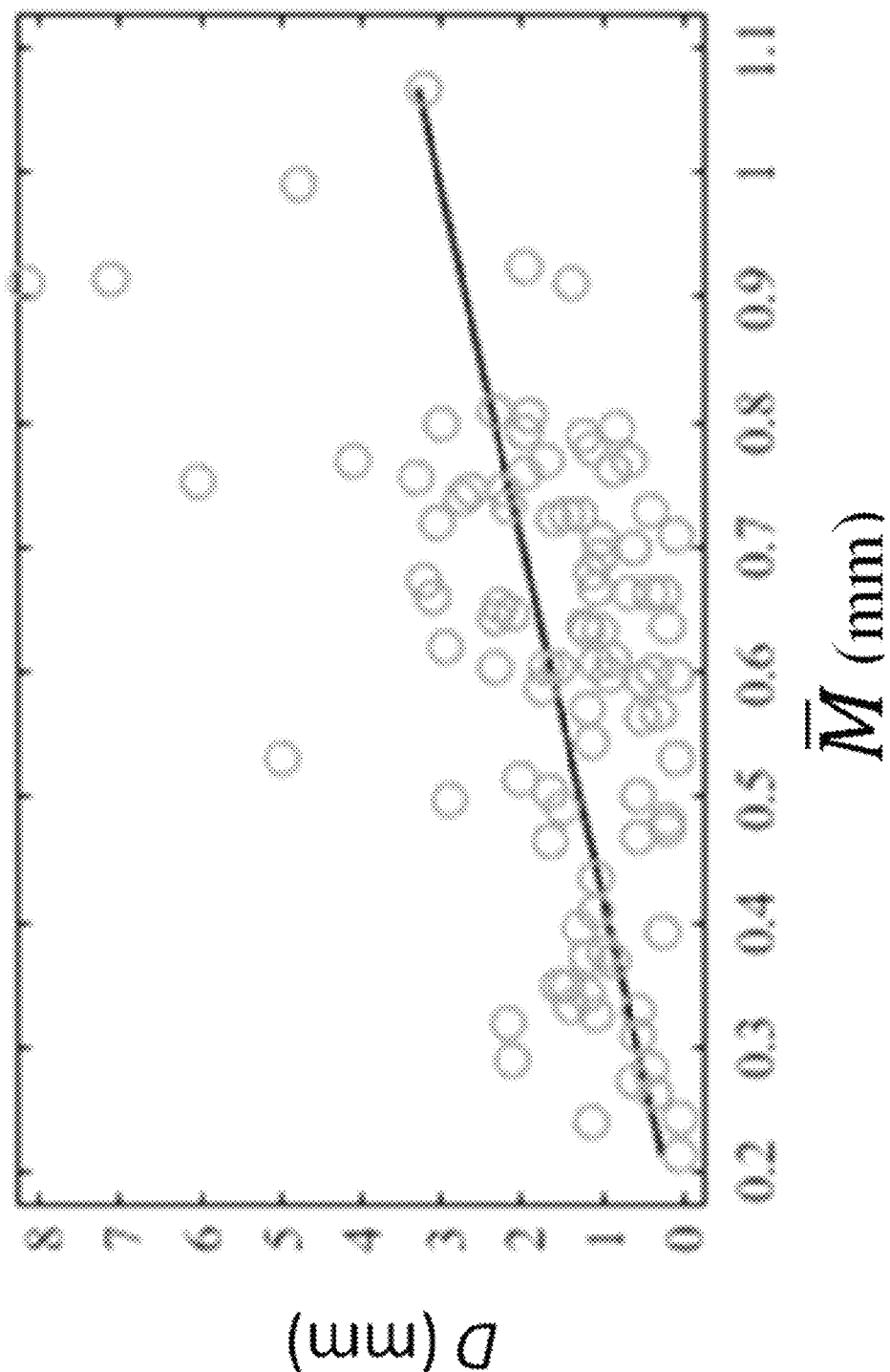
FIG. 6 shows scatter plot of M vs D.

Optimized base insertion depth. Optimized base insertion depth of pre-curved EAs is determined using a novel model-based approach. In certain embodiments, a novel EA shape model is created by acquiring a CT image of the EA in air under no load and measuring the 3D position of each electrode in the EA in the image. This provides an estimation of the resting state shape of the EA. We then register the model to the ideal modiolar position of the patient's ST. To do this, we first define the ideal modiolar position in the ST of a shape model such as a non-rigid statistical shape model that is used to localize intra-cochlear anatomy. In certain embodiments, this was done by manually defining a 3D modiolar hugging curve as a sequence of points within the non-rigid statistical shape model of the ST using 3D object editing software developed in-house. A cubic spline was then fit to the manually selected points to generate a dense and smooth 3-D curve (see blue curve in FIG. 5A-5B) [34]. This manually defined modiolar hugging curve is automatically transformed to a new patient's pre-implant CT using a thin plate spline (TPS) registration [35] of the model ST to the patient ST. Finally, the EA shape model is rigidly registered to the patient's modiolar curve using an iterative closest point (ICP) registration technique [37]. In one embodiment, the patient-customized insertion base depth is determined as the depth of the base of the registered EA shape model. We have retrospectively evaluated this approach on a dataset of pre- and post-implantation CT scans of 97 ears, of which 82 and 15 were implanted with Cochlear Contour Advance and Advanced Bionics Mid-Scala pre-curved EAs. Shape models were created for both EA types. Example results of the model registration process are shown as the green electrodes in FIGS. 5A-5B, which represents the EA shape model after registration to the modiolar curve for two cases. Once the base of the EA has been inserted to the model recommended depth, the EA has returned to its resting shape and the tip of the EA has reached the desired angular insertion depth. Deeper insertion of the EA base would likely not result in further advancement of the tip of the EA. An example case where this has likely occurred is shown in FIG. 5A, where the red EA represents the actual electrode position for this subject. As can be seen in the figure, the basal depth marker was inserted about 2 mm past our model recommended depth, resulting in lateral displacement. On the other hand, inserting the base of the EA shallower than the recommended depth would lead to shallower depth of the tip of the EA, which also could be detrimental to outcome as the range of nerves stimulated by the EA would be reduced. A real representative case where this occurred is shown as the red EA in FIG. 5B. The basal depth marker was placed about 2 mm further from the entry site than recommended by our model. While the electrodes are perimodiolar, the tip of the EA is much shallower than the expected depth demonstrated by the green EA. In our tests on 97 ears, our proposed approach was used to recommend base insertion depth using the pre-implant CT. We then measured the distance D between the position of the depth marker on the surgically placed EA found in the post-implant CT and the position where the marker is recommended to be by the techniques described above. Pearson correlation was computed between D and $\overline{M}$, the average distance between the actual location of the electrodes and the modiolar curve. A significant positive relationship was observed (r=0.46, p<0.0001). Average $\overline{M}$ is 0.51 mm when D<1 mm and is 0.62 mm otherwise. Inspection of a scatter plot of these data, as shown in FIG. 6, reveals that perimodiolar placement occurs only when D is small, i.e., when the base insertion depth roughly matches the depth recommended by our proposed method. However, in many cases where D is small, perimodiolar placement is not achieved. Altogether, these results strongly suggest that when our patient-customized electrode insertion depth technique is implemented, it will increase the fraction of cases in which perimodiolar placement of the EA is achieved, which lead to better hearing outcomes. However, this method alone will not guarantee perimodiolar placement, and additional forms of guidance, including ones that decrease translocations from ST to SV might further improve the likelihood of perimodiolar placement.

In certain embodiments, the approach is extended to recommend the base insertion depth of straight EAs. Straight EAs are available in a wide variety of lengths. Research has indicated outcomes are maximized with straight EAs when the electrodes are distributed over a desired intra-cochlear range defined by the angular insertion depth of the most distal and proximal contacts (see FIGS. 2A-2B). It is known that when using the generically recommended base insertion depth, the angular insertion depth of the tip electrode for straight EAs is dependent on the cochlea size. Manual CT-based measurements of cochlear dimensions have been proposed as an indirect measurement of the length of the path a straight EA takes within the cochlea [47]. We have recently proposed an automated, labor-free approach where we directly measure the length of the electrode path along the lateral cochlea wall [48]. Similarly to define the modiolar curve, we define a lateral wall curve manually in our intra-cochlear anatomy model and can automatically map it to new patient scans. We propose to determine the recommended base insertion depth as the one for which the tip of the EA would reach the desired angular insertion depth when following the lateral wall curve. Our preliminary studies have shown that with straight EAs, hearing outcomes are maximized once an insertion depth of at least 500° is achieved [48].

Figure 7:
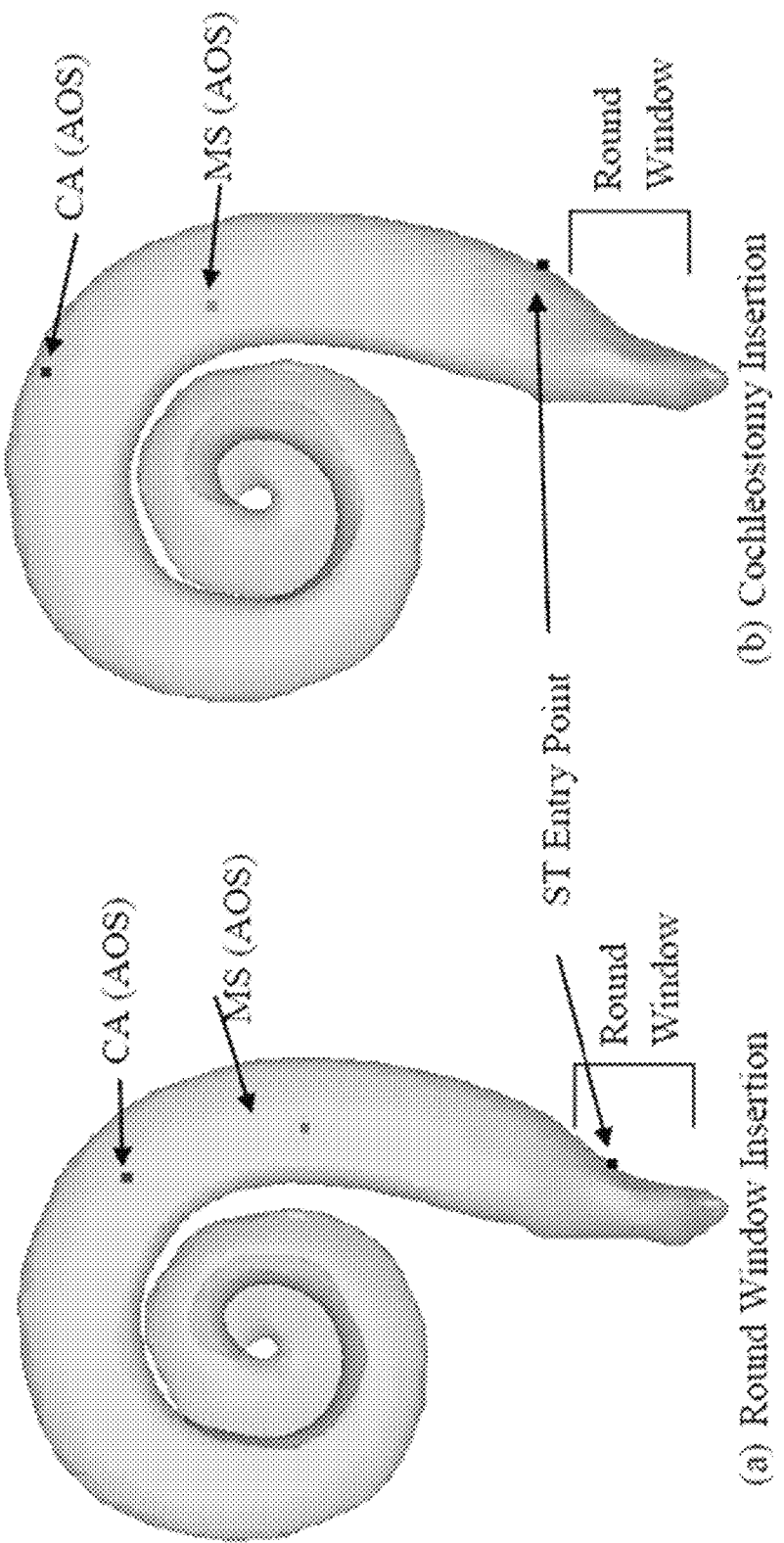
FIGS. 7A-7B show CA(AOS) and MS(AOS) that are the insertion depths of the most distal electrode when the AOS marker reaches the entry site with Cochlear Contour Advance (CA) and Advanced Bionics Mid-Scala (MS) arrays, respectively, according to one embodiment of the present invention.

AOS Depth & Orientation. With pre-curved EAs, the EA is threaded into the cochlea while loaded onto the straightening stylet until the AOS-marker on the EA reaches the entry site, indicating that the generically recommended AOS procedure initiation depth (a.k.a., AOS depth) has been reached. The surgeon then advances the EA off the stylet into the cochlea until the desired base depth is reached. FIGS. 7A-7B show the generically recommended AOS depth for two pre-curved EA types when using two different entry sites in FIGS. 7A and 7B. The path of the EA within the cochlea is determined by the AOS depth, the orientation of the EA (i.e., the direction of EA curvature as it is advanced off the stylet), and the interaction between the EA and intra-cochlear anatomy. Performing AOS from a sub-optimal depth or at a sub-optimal orientation is thought to increase the likelihood of scalar translocations and folded EAs. In our prior work, we found scalar translocation, i.e., EAs that cross from ST to SV, to be a problem primarily with pre-curved (42% occurrence rate) rather than straight EAs (11% occurrence rate) [9]. Folded EAs occur when the tip of the EA becomes stuck as the EA is advanced into the cochlea. Our studies have shown that EA folding appears to occur quite rarely (2-3%) but is often not identified and leads to drastically poorer hearing outcomes [57]. We have also conducted preliminary studies that show that the generically recommended AOS depth defined using the AOS marker on the EA places the tip of the EA at an angular depth in the cochlea that is highly variable across individuals (st. dev. about 15°) [39]. Further, relatively small differences of 1.5-2 mm in AOS depth correspond to relatively large differences in angular insertion depth of 30°. This suggests the AOS depth used clinically is often not optimal. In preliminary insertion experiments outlined below, it was noted that determining the best EA orientation without guidance also may be more difficult than conventional wisdom suggests. This is supported by studies showing that anatomical structures within the surgical field of view that the surgeon uses as landmarks are not strongly related to the position and orientation of the cochlea [14].

Figure 8:
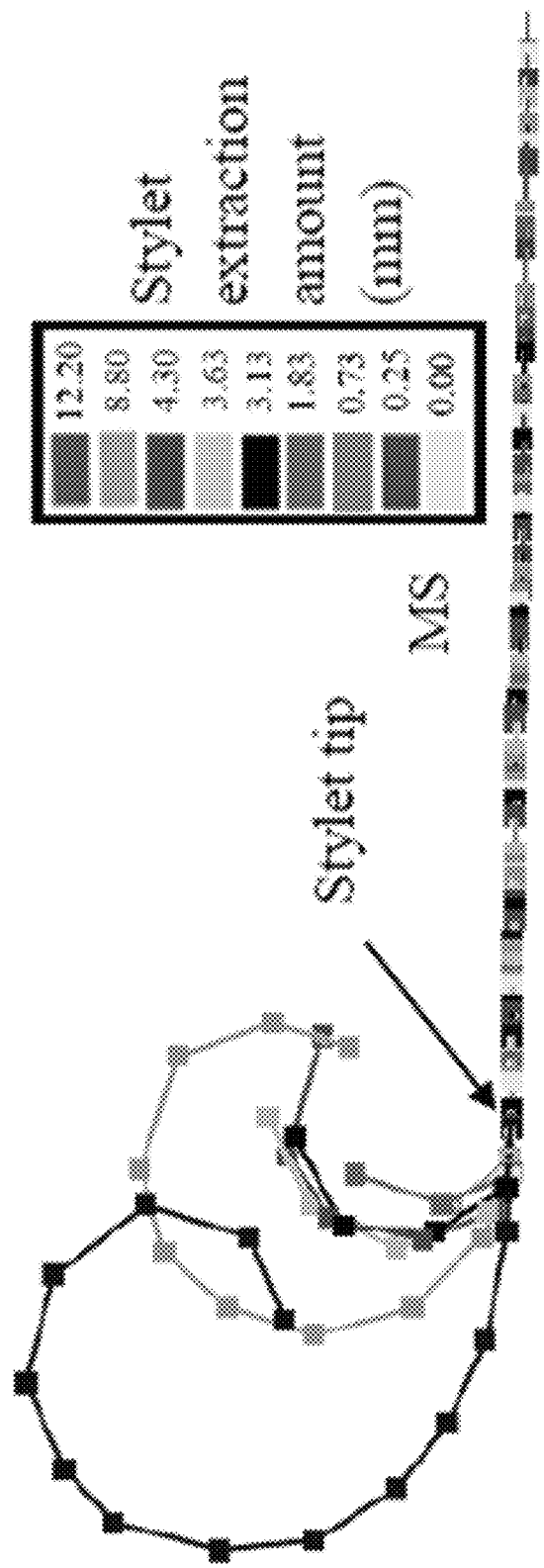
FIG. 8 shows shapes of pre-curved arrays as a stylet is removed, according to one embodiment of the present invention.
Figure 9B:
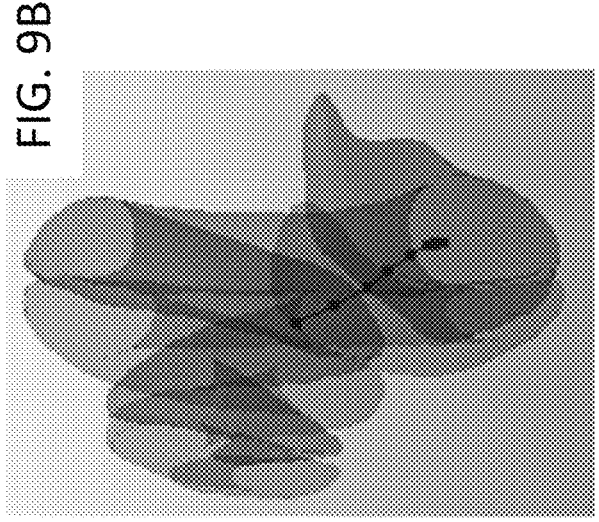
FIGS. 9A-9D show an electrode trajectory model at 3 mm AOS, according to one embodiment of the present invention. Using the generic AOS depth and sub-optimal array orientation shown in FIGS. 9A-9B is more likely to result in translocation to SV than an optimized AOS depth and orientation shown in FIGS. 9C-9D.
Figure 9D:
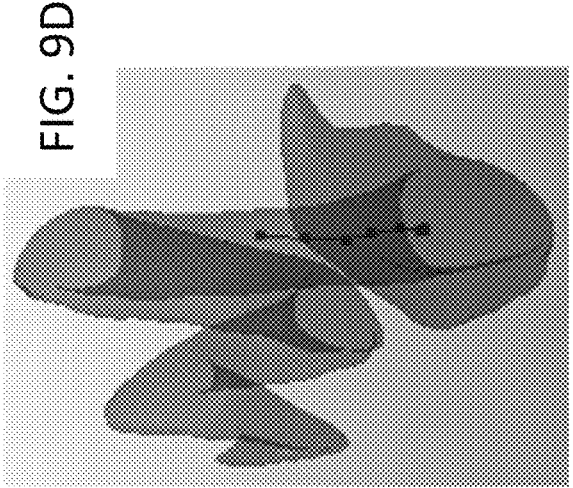
Figure 9A:
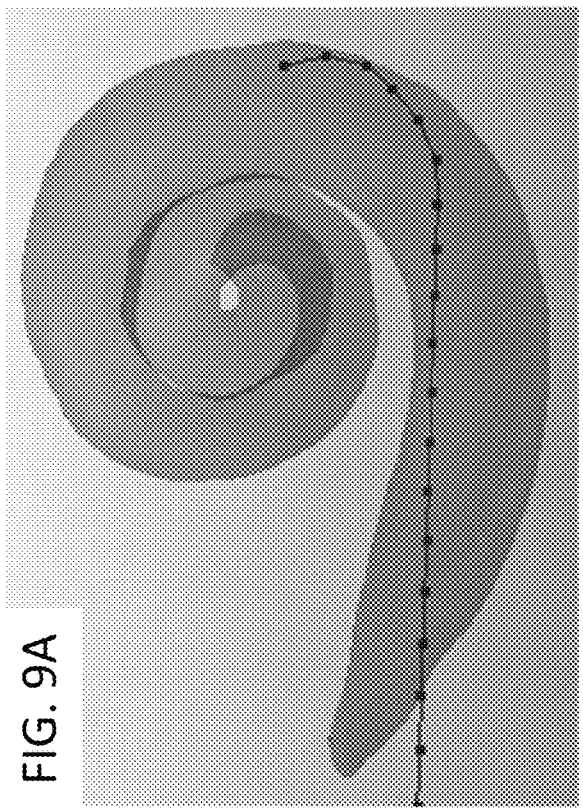
Figure 9C:
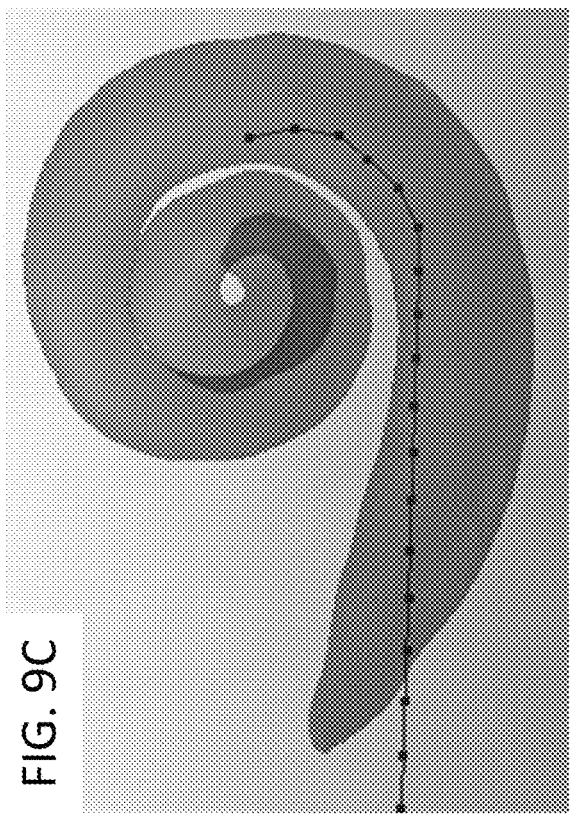

To facilitate recommending the optimal EA orientation and depth of AOS, we have developed an electrode model-based approach. We extend the rigid model of the resting state shape of the EA to be a stylet position-dependent trajectory model of the EA. To do this, a group of practice EAs of the Cochlear Contour Advance (CA) and Advanced Bionics Mid-Scala (MS) EAs were used. For each EA, the straightening stylet was retracted by an amount in the range from 0 mm to fully removed. The exact retraction distance was measured precisely using digital calipers under a microscope. A 3D reconstruction of each of these EAs was then performed by localizing the position of each contact in a CT scan that was acquired of the EA with the stylet at the measured distance of retraction. The results of this process are shown in FIG. 8, where each of the EAs is color-coded by stylet retraction amount in millimeters. In the figure, the 3D reconstruction of each EA is aligned such that the tip of the stylet is co-located across EAs. The shape of the EA at the largest retraction amount is equivalent to the final relaxed shape of the EA with no stylet. Using these exemplars, we can simulate the shape of the EA at a new stylet extraction amount by interpolating a weighted average between shapes. For interpolation, we treat each electrode array as a sequence of linear segments attached at joints. Each electrode position is treated as a joint between line segments. Then, to interpolate new shapes, we linearly interpolate the joint angles between exemplar arrays. Using this scheme, the trajectory of an EA as it is advanced off the stylet can be simulated by iteratively estimating the shape of the EA while increasing the amount of stylet retraction from 0 mm to fully retracted. This model has been used to quantify the agreement between the EA trajectory and the modiolar curve of the cochlea when using the generically recommended AOS depth. It was found that using the generically recommended AOS depth leads to average distance of about 0.5 mm between the EA trajectory and the modiolar curve [39]. FIGS. 9A-9D show the CA trajectory model at 3 mm AOS superimposed on an example cochlea. FIGS. 9C-9D show how adjusting the generic AOS-depth by 1 mm and optimizing EA orientation can increase the likelihood of perimodiolar positioning in ST compared to non-guided conditions shown in FIGS. 9A-9B.

In certain embodiments, an AOS depth and EA orientation selection approach relies on this stylet position dependent electrode trajectory model. We propose to optimally select the AOS depth and orientation using the model. We develop an AOS depth optimization approach that aims to minimize the average distance between the EA model trajectory and the modiolar curve during the first few millimeters of AOS insertion where proper aiming of the tip of the EA is the most critical as illustrated in FIGS. 9A-9D. We use the orientation of the registered EA model as the recommended EA orientation.

Figure 10:
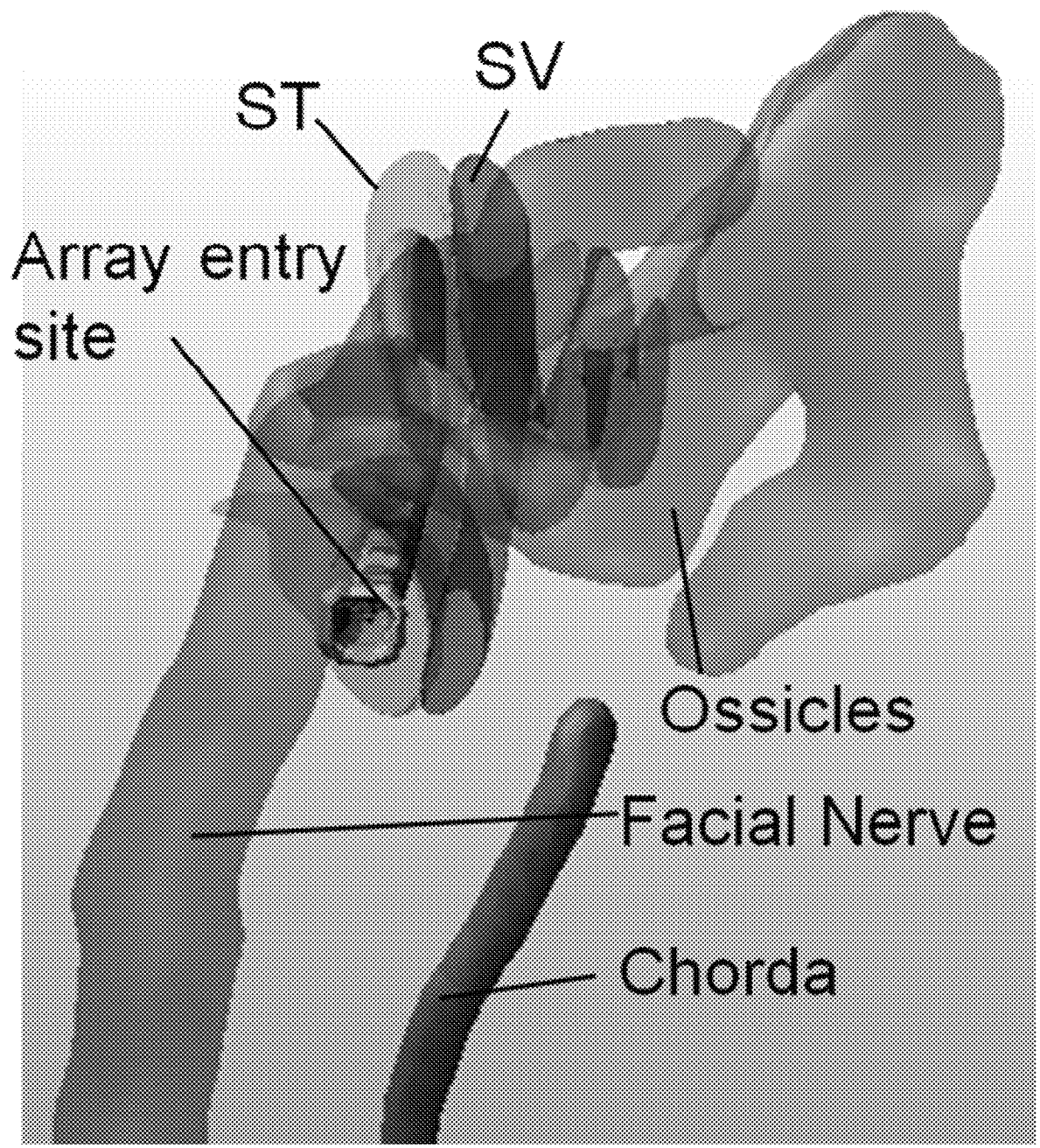
FIG. 10 shows a view along optimal entry vector.

Entry vector and site. Choosing the best entry vector and site is important for ensuring that path of the EA within the cochlea is smooth and does not cause trauma. Studies by in the inventors have shown that anatomical structures within the surgical field-of-view that the surgeon uses as landmarks to determine EA insertion vectors are not strongly predictive of the position and orientation of the cochlea [14]. Thus, guidance could reduce trauma and potentially reduce the likelihood of scalar translocation and intra-cochlear EA buckling. The trajectory must also be confined by the borders of the surgical approach defined by the mastoidectomy and the walls of the facial recess. The facial recess is the surgically created opening from the mastoid to the middle ear which provides access to the cochlea. Its anterior and posterior borders are defined by the location of the facial nerve and one of its branches, the chorda tympani. We have developed automatic techniques for identifying the facial nerve and chorda tympani using model-based optimal path finding techniques and other ear structures such as the stapes and incus using atlas-based techniques [40-41]. We have also developed automatic trajectory finding algorithms designed to find percutaneous drill paths from the mastoid surface through the facial recess to the cochlea for minimally-invasive, image guided CI surgery [42]. This approach is designed to find a probabilistically safe drilling trajectory that is also collinear with the basal turn of the ST to facilitate smooth insertion of an EA that is threaded through the drill well. A view along an example optimal EA entry vector and the segmented structures of interest are shown in FIG. 10. In this case, the optimal entry vector that is collinear with the base of the ST passes directly adjacent to the facial nerve through an extended RW entry site of the ST.

In certain embodiments, the trajectory optimization approach is modified for finding entry trajectories that are constrained by the facial recess. This involves adjusting parameters that control distance constraints. For example, it is important for a drilling trajectory to be distant from the facial nerve to avoid catastrophic injury, whereas this is not the case for our electrode insertion trajectory as there is no risk posed by the EA being close to the facial nerve during the insertion procedure as shown in FIG. 10. Selection of the entry site is also important. RW is desirable when it is feasible, but sometimes expanding the RW or performing a cochleostomy is necessary to achieve smooth entry into the cochlea. The trajectory optimization approach is also modified to include selection of the entry site, which is done by defining an appropriate weighting between the importance of having a trajectory that is collinear with the basal turn of the ST and avoidance of a potentially more traumatic cochleostomy or RW expansion.

Figure 14:
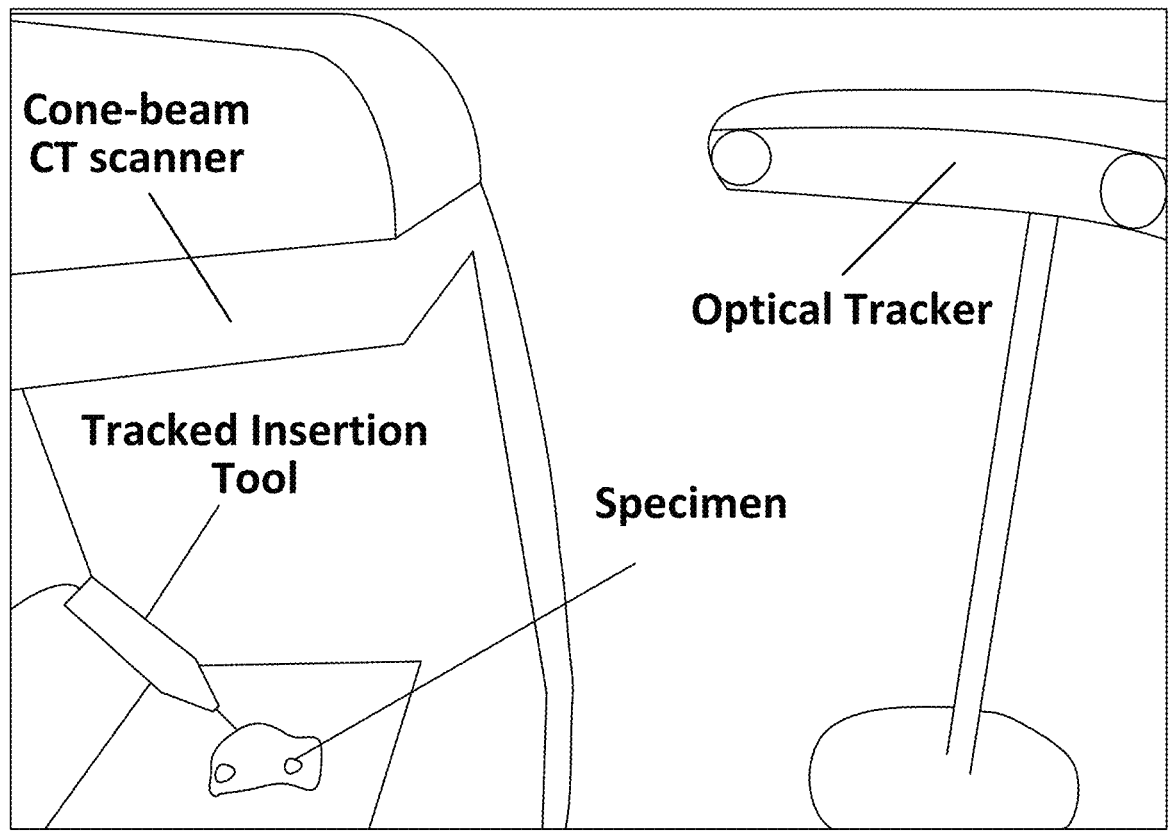
FIG. 14 shows an experimental setup with tracked insertion tool permitting sequential CT scanning, according to one embodiment of the present invention.

Evaluation: In certain embodiments, an electrode insertion tool is designed so that it can be fixed relative to the temporal bone, similar to tools we have designed in the past [55]. Then, the surgeon is asked to position the tool such that the EA follows the "optimal" plan as disclosed above with either the tracker or tracker-free approach. Then the insertion is conducted in 7 steps representing critical timepoints in the procedure: advancement on stylet halfway to AOS point, advancement to AOS point, and 1 mm, 2 mm, 5 mm, 10 mm, and full insertion after initiating AOS. After each step, the system is fixed in place and a CT scan is acquired. Using the electrode position detection software we have developed [15-16], this CT scan allows us to reconstruct the trajectory of the EA, similarly to the trajectory model in FIG. 8, as it is inserted into the cochlea. We can then compare the planned trajectory to the actual trajectory to learn how our planning or instruction approach might need to be adjusted. For example, if we see that the tip of the EA tends to strike the modiolar wall after initiating the AOS procedure instead of smoothly advancing into the scala tympani, we know that we need to redesign our planned AOS depth, angle of insertion, or entry site to achieve a more optimal result. Or, for both pre-curved and straight EAs, if the resulting depth of insertion tends to not agree with the planned depth because the EA takes a shorter or longer path through the cochlea than our modeling predicts, we know that we need to modify our EA intra-cochlear trajectory model. We have prototyped this system and piloted it with one temporal bone specimen with tracker-free guidance (FIG. 14), where the tracker was used only to record the experiment. One of a number of findings was that more precise instructions on entry site may be necessary as the coarse entry site instruction of "extended RW" resulted in 1.5 mm disagreement between planned and implemented entry points. This altered the entry vector by 20 degrees, leading to a scalar translocation, which is consistent with our GLM prediction of translocation for suboptimal entry vectors. Time sequence CT imaging of cochlear implantation is novel to the best of our knowledge and has promise of containing a wealth of information critical for learning the optimal electrode position planning approach, as evidenced by knowledge gained from 1 experiment. We plan to optimize our approach over 3 iterations with 8 temporal bones in each iteration, as our prior studies have indicated that population variance is well represented by 8 *cochleae* [11].

EA Selection

In certain embodiments, the image analysis methods are used to identify which electrode models work best for an individual patient. Such an approach leads to better positioning of EAs with or without the use of other guidance approaches we propose and thus is the technique that is best positioned for fast clinical adoption. We have proposed and have begun evaluating a technique for pre-curved EAs. We propose determining which pre-curved EA types are suitable for a patient by finding which EA shape models best agree, i.e., have the smallest registration error, with the patient's modiolar curve after rigid registration to the patient's modiolar curve. We have retrospectively evaluated this approach on a dataset of pre- and post-implantation CT scans of 97 ears, of which 82 and 15 were implanted with Cochlear Contour Advance and Advanced Bionics Mid-Scala EAs. When looking at the entire dataset, M, the average distance between the actual location of the electrodes and the modiolar curve, was found to be uncorrelated with the registration error of the corresponding EA shape model. However, among the 20% of cases where the base depth of the registered shape model was closest to the generically recommended RW site, it was found that M is correlated with registration error (r=0.45, p<0.05). This is not surprising given the results shown in FIG. 6 above, which show that perimodiolar placement can only be achieved when insertion depth agrees with the depth recommended by our model, and the majority of the electrodes in our dataset of 97 ears were inserted to the generically recommended depth. Altogether, these preliminary results suggest that model registration error has value as a predictor of perimodiolar positioning of different EA types, but only when the base depth of electrode insertion matches the model recommended depth. Thus, we propose registration error can be used to identify which electrode models would be most suitable for an individual when inserted to the recommended depth.

In certain embodiments, the EA selection approach is extended to straight EAs. One technique for selecting straight EAs has been proposed based on measurements of cochlea size [47]. However, this approach is not in widespread use perhaps due to the additional labor required to make the measurements of the cochlea in CT scans. Using the automated, labor-free approach to define the lateral wall curve in the cochlea, we propose to determine which straight EA models would be suitable to be the ones with length such that when placed along the lateral cochlear wall curve, the angular insertion depth of the distal contact reaches 500°, which has been shown the be the depth the EA needs to reach to maximize outcomes, while the proximal contact falls safely within the cochlea)(>30°. This approach should ensure an EA model is selected that will not result in over- or under-insertion. To evaluate our method, four of the most commonly used models will be evaluated, including the Cochlear Contour Advance (CA), Advanced Bionics Mid-Scala (MS), Advanced Bionics 1J (1J), MedEl Standard (ME) EAs. CA and MS are pre-curved, and 1J and ME are straight. For the pre-curved EAs, 10 (this N will allow detecting 1.3 SD) temporal bones are identified as bones where MS is recommended over CA and another 10 are identified where CA is recommended over MS. Both groups are randomly split with half implanted with MS and the other with CA EAs. After EA insertion, high resolution μCT imaging is performed to collect the electrode position outcome measures shown in Table 1 (insertion depth, perimodiolar distance, and scalar position, and adherence to planned insertion depth). Differences in electrode position between the population of bones where the recommended electrode is used and the population where the other electrode is used will be measured to characterize the effectiveness of our proposed electrode selection techniques. The same approach is implemented for the two straight EA types. All insertions are done with recommended base insertion depth instructions provided to the surgeon, as our preliminary studies show that matching the recommended depth is necessary for perimodiolar positioning and is easily achievable with simple instructions.

Intra-Operative Guidance of Electrode Placement Procedures

Tracker free method: one of the objectives of the invention is to develop intra-operative guidance techniques that facilitate implementing pre-operative plans. This includes developing a strategy for conveying insertion plans conceptually to the surgeon without the use of intra-operative tracking. One benefit of such an approach is that it does not require any new and potentially expensive equipment to the operating room, which would lower the barrier for adoption of these technologies. We propose that all of the surgical technique recommendations disclosed above could be provided to the surgeon by combining interactive software for visualization of a simulated procedure and textual instructions relative to anatomical landmarks. To demonstrate the potential utility of such an approach, we have implemented a preliminary version where only textual instructions are provided without the benefit of visualization and have tested it on 20 temporal bone specimens. Each specimen was implanted with an Advanced Bionics Mid-Scala EA by an experienced surgeon. The specimens were evenly divided randomly into groups A and B. For group A, an optimized plan was made. For group B, a plan that is realistic but predicted by our recommendations to lead to poor electrode placement was implemented. In each case, the surgeon was masked to the identity of the plan. An example group A plan is:

Entry site: Insert through the round window (RW) membrane.
Entry vector: Choose entry angle to hug the facial nerve and pass 1 mm inferior to the stapes.
AOS depth: Insert EA on stylet until the AOS marker is 1.5 mm inside RW (electrode 7 reaches RW)
Base insertion depth: Advance off the stylet until proximal insertion depth marker is 0.5 mm outside RW.

Figure 11A:
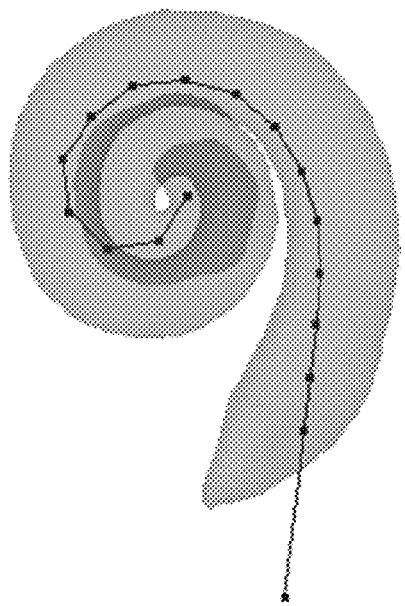

In FIG. 11A, the EA model is superimposed on this specimen's ST at the recommended entry vector and base insertion depth. An example group B plan is Entry site: Extend RW to permit entry at anterior/inferior corner of RW membrane.
Entry vector: Choose entry angle to be 1 mm inferior to stapes centered between facial nerve and chorda.
AOS depth: Insert EA on stylet until the AOS marker reaches the RW.
Base insertion depth: Advance off the static stylet until proximal overall depth marker reaches the RW.

TABLE 1

Experimental results.

| Value | Group | Scalar Location (ST %) | Angular Depth ( ) | Mean Modiolar Dist (mm) | \|Actual-Plan Depth\| (mm) |
|---|---|---|---|---|---|
| Average | A | 100 | 362 | 0.51 | 0.74 |
| | B | 60 | 376 | 0.60 | 0.66 |
| | Pat | 47 | 392 | 0.54 | 1.05 |
| St. Dev. | A | | 16 | 0.09 | 0.89 |
| | B | | 38 | 0.15 | 0.58 |
| | Pat | | 75 | 0.13 | 0.74 |
| p | A vs B | 0.030 | 0.302 | 0.115 | 0.815 |
| | A vs Pat | 0.006 | 0.130 | 0.501 | 0.368 |
| | B vs Pat | 0.543 | 0.473 | 0.284 | 0.145 |

Figure 11D:
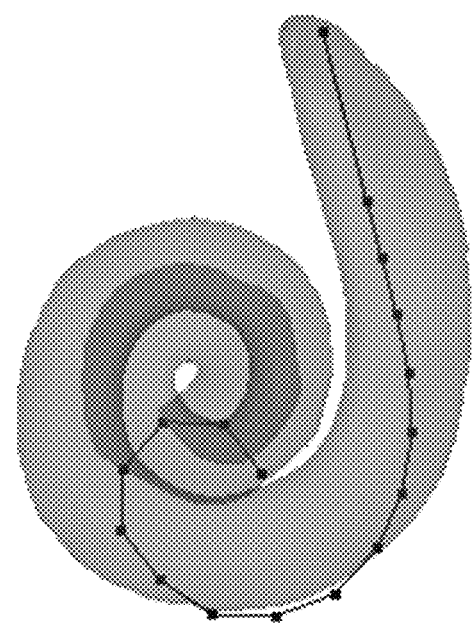

The resting state EA model at this instructed entry vector and base insertion depth is superimposed on this specimen's ST in FIG. 11D. This is a realistic plan that follows the generically recommended approach, but as can be seen in the figure, it is sub-optimal for this cochlea as a shallower depth would permit better perimodiolar positioning. For each specimen, a post-insertion CT scan was acquired to determine electrode position. Overall results are shown in Table 1. Also shown in the table are the results from the group of 17 actual patients (Pat) who have been implanted with MS EAs at our center. Two-tailed rank sum tests were used to assess differences in the rate of ST placement among the different groups. Unpaired two-tailed t-tests were used to assess statistical differences in angular depth, modiolar distance, and agreement between the actual and planned insertion depth of the base of the EA. As shown in the table, no significant differences were detected between the B and patient groups, indicating that our control test instructions were not dissimilar to traditional surgical techniques. Our image-guided electrode insertion technique resulted in full ST placement in every case. This was a significantly higher rate than both the control tests and patient cases. Significant differences were not detected in angular insertion depth and in the difference between the actual and the planned base insertion depth. Thus, adherence to the planned base insertion depth was good. Overall mean modiolar distance was also reduced in group A plans, but this difference was not found to be statistically significant. Two sample, two-tailed t-tests with unequal variance were used to assess modiolar distance for each electrode individually across the experimental and control groups. After Bonferroni correction for multiple comparisons, it was found that the experimental plans resulted in significantly lower modiolar distance for E6-E9 and significantly higher distance for E15-E16. This can be visually appreciated in three-dimensional renderings of representative experimental and control cases are shown in FIGS. 11A-11F. As can be seen in the figure, the middle portion of the EA in the group B case lifts away from the modiolus, whereas the EA in the group A case is perimodiolar. A potential drawback of this approach is that it is more likely to position the most basal electrodes closer to the cochlea entrance and more distant to the modiolus. One way to address this is to recommend that the audiologist evaluate the most basal electrodes for deactivation at programming. Recent research studies support this idea as they have shown the benefit of deactivation of electrodes that are determined to be less effective [19-21]. With deactivation as an option to account for electrodes placed near the entrance of the cochlea, we anticipate that the benefits of better perimodiolar positioning of the rest of the array will outweigh this potential drawback. Altogether, these results strongly suggest that our instructional guidance approach can be followed and will lead to better placement of EAs.

GLMs were used to study the importance of each specific instruction on achieving optimal electrode placement. Pooling results across all 20 A and B group cases we find that the recommended entry vector is significantly ($r=0.83$, $p=0.0006$) associated with achieving ST location, with a 7.5 degree deviation from recommended vector expected to result in a translocation. Entry vector, overall depth, and entry site are significantly ($r=0.77$, $p=0.0023$) associated with achieving low modiolar distance; and entry vector and entry site are significantly ($r=0.72$, $p=0.0019$) associated with achieving high angular depth. These results are already significant and have high correlation on this small dataset of 10 cases per condition.

In certain embodiments, software to automatically determine recommendations is disclosed. Also developed is software that complements the instructions with interactive visualization of a simulated insertion procedure. Further, we add EA orientation recommendations to the list of electrode insertion procedure instructions for the AOS procedure of pre-curved EAs. The ossicles, particularly the stapes, are a nearby landmark that could be used to provide orientation reference. Thus we plan to implement an instruction such as, "Choose the orientation such that the electrodes are facing a point 0.5 mm anterior to the center of the stapes footplate." We have developed registration-based techniques for localizing the ossicles, including the stapes [41]. However, with maximum localization errors of over 1 mm, this approach may not always be accurate enough to be reliably used for this purpose. We plan to construct an active shape model of the ossicles as we have done for intra-cochlear anatomy (see Section 2.2.1) to use for more accurate segmentation of the ossicles. Similarly to intra-cochlear anatomy, the ossicles are very small and their features are difficult to see in CT. To construct the model, for training data we will rely on the μCT images of the first 10 specimens that we will collect. These will be manually labelled and used to construct the model. The technique will be validated by testing the model to segment pre-implant CT images of the same specimens in a leave-one-out fashion. The μCT of the left-out specimen will be used as a ground truth to validate the results. Until we develop a more accurate method, our current method will be used, and its results will be manually corrected as necessary before creating electrode placement plans.

In certain embodiments, we develop software that automates the creation of the instructional plan. Further pilot testing is conducted to evaluate which anatomical landmarks referenced in the instructions are most appropriate for each step of the procedure. Once the landmarks are finalized, automated algorithms are developed to produce the electrode insertion procedure instructions such as those described above.

Figure 15A:
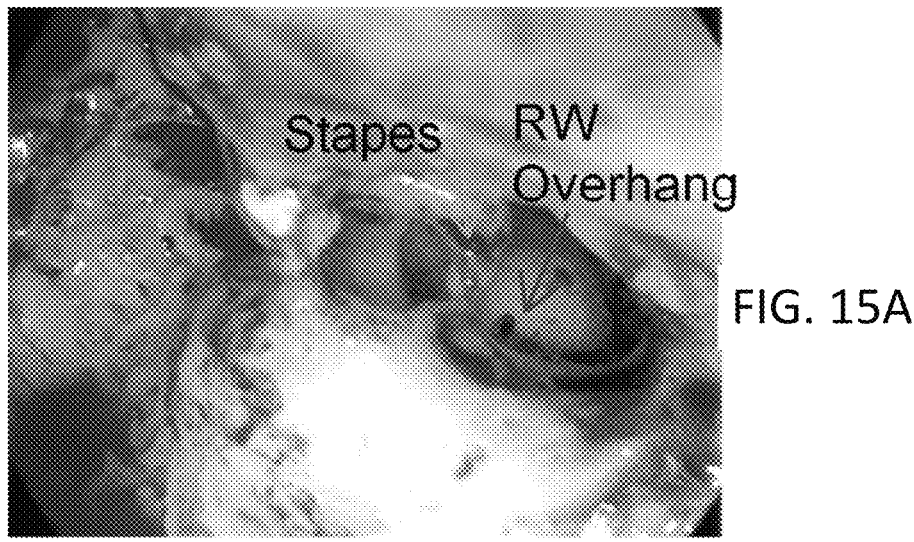
FIGS. 15A-15C show microscope (FIG. 15A) and virtual (FIGS. 15B-15C) mastoidectomy views, respectively, according to one embodiment of the present invention. Similar anatomical structures are indicated by the colored arrows.
Figure 15B:
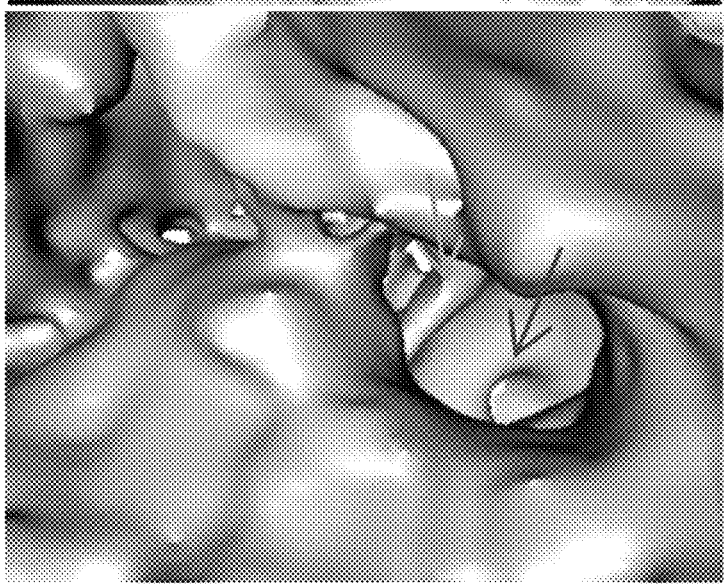
Figure 15C:
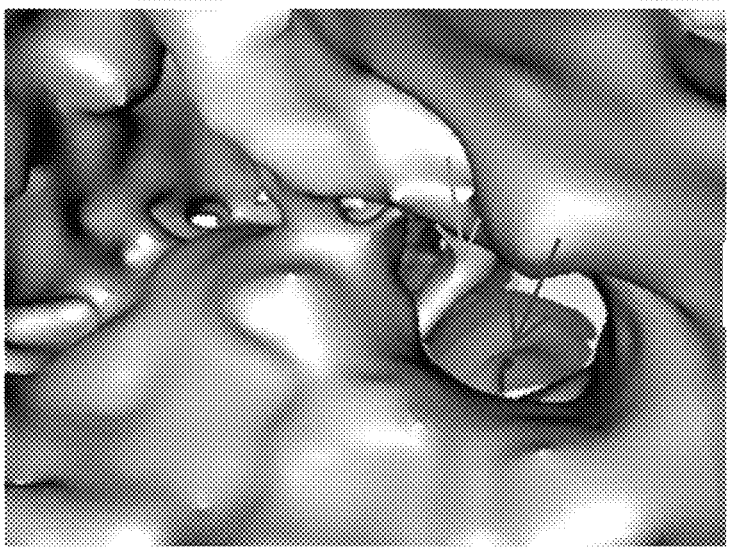

In addition, we develop interactive software that complements the instructions with visualization of a simulated insertion procedure. This is a graphical user interface that permits 3D visualization of electrode insertion from surgical view with the added ability to interactively rotate/pan/zoom and adjust transparency of structures to see behind surface anatomy. To do this, we leverage our experience in building such interfaces for past projects such as systems for planning of deep brain stimulator procedures and systems for planning of image-guided CI drilling systems. Visualization of the patient-specific surgical field-of-view is required so that the plan can be visualized relative to the surgeon's landmarks. To permit this, we also develop a technique for estimating a virtual mastoidectomy surface based on the patient's pre-operative CT. We have recently developed an atlas-based approach to automatically define the mastoid drilling region in pre-op CT for an acoustic neuroma surgical robot [49]. This approach defines a surface that approximates the mastoidectomy and labyrinthectomy drilled by a surgeon in acoustic neuroma surgical approaches. We adapt this technique for CI mastoidectomy to permit simulated visualization preoperatively. FIGS. 15A-15C demonstrate this concept. In FIG. 15A, a microscope view of a patient is shown. In FIG. 15B, we show a virtual view for a different subject that was manually defined with several hours of work in 3D surface editing tools using the subject's pre- and post-implantation CT images. Similar anatomy between the two views is indicated with colored arrows. FIG. 15C shows how the bone hiding the cochlea can be made transparent in the virtual view to permit visualizing the ST and SV surfaces.

Figure 12:
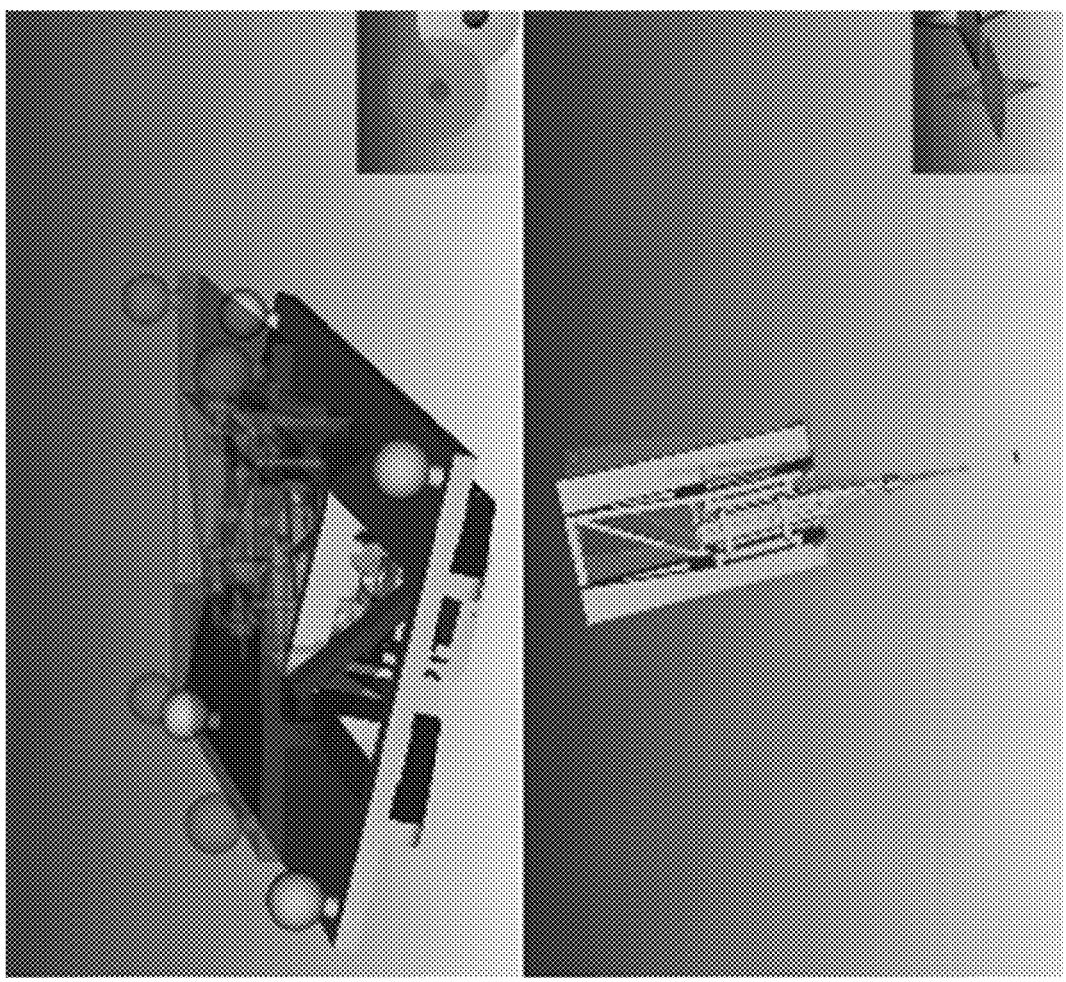
FIG. 12 shows a screenshot of guidance GUI for custom CI drilling procedure with planned position in red and optically tracked position in green, according to one embodiment of the present invention.

Tracker-integrated method: Use of a tracking system during the procedure would provide real-time position feedback to the surgeon and may help to make electrode insertion procedures more effective. In a recent study with simulated surgical field of views, we found that augmenting the surgical field of view with the sub-surface visualization of the ST permitted experienced surgeons to choose better electrode entry sites and entry vectors than when provided surface anatomy alone, suggesting tracked guidance could indeed benefit CI insertion procedures [43]. We use an optical tracker to track the position of the tools used by the surgeon to insert the EA. Our group has experience working with optical trackers and designing marker systems for tracking. When exploring approaches for image-guided drilling of cochlear implant procedures, we have evaluated several optically tracked handheld and robotic drilling solutions [44-46] and developed effective guidance interfaces (FIG. 12). We leverage our existing tools and expertise to design this relatively common guidance configuration. As preliminary work, we have designed a marker system for tracking the forceps used to insert EAs (see FIGS. 13A-13C). This tool was used in an experiment to measure the speed of insertion and involved 11 surgeons performing 104 insertions [58]. We were successful in designing a tracked tool that was effectively usable in the typical surgical workspace and showed average insertion speed across surgeons of 96 mm/min.

Figures 13A, 13B:
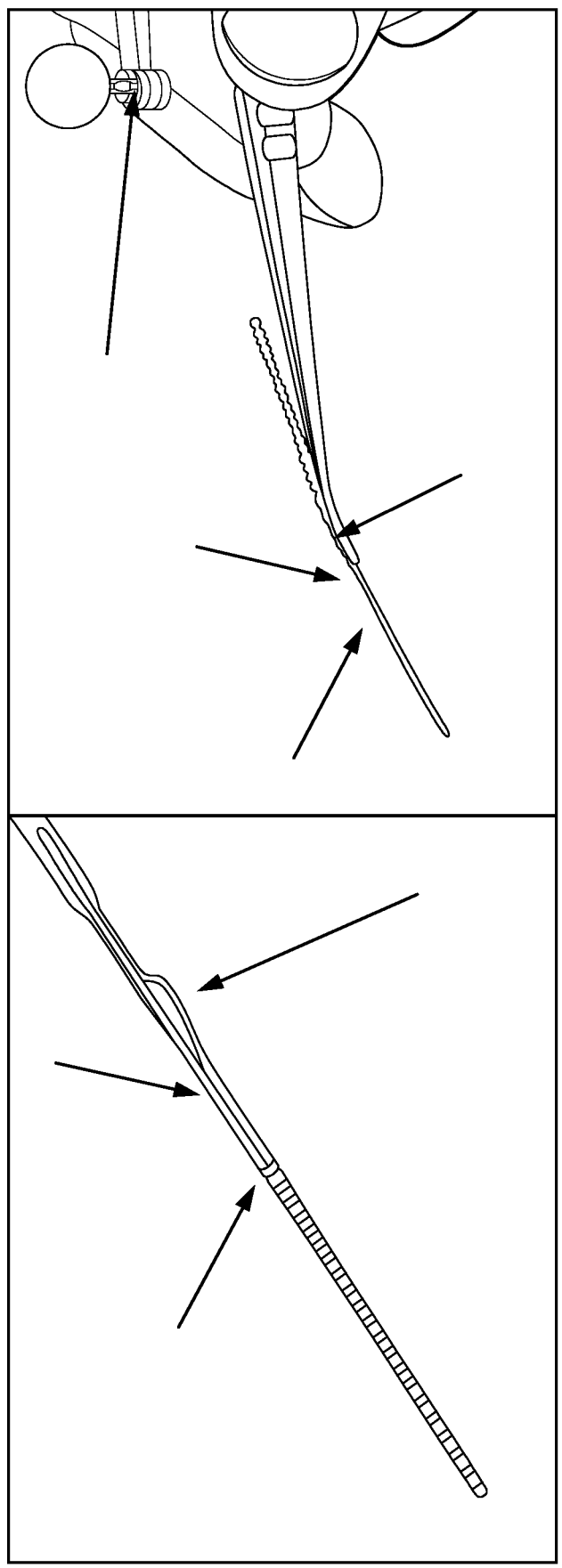
FIGS. 13A-13C show a tracking system used for optimizing cochlear implant electrode insertion, according to one embodiment of the present invention.
Figure 13C:
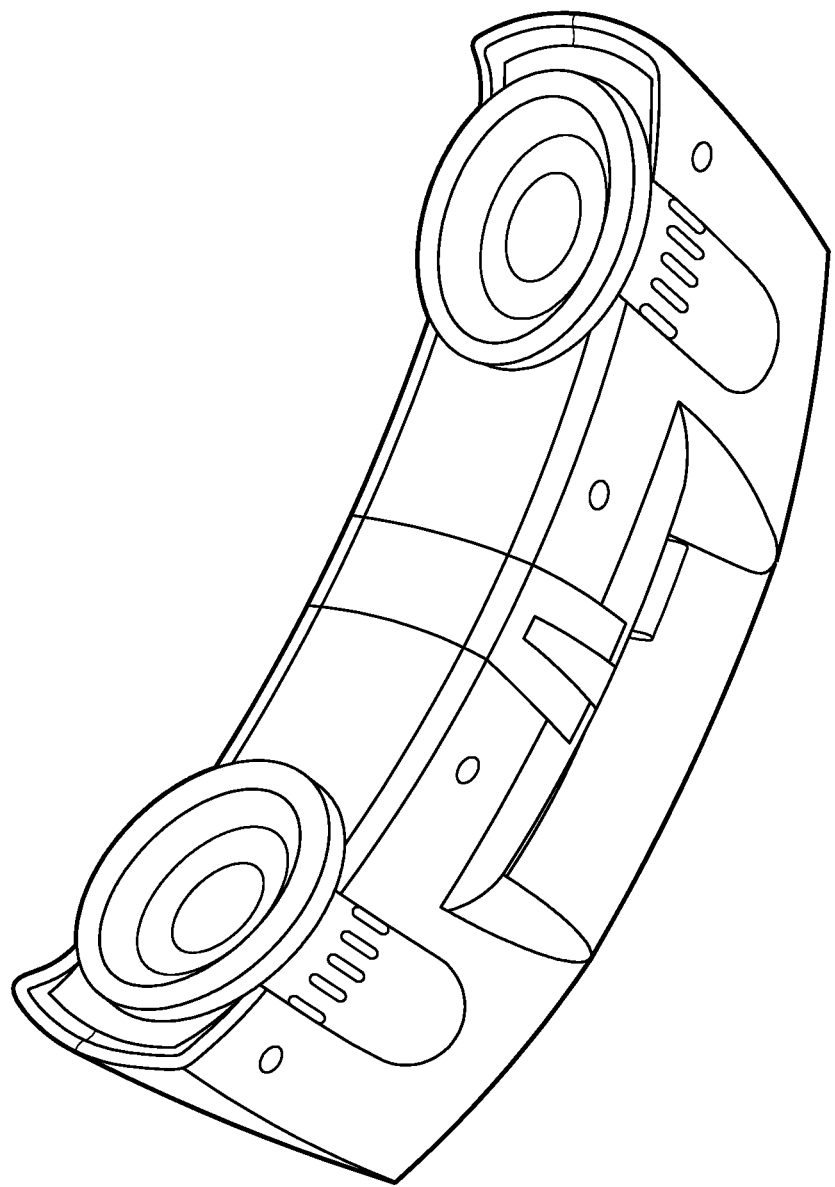

In certain embodiments, the guidance tools and software are disclosed. In certain embodiments, the procedure for use of the tracker is as follows. First, using standard image-guided surgical (IGS) techniques, we place a minimum of 3 bone-implanted markers on each temporal bone with typical locations being the mastoid tip, posterior to the sigmoid sinus, and above the external auditory canal. Such markers may consist of facial plating screws with the cross-hatch on the screw head an identifiable target both in image and physical space. Next, each specimen is CT-scanned and the resultant image registered to the temporal bone using and infrared optical tracker to localize the fiducials in physical space [50]. Once registered, the infrared tracker is used to track the specimen via a coordinate reference frame screwed into the temporal bone and the surgical tools using a similarly affixed frame. Such tools include a probe to mark locations of interest (e.g. location for proposed entry into the cochlea) and forceps used to hold each EA in a repeatable fashion at a fixed position as shown in FIGS. 13A-13C.

In certain embodiments, we develop software that facilitates real-time tracking and provide feedback to the surgeon through a graphical user interface during each step of the insertion procedure. These steps include selection of the entry site using the tracked probe to delineate the starting point and orientation for optimal electrode insertion. Next, the electrode is inserted using the tracked forceps with visual and/or auditory feedback to facilitate staying "on course" of optimal insertion vector and orientation with additional feedback given when AOS depth has been reached and when the terminal insertion depth has been reached. This protocol is consistent with IGS as clinically used with FDA-cleared devices (e.g. Brainlab Curve IGS system). Furthermore, we explore how guidance information is presented as augmented visual overlays onto the surgical microscopic view as shown above in FIG. 15C and how microscope video might be used to improve registration as we have done in other works [52].

NDI has verified the tracker we plan to use has target registration errors under 0.4 mm. Schipper et al. 2005 have shown that the most demanding task for a cochlear implant guidance system, targeting the cochlea entry site, needs TRE<=0.5 mm RMS. Thus, targeting the entry site may be sensitive to tracker errors. If this is found to be the case, we will add the use of our interactive visualization software developed for the tracker-free approach to show the surgeon a visualization of the optimal entry site overlaid on a 3D rendering of the virtual surgical view of the patient's anatomy, similar to the view shown in FIG. 15C. We also investigate ways to use the tracked probe to calibrate the tracker to improve the registration using local anatomical points such as the RW overhang and/or the manubrium of malleus. After entry site, the next most demanding task would be depths of insertion. Our preliminary results with instructing depths of insertion to the surgeon suggest that surgeons are accurate to 0.70 mm and even at that level of error our data show that results with image-guidance represent improvement over traditional techniques. The other quantities we will provide guidance for are entry angles via tracking the orientation of tools. The tracker should be much more accurate (with TRE of 0.4 mm and markers spaced 75 mm apart we estimate worst case scenario error to be <1 degree) than needed in estimating the orientation of a tool.

Evaluation: To measure the effectiveness of our tracker-free and tracker-enabled guidance techniques in influencing surgical approach, the instrument tracking system we proposed will be used to record the surgeon's actions and will facilitate measuring how closely the surgeon is able to follow the recommended plans such as entry site, entry vector, EA orientation, and AOS and terminal depth. Post-implantation μCT imaging will be used to measure compliance with planned base insertion depth. To evaluate how effective the recommended plans are in achieving optimal EA positioning, we plan to have two experienced surgeons implant 16 EAs of both electrode types (pre-curved and straight) in each of three (no guidance-control, tracker-free guidance, tracker-enabled guidance) conditions, totaling 96 insertions. Post-insertion μCT imaging will permit accurate measurement of our outcome metrics. Differences in electrode positioning across conditions will be used to characterize the effectiveness of our proposed electrode insertion guidance techniques. With each N=32 experiment, we will have statistical power over 0.8 to detect ST location rate differences between control experiments (average of 60% as in our preliminary studies) and our experimental group if our experimental rate is at least 90% (was 100% in our preliminary studies). GLMs are used not only to study not only the effect of instructions, but also of surgeon, device type, and guidance conditions, on achieving optimal electrode placement. The significant associations we have already found on a small dataset show the promise of using such techniques on the large dataset we will acquire with 16 cases per condition.

These and other aspects of the present invention are more specifically described below.

In one aspect of the present invention, a method for using information of patient-specific cochlea size and/or shape to determine a patient-customized cochlear implant electrode insertion and placement plan is provided.

Figure 16:
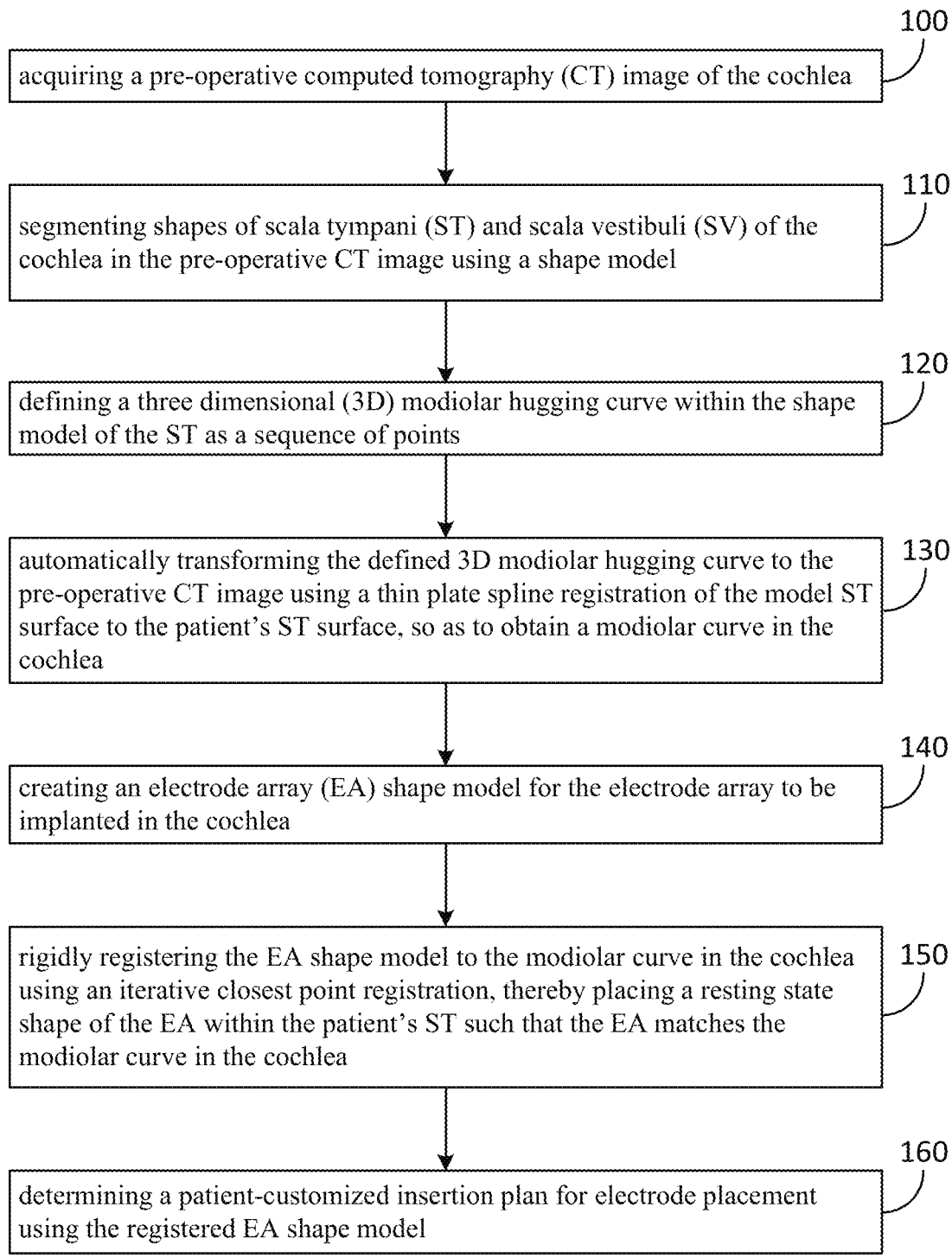
FIG. 16 shows a method for using information of patient-specific cochlea size and/or shape to determine a patient-customized cochlear implant electrode insertion and placement plan, according to one embodiment of the present invention.

Referring to FIG. 16, the method is shown according to one embodiment of the present invention, and includes the following steps.

At step 100, a pre-operative computed tomography (CT) image of the cochlea is acquired.

At step 110, shapes of scala tympani (ST) and scala vestibuli (SV) of the cochlea in the pre-operative CT image are segmented using a shape model.

At step 120, a three dimensional (3D) modiolar hugging curve is defined within the shape model of the ST as a sequence of points.

At step 130, the defined 3D modiolar hugging curve is automatically transformed to the pre-operative CT image using a thin plate spline registration of the model ST surface to the patient's ST surface, so as to obtain a modiolar curve in the cochlea.

At step 140, an electrode array (EA) shape model for the electrode array to be implanted in the cochlea is created.

At step 150, the EA shape model is rigidly registered to the modiolar curve in the cochlea using an iterative closest point registration, thereby placing a resting state shape of the EA within the patient's ST such that the EA matches the modiolar curve in the cochlea.

At step 160, a patient-customized insertion plan for electrode placement is determined using the registered EA shape model. The patient-customized insertion plan comprises a base insertion depth, an advanced off stylet (AOS) depth and a trajectory orientation, and an entry site and an entry vector.

In one embodiment, the method further includes displaying the patient-customized insertion plan in a textual format and/or a visualized format.

In one embodiment, the shape model is a non-rigid statistical shape model created with μCT images of a plurality of cochlea specimens in which intra-cochlear structures are visible. In one embodiment, the shape model can be a rigid shape model or a rigid statistical shape model.

In one embodiment, the segmenting step 110 comprises automatically fitting the non-rigid statistical shape model to an external boundary of the cochlea that is visible in the pre-operative CT, thereby allowing highly accurate estimation of positions and shapes of intra-cochlear structures of the cochlea that are not visible in the pre-operative CT.

In one embodiment, the creating step 140 comprises acquiring a CT image of the EA in air under no load; and measuring the 3D position of each electrode in the EA in the CT image, wherein the EA shape model provides an estimation of the resting state shape of the EA.

In one embodiment, the determining step 160 comprises determining the base insertion depth as the depth of the base of the registered EA shape model.

In one embodiment, the determining step 160 comprises extending the EA shape model of the resting state shape of the EA to be a stylet position-dependent trajectory model of the EA; aligning the stylet position-dependent trajectory model with the cochlear anatomy of the patient with the AOS depth chosen so that the best agreement between the stylet position-dependent trajectory model and the modiolar curve in the cochlea is resulted; and determining the orientation as the orientation of the aligned model that matches the orientation of the basal turn of the ST. In one embodiment, the extending step comprises providing a group of practice EAs undergoing AOS deployment; for each EA, retracting a straightening stylet by an amount in a range from 0 mm to fully retracted, and measuring each retraction distance of the stylet; performing a 3D reconstruction of each of the EAs by localizing the position of each electrode in a CT scan that is acquired of the EA with the stylet at the measured distance of retraction; aligning the 3D reconstruction of each EA such that the tip of the stylet is co-located across EAs, wherein the shape of the EA at the largest retraction amount is equivalent to the final relaxed shape of the EA with no stylet; simulating the shape of the EA at a stylet extraction amount by interpolating a weighted average between shapes, wherein the interpolating comprises treating each EA as a sequence of linear segments attached at joints corresponding to each electrode; and linearly interpolating the joint angles between exemplar EAs, so as to predict interval shapes comprising the trajectory of an EA electrode undergoing AOS; and simulating the trajectory of the EA as it is advanced off the stylet by iteratively estimating the shape of the EA while increasing the amount of stylet retraction from 0 mm to fully retracted. In one embodiment, the retraction distance of the stylet is measured precisely using digital calipers under a microscope.

In one embodiment, the determining step 160 comprises determining a trajectory that is as close as possible to being collinear with the basal turn of the ST while also passing through the facial recess and either an extended round window cochleostomy, or, preferably, directly through the round window, so as to choosing the optimal entry vector and site.

Figure 17:
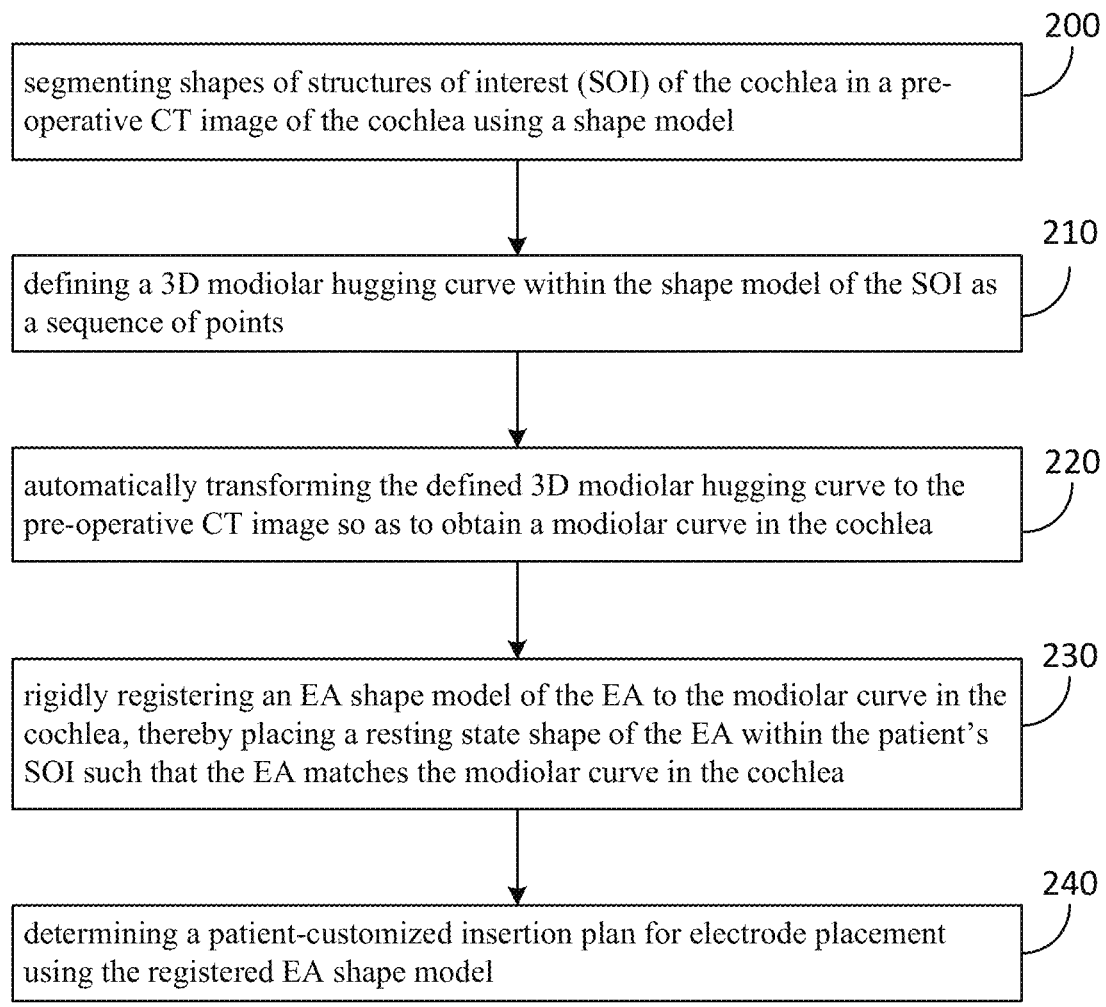
FIG. 17 shows a method for using information of patient-specific cochlea size and/or shape to determine a patient-customized cochlear implant electrode insertion and placement plan, according to another embodiment of the present invention.

In another aspect of the present invention, the method for using information of patient-specific cochlea size and/or shape to determine a patient-customized cochlear implant electrode insertion and placement plan includes the following steps, as shown in FIG. 17.

As step 200, shapes of structures of interest (SOIs) of the cochlea in a pre-operative CT image of the cochlea is segmented using a shape model.

As step 210, a 3D modiolar hugging curve is defined within the shape model of the SOIs as a sequence of points.

As step 220, the defined 3D modiolar hugging curve is automatically transformed to the pre-operative CT image so as to obtain a modiolar curve in the cochlea.

As step 230, an EA shape model of the EA is rigidly registered to the modiolar curve in the cochlea, thereby placing a resting state shape of the EA within the patient's SOIs such that the EA matches the modiolar curve in the cochlea.

As step 240, a patient-customized insertion plan for electrode placement is determined using the registered EA shape model. The patient-customized insertion plan comprises a base insertion depth, an AOS depth and a trajectory orientation, and an entry site and an entry vector.

In one embodiment, the method further comprises displaying the patient-customized insertion plan in a textual format and/or a visualized format.

In one embodiment, the SOIs are temporal bone anatomy.

In one embodiment, the segmenting step 200 comprises automatically fitting the shape model to an external boundary of the cochlea that is visible in the pre-operative CT, thereby allowing highly accurate estimation of positions and shapes of intra-cochlear structures of the cochlea that are not visible in the pre-operative CT.

In one embodiment, the EA shape model is created by acquiring a CT image of the EA in air under no load; and measuring the 3D position of each electrode in the EA in the CT image, wherein the EA shape model provides an estimation of the resting state shape of the EA.

In one embodiment, the automatically transforming step 220 is performed by a thin plate spline registration that registers the model SOIs surface to the patient's SOIs surface.

In one embodiment, the rigidly registering step 230 is performed by an iterative closest point registration.

In one embodiment, the determining step 240 comprises determining the base insertion depth as the depth of the base of the registered EA shape model.

In one embodiment, the determining step 240 comprises extending the EA shape model of the resting state shape of the EA to be a stylet position-dependent trajectory model of the EA; aligning the stylet position-dependent trajectory model with the cochlear anatomy of the patient with the AOS depth chosen so that the best agreement between the stylet position-dependent trajectory model and the modiolar curve in the cochlea is resulted; and determining the orientation as the orientation of the aligned model that matches the orientation of the basal turn of the ST.

In one embodiment, the determining step 240 comprises determining a trajectory that is as close as possible to being collinear with the basal turn of the ST while also passing through the facial recess and either an extended round window cochleostomy, or, preferably, directly through the round window, so as to choosing the optimal entry vector and site.

In one aspect, the invention relates to a method for using information of patient-specific cochlea size and/or shape to determine a patient-customized cochlear implant electrode insertion and placement plan. In one embodiment, the method includes acquiring information of patient-specific cochlear size and/or shape of the cochlea; and determining a patient-customized cochlear implant electrode insertion and placement plan based on the acquired information of the patient-specific cochlear size and/or shape of the cochlea.

In one embodiment, the acquiring step comprises segmenting shapes of SOIs of a cochlea of the patient in a pre-operative CT image of the cochlea using a shape model, wherein the EA is to be placed in the cochlea; defining a 3D curve of interest within the shape model of the SOIs as a sequence of points; and automatically transforming the defined 3D curve to the pre-operative CT image so as to obtain a structure curve in the cochlea, wherein the structure curve in the cochlea contains the information of the patient-specific cochlear size and/or shape.

In one embodiment, the determining step comprises rigidly registering an EA shape model of the EA to the structure curve in the cochlea such that the EA matches the structure curve in the cochlea; and determining the patient-customized cochlear implant electrode insertion and placement plan using the registered EA shape model.

In one embodiment, the SOIs are temporal bone anatomy or a lateral wall in the cochlea.

In one embodiment, the structure curve is a hugging curve or a lateral wall curve in the cochlea.

In yet another aspect of the present invention, a method for intra-operative guidance of electrode insertion procedures of a cochlear implant in a cochlea of a patient includes determining a patient-customized insertion plan of an EA to be implanted in the cochlea, as disclosed above; displaying the patient-customized insertion plan in a textual format and/or a visualized format; and inserting the EA in the cochlea according to the patient-customized insertion plan.

In one embodiment, the method further includes intra-operatively tracking the electrode insertion tool to provide feedback to a surgeon through a graphical user interface during the insertion procedure.

In one embodiment, the inserting step is performed with an electrode insertion tool that is operably fixable relative to the temporal bone of the cochlea.

In a further aspect, the present invention relates to a non-transitory computer-readable medium storing instructions which, when executed by a processor, cause a computer or system to perform a method for using information of patient-specific cochlea size and/or shape to determine a patient-customized cochlear implant electrode insertion and placement plan. In one embodiment, the method is disclosed above and shown in FIG. 17.

In one aspect, the present invention relates to a method for intra-operative guidance of electrode insertion procedures of a cochlear implant in a cochlea of a patient.

Figure 18:
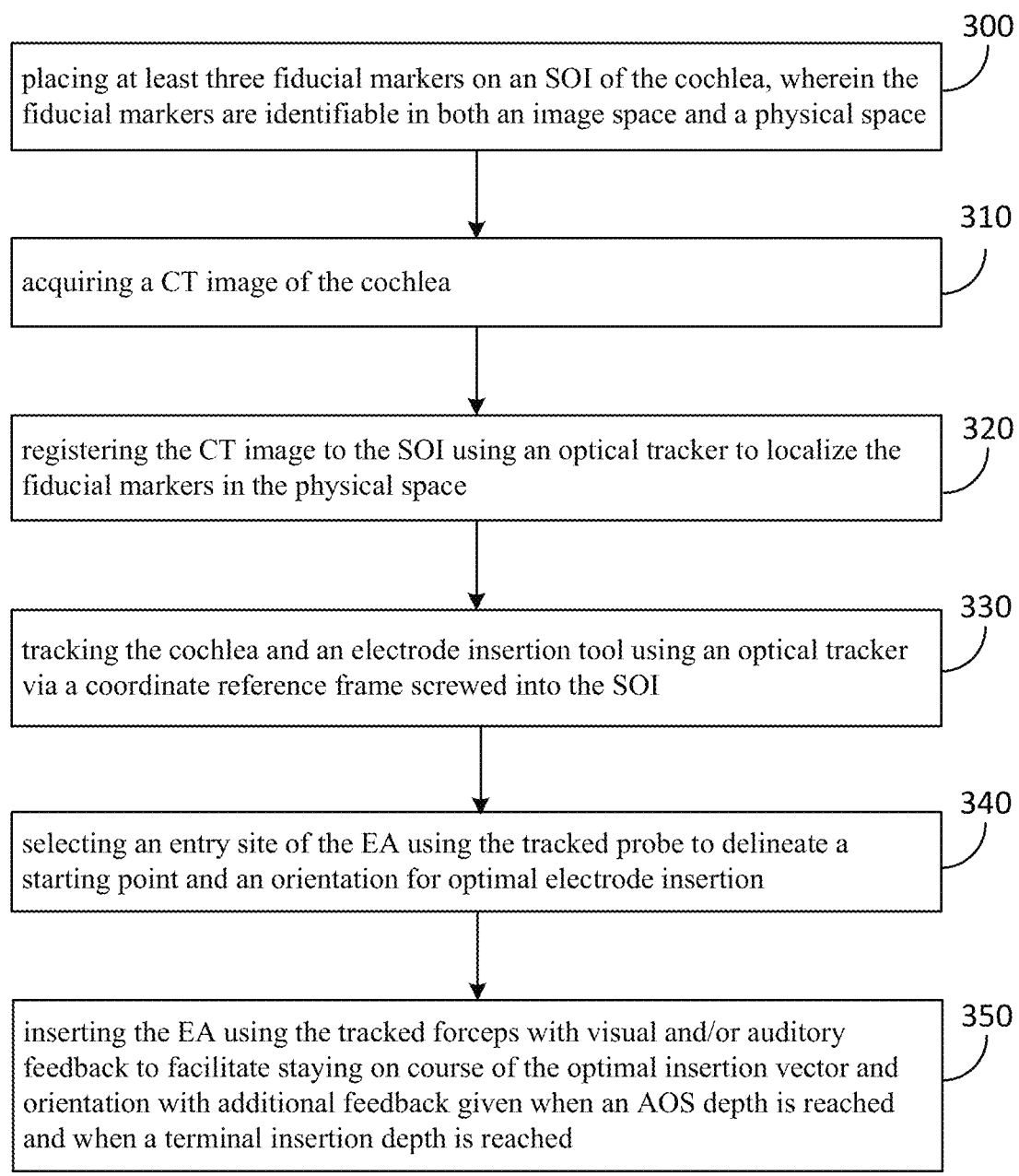
FIG. 18 shows a method for intra-operative guidance of electrode insertion procedures of a cochlear implant in a cochlea of a patient, according to one embodiment of the present invention.

As shown in FIG. 18, in the exemplary embodiment, the method includes the following steps.

At step 300, at least three fiducial markers are placed on SOIs of the cochlea. The fiducial markers are identifiable in both an image space and a physical space. In one embodiment, the fiducial markers comprise bone-implanted markers located the mastoid tip, posterior to the sigmoid sinus, and above the external auditory canal of the cochlea. In one embodiment, the fiducial markers comprise facial plating screws each having a screw head and a cross-hatch on the screw head.

At step 310, a CT image of the cochlea is acquired.

At step 320, the CT image is registered to the SOIs using an optical tracker to localize the fiducial markers in the physical space.

At step 330, the cochlea and an electrode insertion tool are tracked using an optical tracker via a coordinate reference frame screwed into the SOIs. The electrode insertion tool comprises a probe to mark locations of interest and a forceps used to hold an EA in a repeatable fashion at a fixed position. In one embodiment, the locations of interest include a location for a proposed entry of the EA into the cochlea.

At step 340, an entry site of the EA is selected using the tracked probe to delineate a starting point and an orientation for optimal electrode insertion.

At step 350, the EA is inserted using the tracked forceps with visual and/or auditory feedback to facilitate staying on course of the optimal insertion vector and orientation with additional feedback given when an AOS depth is reached and when a terminal insertion depth is reached.

In one embodiment, the method further comprises facilitating real-time tracking to provide feedback to the surgeon through a graphical user interface during each step of the insertion procedure.

In one embodiment, the method further comprises presenting the intra-operative guidance as augmented visual overlays onto a surgical microscopic view.

In another aspect, the present invention relates to a non-transitory computer-readable medium storing instructions which, when executed by a processor, cause a computer or system to perform a method for intra-operative guidance of electrode insertion procedures of a cochlear implant in a cochlea of a patient. In one embodiment, the method is disclosed above and shown in FIG. 18.

In one aspect of the present invention, a system for intra-operative guidance of electrode insertion procedures of a cochlear implant in a cochlea of a patient includes a means for acquiring a CT image of the cochlea. The image acquiring means can be a CT scanner or the likes.

The system also includes an electrode insertion tool comprising a probe configured to mark locations of interest and a forceps used to hold an EA; and an optical tracker configured to localize fiducial markers in a physical space, and track the cochlea and the electrode insertion tool via a coordinate reference frame screwed into SOIs of the cochlea. The fiducial markers are operably placed on the SOIs of the cochlea, and are identifiable in both the image space and the physical space. In one embodiment, the fiducial markers comprise bone-implanted markers located the mastoid tip, posterior to the sigmoid sinus, and above the external auditory canal of the cochlea. In one embodiment, the fiducial markers comprise facial plating screws each having a screw head and a cross-hatch on the screw head. In one embodiment, the locations of interest include a location for a proposed entry of the EA into the cochlea.

In addition, the system also includes a microcontroller coupled with the acquiring means, the electrode insertion tool and the optical tracker, and configured to register the CT image to the SOIs of the cochlea; select an entry site of the EA for optimal electrode insertion; and provide, during the insertion procedure, visual and/or auditory feedback to facilitate staying on course of the optimal insertion vector and orientation with additional feedback given when an AOS depth is reached and when a terminal insertion depth is reached. The microcontroller includes one or more processors, and can be a computer or the likes.

In one embodiment, the system further comprises a display for real-time tracking to provide feedback to the surgeon through a graphical user interface during the insertion procedure.

In one embodiment, the system further comprises an augmented visual overlay to present the intra-operative guidance onto a surgical microscopic view.

In one aspect, the present invention relates to a method for designing a patient-customized EA or selecting an existing EA that fits the patient best, based on information of the patient-specific cochlea size and/or shape.

Figure 19:
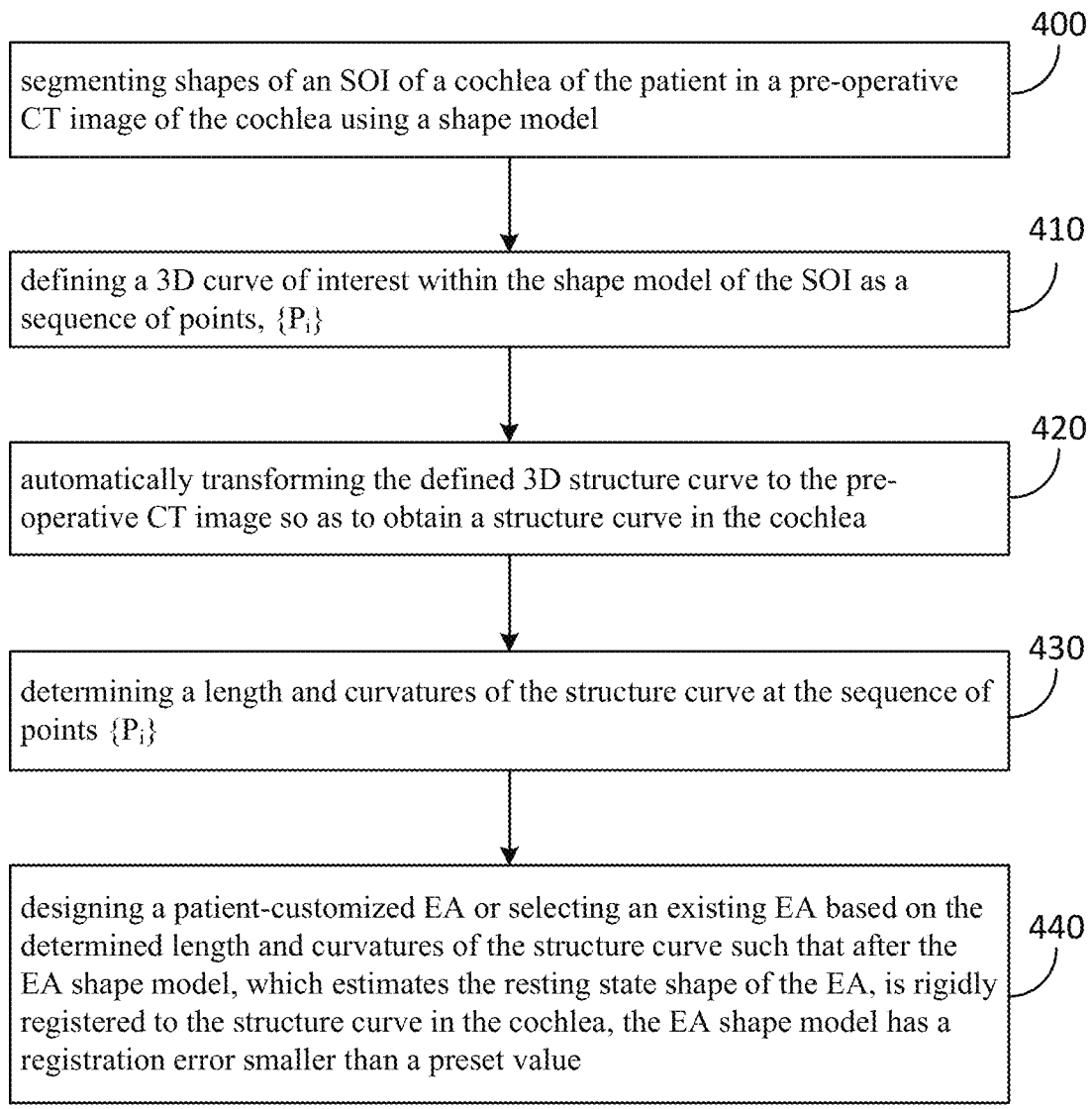
FIG. 19 shows a method for designing a patient-customized electrode array (EA) or selecting an existing EA that fits the patient best, according to one embodiment of the present invention.

As shown in FIG. 19, in the exemplary embodiment, the method includes the following steps.

At step 400, shapes of SOIs of a cochlea of the patient in a pre-operative CT image of the cochlea is segmented using a shape model. The EA is to be placed in the cochlea.

Figure 20:
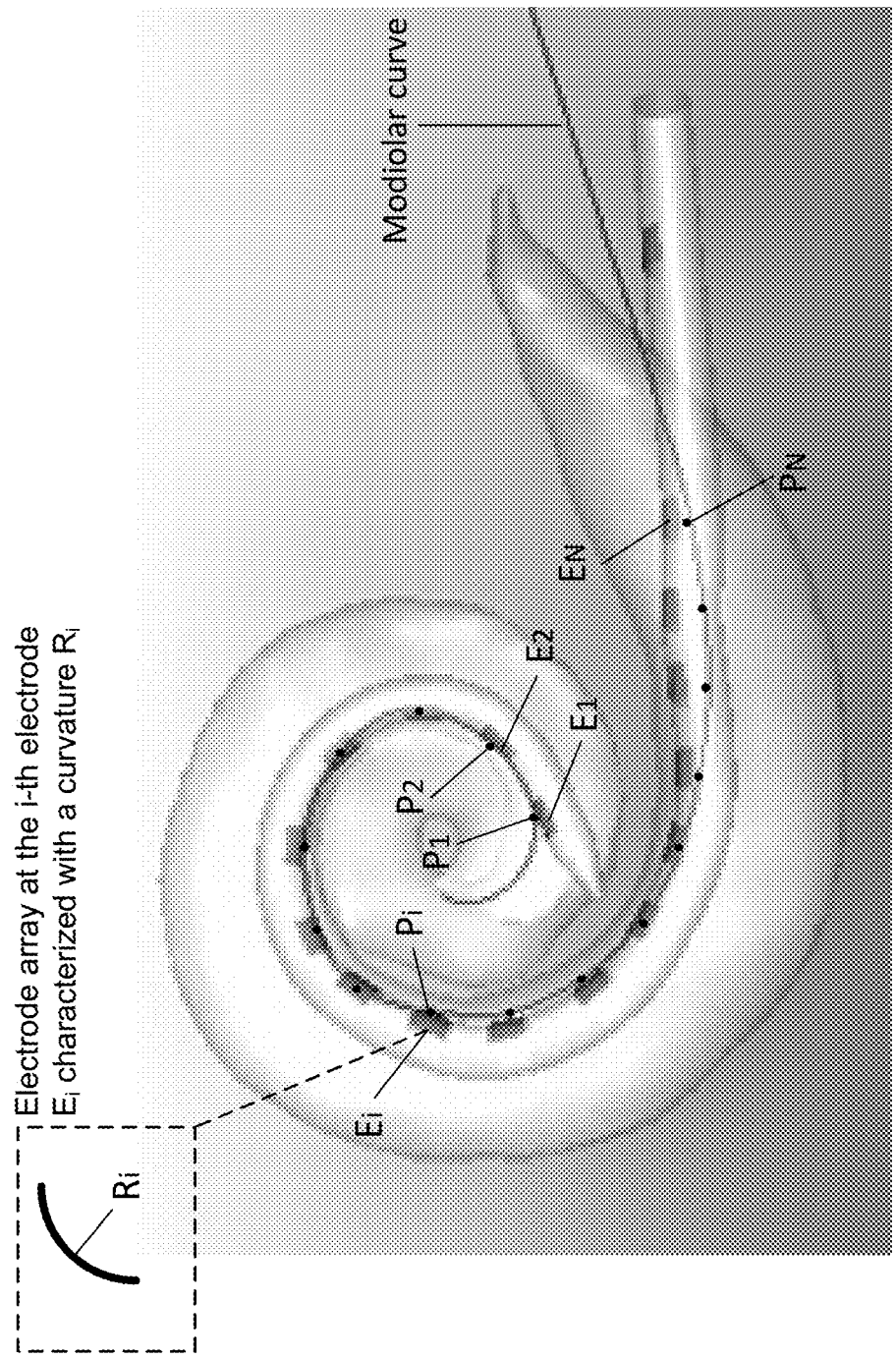
FIG. 20 shows a patient-customized EA and its insertion in a cochlea of a patient, according to one embodiment of the present invention.

At step 410, a 3D curve of interest is defined within the shape model of the SOIs as a sequence of points, $\{P_i\}$, where $i=1, 2, 3, \ldots N$, N is an integer greater than zero, as shown in FIG. 20.

At step 420, the defined 3D structure curve is automatically transformed to the pre-operative CT image so as to obtain a structure curve (e.g., modiolar curve shown in FIG. 20) in the cochlea.

At step 430, a length and curvatures of the structure curve at the sequence of points $\{P_i\}$ are determined.

At step 440, a patient-customized EA is designed or an existing EA selected, based on the determined length and curvatures of the structure curve such that after the EA shape model, which estimates the resting state shape of the EA, is rigidly registered to the structure curve in the cochlea, the EA shape model has a registration error smaller than a preset value.

In one embodiment, the method further comprises determining a patient-customized insertion plan for electrode insertion using the registered EA shape model. The patient-customized insertion plan comprises at least a recommended depth.

As shown in FIG. 20, in one embodiment, the EA comprises a plurality of electrodes, $\{E_i\}$, where the i-th electrode $E_i$ is to be placed in a location corresponding to the i-th point $P_i$ of the structure curve in the cochlea, where $i=1, 2, 3, \ldots N$, N is an integer greater than zero.

In one embodiment, the curvature of the EA at the i-th electrode $E_i$ is characterized with a curvature that matches the curvature of the i-th point $P_i$ of the structure curve in the cochlea.

In one embodiment, the i-th electrode $E_i$ is a flat electrode, or a curved electrode that is characterized with a curvature that matches the curvature of the i-th point $P_i$ of the structure curve in the cochlea.

In one embodiment, the structure curve t is a modiolar curve in the cochlea, and wherein the EA is a pre-curved EA.

In one embodiment, the structure curve is a lateral wall curve in the cochlea, and wherein the EA is a straight EA.

In one embodiment, the straight EA has a length determined such that when placed along the lateral wall curve, an angular insertion depth of the distal electrode reaches about 500°, while a proximal electrode falls safely within the cochlea being greater than 30°.

In one embodiment, the SOIs are temporal bone anatomy.

In one embodiment, the SOIs are intra-cochlear structures

In one embodiment, the defined 3D structure curve is automatically transformed to the pre-operative CT image using a thin plate spline registration.

In one embodiment, the EA shape model is rigidly registered to the structure curve in the cochlea using an iterative closest point registration, thereby placing the resting state shape of the EA within the SOIs in the cochlea such that the EA matches the structure curve in the cochlea.

In one embodiment, when inserted, the base depth of electrode insertion of the EA matches the recommended depth.

In one aspect, the invention relates to a method for designing a patient-customized EA or selecting an existing EA that fits the patient best, based on information of the patient-specific cochlea size and/or shape. In In one embodiment, the method comprises acquiring information of the patient-specific cochlear size and/or shape of the cochlea; and designing a patient-customized EA or selecting an existing EA based on the acquired information of the patient-specific cochlear size and/or shape of the cochlea.

In one embodiment, the acquiring step comprises segmenting shapes of SOIs of a cochlea of the patient in a pre-operative CT image of the cochlea using a shape model, wherein the EA is to be placed in the cochlea; defining a 3D curve of interest within the shape model of the SOIs as a sequence of points, $\{P_i\}$, wherein $i=1, 2, 3, \ldots N$, N is an integer greater than zero; automatically transforming the defined 3D curve to the pre-operative CT image so as to obtain a structure curve in the cochlea; and determining a length and curvatures of the structure curve at the sequence of points $\{P_i\}$.

In one embodiment, the selecting/designing step comprises designing a patient-customized EA or selecting an existing EA based on the determined length and curvatures of the structure curve in cochlea, such that after the EA shape model, which estimates the resting state shape of the EA, is rigidly registered to the structure curve in the cochlea, the EA shape model has a registration error smaller than a preset value.

In one embodiment, the SOIs are temporal bone anatomy.

In one embodiment, the structure curve is a modiolar curve or a lateral wall curve in the cochlea.

In one aspect, the present invention relates to a non-transitory computer-readable medium storing instructions which, when executed by a processor, cause a computer or system to perform a method for selecting/designing a patient-customized EA that works best for an individual patient. In one embodiment, the method is disclosed above and shown in FIGS. 19-20.

In another aspect, the present invention relates to a patient-customized EA, comprising a plurality of electrodes, $\{E_i\}$, assembled in a pre-curved form, where the curvature of the EA at the i-th electrode $E_i$ is characterized with a curvature that matches the curvature of the i-th point $P_i$ of the structure curve in the cochlea of a patient where the i-th electrode $E_i$ is to be placed, wherein i=1, 2, 3, ... N, N is an integer greater than zero.

In one embodiment, the structure curve is a modiolar curve in the cochlea.

It should be noted that all or a part of the steps according to the embodiments of the present invention is implemented by hardware or a program instructing relevant hardware. Yet another aspect of the invention provides a non-transitory computer readable storage medium/memory which stores computer executable instructions or program codes. The computer executable instructions or program codes enable a computer or a similar computing system to complete various operations in the above disclosed method for privilege management. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

Without intent to limit the scope of the invention, examples and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE

Preliminary Results with Image-Guided Cochlear Implant Insertion Techniques

In this exemplary example, we present preliminary results from a blinded, randomized temporal bone study comparing final EA position for *cochleae* implanted with customized optimal insertion plans versus suboptimal insertion plans.
Methods According to the invention, analysis of temporal bone anatomy, i.e., the shape of ST and SV, in the pre-operative CT image can be used to recommend an approach vector, array base insertion depth, and AOS depth and orientation for pre-curved EAs. To segment ST and SV, we use a shape model such as a non-rigid statistical shape model [27] created with μCT images of 9 *cochleae* specimens in which intra-cochlear structures are visible [11-12]. These models are then automatically fit to the external boundary of the patient cochlea that is visible in conventional CT allowing highly accurate estimation of the position of internal cochlear structures not visible in the CT. FIGS. 21A-21C show a portion of a pre-operative CT scan and the results obtained with our segmentations presented as 3D surfaces and 2D contours.

To make recommendations for the insertion procedure, we expand upon a technique proposed to estimate the optimal final position of the electrode array (EA) for a patient based on their cochlear shape [33]. First, an EA shape model is created. While our methods could apply to any pre-curved array, in this example we chose to use the Advance Bionics Mid-Scala (MS) array due to the availability of practice arrays for use in this study. The model is created by acquiring a CT image of the EA in air under no load and measuring the 3D position of each electrode in the array in the image. This provides an estimation of the resting state shape of the array. Next, to define the ideal modiolar position of the array for a new patient, the ideal modiolar position of ST is localized in our statistical shape model that we use to localize intra-cochlear anatomy. This was done by manually defining a 3D modiolar hugging curve as a sequence of points within the statistical shape model of the ST using 3D object editing software developed in-house. This manually defined modiolar hugging curve is automatically transformed to each patient's pre-implant CT using a Thin Plate Spline registration [35] of the model ST surface to the patient's ST surface. The result of this process is shown as the blue curve in FIG. 21D. Finally, the EA shape model is rigidly registered to the patient's modiolar curve using an iterative closest point registration technique [37] which places the resting state shape of the EA within the patient's ST such that the EA best matches the patient's modiolar curve as shown in FIG. 21D, which depicts the EA shape model (green) after registration to the modiolar curve (blue). This registered EA shape model is used to determine patient-customized insertion plans specifying (i) overall insertion depth, (ii) AOS insertion depth, and (iii) trajectory orientation as described below.

Figures 23A, 23B, 23C:
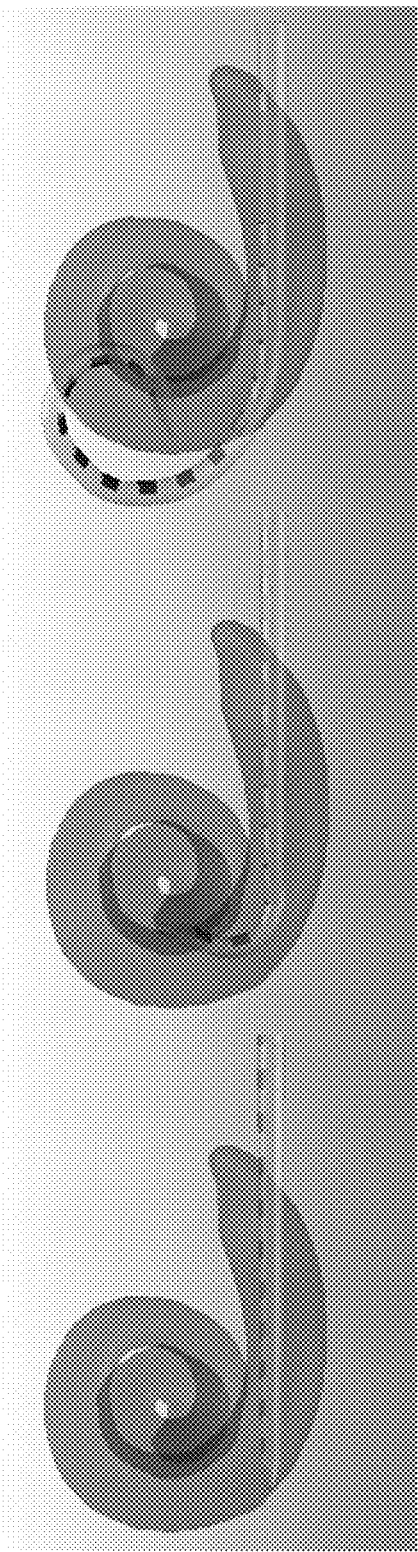
FIGS. 23A-23C show shape of the array as it is advanced off the stylet using the control plan AOS and insertion depths for case No. 12. The resting state shape of the array are shown when it is advanced 0 mm (FIG. 23A) and 2 mm (FIG. 23B) off the stylet with the stylet at a depth of 7 mm and, in (c), once full insertion depth is reached and the stylet is fully retracted (FIG. 23C).

To determine overall insertion depth, we use the technique described by Wang et al. [33] to specify where the base marker should be placed relative to the entry into the cochlea (e.g. in FIG. 21D, the depth is specified as 2 mm outside of the cochlea). To determine the depth at which AOS is to begin, we combine the resting state shape of the array with the stylet position-dependent trajectory model proposed by McBrayer et al. [23]. To do this, a group of 9 practice MS arrays underwent AOS deployment in increments of approximately 2 mm (exact distance of stylet withdrawn was measured precisely using digital calipers under a microscope) with 3D reconstruction at each interval of deployment facilitated by CT scanning. Three interval results of this process are shown in FIGS. 23A-23C, superimposed onto a patient's cochlea. The last panel corresponds to the shape of the array with the stylet fully withdrawn (i.e. the resting state shape). Using these 9 exemplars, we can simulate the shape of the array at any AOS distance by interpolating a weighted average between shapes. For interpolation we treat each EA as a sequence of linear segments attached at joints corresponding to each electrode. To predict interval shapes comprising the trajectory of an EA electrode undergoing AOS, we linearly interpolate the joint angles between exemplar arrays. Applying this model to the generically recommended AOS depth, agreement between the EA trajectory and the modiolar curve was found to average approximately 0.5 mm [39]. To determine each patient-customized AOS depth, this model was aligned with the individualized cochlear anatomy with AOS depth chosen as that which resulted in the best agreement between the model and modiolar curve (see FIG. 21D). Finally, recommended orientation is chosen as the orientation of the aligned model, which matches the orientation of the basal turn of the ST.

Choosing the best entry vector and site is done by determining a trajectory that is as close as possible to being collinear with the basal turn of the ST while also passing through the facial recess and either an extended round window cochleostomy, or, preferably, directly through the round window. An example of an optimal array entry vector (yellow cylinder) with the structures of interest, which are automatically segmented in pre-operative CT using previously published techniques [40, 41], is shown in FIG. 21E. In this case, the optimal entry vector that is collinear with the base of the ST passes directly adjacent to the facial nerve through an extended RW entry site of the ST, thus this would be the recommended entry vector and site for this case.

We evaluated our approach using a set of 20 temporal bone specimens. Each specimen underwent CT scanning using clinically applicable protocols. After performing a mastoidectomy and posterior tympanotomy, each specimen was implanted by an experienced surgeon. The specimens were randomly divided into two groups (A and B). For each specimen in group A, using the pre-operative CT scan, an optimized plan was generated as proposed above. Group B served as the control group with a realistic plan but predicted by our process to lead to poor electrode placement. The surgeon was blinded regarding which group an individual specimen was randomized into.

A quantitative summary of the instructions for each case are included as Table 2. For each case in the table, shown are whether it belongs to the proposed method (A) or control (B) group, the angle between the orientation of the basal turn and the proposed entry trajectory in both superior-inferior (S-I) and anterior-posterior (A-P) directions, and the orientation of the electrodes relative to orientation of the basal turn. These angular measurements are visualized in FIG. 21E. Also shown in Table 2 are the recommended entry approach of either round window (RW) or extended round window (ERW), the recommended depth to initial AOS relative to the generically recommended AOS depth, and the recommended overall insertion depth relative to the generically recommended insertion depth. To show how different the control plan AOS and insertion depths are from what the plan using the proposed approach would be for these cases, also shown for the control cases are the optimal AOS and overall depth of insertions determined by our proposed techniques. For cases 1-10, we had not yet implemented the image-guided recommendation for the electrode orientation relative to the basal turn orientation, and thus this column is empty. Visualizations of the EA model projected onto the ST for a control case (No. 12) are shown in FIGS. 23A-23C. As can be seen in the figure, for this case using the electrode trajectory model, a good AOS depth and sub-optimal overall depth were chosen for the control plan. Further, as shown in Table 2, the entry vector was deviated from the optimal approach in this case. Group B plans such as this one were designed such that they disagree with the optimized plan in one or more quantities, but have an entry vector that falls within the range of typical entry vectors and have insertions depths that vary closely around the generically recommended depths.

TABLE 2

Quantitative summary of image-guided insertion instructions for each case

| Case | Group | Basal Turn Trajectory: S-I ( ) | Basal Turn Trajectory: A-P ( ) | Basal Turn Rotation ( ) | Entry point | AOS Depth (mm) | Optimal AOS Depth | Overall Depth (mm) | Optimal Overall Depth (mm) |
|---|---|---|---|---|---|---|---|---|---|
| 1 | B | 10.4 | 15.4 | — | ERW | −0.5 | 1.5 | 0.5 | −1.5 |
| 2 | A | | | — | ERW | 1.5 | | −0.5 | |
| 3 | B | 15.5 | 12.9 | — | RW | 2.5 | 1 | 0 | −1.5 |
| 4 | A | | | — | ERW | 1.5 | | −2 | |
| 5 | B | 0 | 0 | — | ERW | 0 | 0.5 | 0 | −3 |
| 6 | A | | | — | RW | 1.5 | | −0.5 | |
| 7 | B | 11.85 | 4.14 | — | RW | −0.5 | 1.5 | 0 | −2 |
| 8 | A | | | — | ERW | 1.5 | | −2.5 | |
| 9 | B | 10.9 | 17.4 | — | RW | 0 | 1.5 | 0 | −1.5 |
| 10 | A | | | — | ERW | 1.5 | | −2.5 | |
| 11 | B | 0.8 | 7.6 | 10.3 | RW | 0 | 0.5 | 0 | −3 |
| 12 | B | 6.87 | 8.8 | 9.59 | RW | 0 | 0.5 | 0 | −3 |
| 13 | A | | | | ERW | 2.5 | | −1 | |
| 14 | A | | | | ERW | 0 | | −2.5 | |
| 15 | A | | | | ERW | 1.5 | | −2.5 | |
| 16 | B | 0.9 | 10.1 | 0 | RW | 0 | 2.5 | −0.5 | −1 |
| 17 | A | | | | ERW | 0.5 | | −2.5 | |
| 18 | A | | | | RW | 1.5 | | −2.5 | |
| 19 | B | 0.8 | 15.5 | −4.9 | RW | 2.5 | 1 | −1 | −3 |
| 20 | B | 1.2 | 5.4 | 21.5 | RW | −0.5 | 1 | −0.5 | −2.5 |

The surgeon was presented the insertion plan in textual format. For the sake of simplicity and so that it was feasible for the surgeon to implement the plan, we converted the specific insertion vector angle quantities and electrode insertion depths into relatively coarse instructions related to reference structures that could be directly visualized. For example, one plan (case 12) was:

Entry site: Insert through the RW membrane.
Entry vector: Choose entry angle to pass through the middle of the facial recess. Face electrodes between the stapes footplate and IS-joint.
AOS depth: Insert array on stylet until the AOS marker is 1.5 mm inside the round window and electrode 7 is even with the RW.
Base insertion depth: Advance off the static stylet until proximal insertion depth marker reaches the round window.

The instructions for all cases were selected such that they were coarse enough that they were easy to implement. For example, the posterior-anterior angle of the entry vector could hug the anterior wall, posterior wall, or pass through the middle of the facial recess, and the superior-inferior angle of the entry vector could either pass 1 mm inferior to the stapes, through the middle of the facial recess, or hug the inferior portion of the facial recess. After implantation, a post-implantation CT was acquired to evaluate electrode position using automated techniques that have been previously developed [15, 16]. Outcome measures included scalar location, modiolar distance, angular insertion depth, and base insertion depth.

In addition to the temporal bone dataset, with IRB approval we also used our image analysis techniques to retrospectively determine the same electrode position outcome measures in CT images from a group of 17 patients who have been implanted with MS arrays at our center. Outcomes measured in this dataset serve as a clinical baseline to be compared to outcomes in our A and B groups.

Results

The image processing computations for each case required approximately 2 minutes to execute on a standard PC. The results for each individual case in our study are shown in Table 3. In the table, shown are the group, resulting scalar location ("ST" for full ST placement versus "ST-SV" for arrays that translocate from ST into SV), angular depth of insertion in degrees, the average distance of the electrodes to the modiolus (Mean Modiolar Dist), and the overall depth of insertion measured as the signed distance between the depth marker and the round window, with negative distances indicating extracochlear placement of the depth marker. Electrode position was measured using automated techniques [15, 16] in postoperative CT scans and confirmed visually using high resolution µCTs for each specimen. Optimal outcome would be scalar location within the ST with high angular depth of insertion, small modiolar distance, and good agreement between the actual and planned overall insertion depth. Overall statistics are shown in Table 1. Also shown in the table are the results from the group of 17 actual patients (Pat) who have been implanted with MS arrays at our center. Two-tailed rank sum tests were used to assess statistical differences in the rate of scalar location among the different groups. Unpaired two-tailed t-tests were used to assess statistical differences in angular depth, modiolar distance, and agreement between the actual and planned insertion depth of the base of the array. As shown in Table 1, no statistically significant differences were detected between the control and patient groups, implying that our control test instructions and results were not dissimilar to traditional surgical techniques.

TABLE 3

Experimental Results for Each Case

| Case | Group | Scalar Location | Angular Depth (°) | Mean Modiolar Dist (mm) | Actual Overall Depth (mm) | \|Actual-Plan Depth\| (mm) |
|---|---|---|---|---|---|---|
| 1 | B | ST-SV | 276 | 0.86 | −1 | 1.5 |
| 2 | A | ST | 383 | 0.51 | 0 | 0.5 |
| 3 | B | ST-SV | 406 | 0.62 | 0 | 0 |
| 4 | A | ST | 367 | 0.41 | −2.1 | 0.1 |
| 5 | B | ST | 378 | 0.61 | −1.5 | 1.5 |
| 6 | A | ST | 382 | 0.49 | 0 | 0.5 |
| 7 | B | ST-SV | 406 | 0.75 | 0 | 0 |
| 8 | A | ST | 356 | 0.63 | −2.6 | 0.1 |
| 9 | B | ST | 375 | 0.44 | −0.8 | 0.8 |
| 10 | A | ST | 359 | 0.61 | −4 | 1.5 |
| 11 | B | ST | 404 | 0.54 | 0 | 0 |
| 12 | B | ST-SV | 388 | 0.75 | −0.9 | 0.9 |
| 13 | A | ST | 362 | 0.43 | −2.1 | 1.1 |
| 14 | A | ST | 352 | 0.61 | −2.9 | 0.4 |
| 15 | A | ST | 358 | 0.48 | −2.5 | 0 |
| 16 | B | ST | 373 | 0.37 | −1.4 | 0.9 |
| 17 | A | ST | 327 | 0.52 | −5.4 | 2.9 |
| 18 | A | ST | 375 | 0.37 | −2.8 | 0.3 |
| 19 | B | ST | 383 | 0.49 | −1.3 | 0.3 |
| 20 | B | ST | 372 | 0.56 | −1.2 | 0.7 |

Our patient-customized insertion plans, Group A, resulted in full ST placement in every case, which was a statistically significantly higher rate of full ST placement than the control tests, Group B, and the patient cases. Statistically significant differences were not detected in angular insertion depth nor in the difference between the actual and the planned base insertion depth. Thus, adherence to the planned base insertion depth was good. The exception is case 17, where under-insertion occurred. This was the only case resulting in extra-cochlear electrodes (E15-E16). It is unknown whether this array was under-inserted initially or backed out after the insertion procedure due to suboptimal fixation. Overall mean modiolar distance was reduced with group A plans, but this difference was not found to be statistically significant in this relatively small study with N=10 samples in each A and B group. Based on our current dataset, we estimate an N=24 study would provide power of 0.8 to detect a significant difference.

Figure 24:
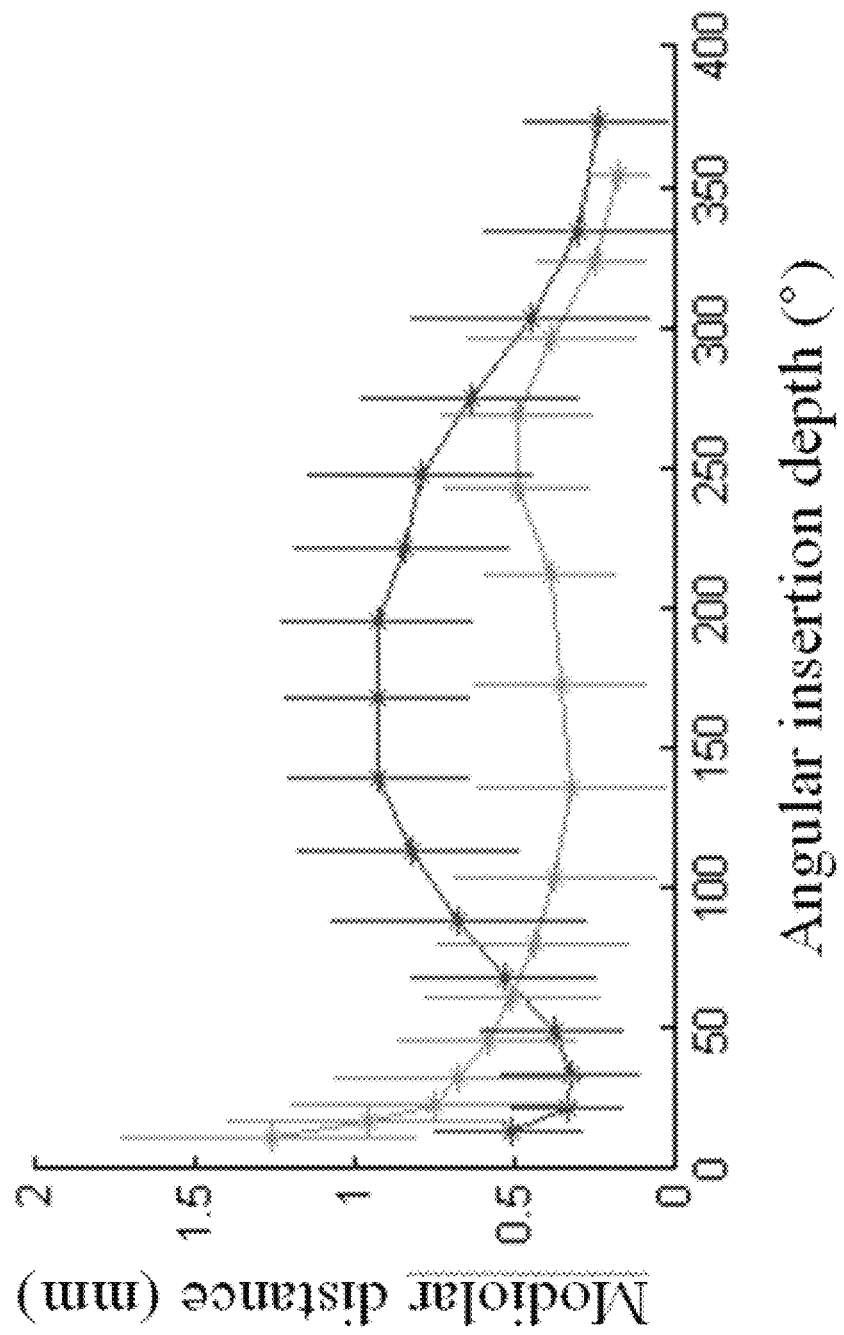
FIG. 24 shows average modiolar distance and insertion depth for each electrode in the A (green) and B (red) groups. Vertical lines indicate standard deviation of modiolar distance.

To show differences on an electrode-by-electrode basis, FIG. 24 depicts the average modiolar distance for each of the 16 electrodes at their average angular insertion depth for the control, Group B, (red) and patient-customized, Group A, (green) cases. The vertical lines in the figure represent the standard deviation of the modiolar distance for each electrode. This plot shows that on average across the control experiments, the middle portion of the array is lifted away from the modiolus, even though the insertion depth marker was not advanced past the round window for any case. The group A plans are more perimodiolar for the middle and apical portions of the array while sacrificing some modiolar proximity at the base of the array. Two sample, two-tailed t-tests with unequal variance were performed for each electrode individually across the A and B groups. After Bonferroni correction for multiple comparisons, it was found that the group A plans resulted in significantly lower modiolar distance for E6-E9 and significantly higher distance for E15-E16. This can be visually appreciated in three-dimensional renderings of representative group A and B cases shown in FIGS. 22A-22D. As can be seen in the figure, the middle portion of the array in the control case 3 (FIGS. 22A-22B) lifts away from the modiolus, whereas the array in the group A case 18 (FIGS. 22C-22D) is perimodiolar.

General linear models were used to detect which guidance quantities, if any, were significantly associated with the final scalar location, angular depth, and mean modiolar distances. We found scalar translocation to be significantly associated with disagreement between the planned and optimal basal turn trajectory superior-inferior angle (r=0.83; p=6e-4). Mean modiolar distance was associated with differences between optimal and planned base insertion depth, entry point, and basal turn trajectory superior-inferior angle (r=0.77; p=2e-3). Overall angular depth was associated with differences between planned and optimal entry point and basal turn trajectory anterior-posterior angle (r=0.72; p=2e-3).

Discussions

Health care is rapidly entering the era of personalized medicine, also known as precision medicine, in which treatment modalities are tailored to individual patient attributes. First applied to pharmacogenetics (i.e. selecting drugs based on genetic traits), it is also true for devices particularly with skeletal implants (e.g. craniofacial reconstructions, joint replacements). Within the field of cochlear implantation, we have yet to enter this new era and continue to use universal sized electrodes to fit all cochlea despite evidence that the cochlea exhibits large inter-patient variability (Hardy, 1938). The excellent average postoperative word and sentence recognition scores of approximately 60% and 70% correct, respectively, achieved with the standard-of-care approach are widely attributable to the plasticity of the central nervous system adapting to the electrical input, yet better matching of CI EA's to the anatomy via a personalized approach has promise of leading to even better potential performance.

For this first implementation of a patient-customized, image-guided insertion plan, we developed a strategy for conveying insertion plans without the use of intra-operative tracking in an effort to facilitate clinical adoption. All of the surgical technique recommendations were provided to the surgeon in the form of textual instructions that referenced anatomical landmarks. Our initial findings (Table 3) indicate that the implanting surgeon could follow these instructions well routinely achieving excellent matching of the proposed insertion depth with the measured insertion depth (range 0-1.5 mm, average=0.7 mm, median=1.1 mm, mode=0 mm) excluding an outlier of 2.9 mm thought to have occurred secondary to migration before adequate fixation.

Our findings confirm that generic insertion plans tend to lead to over-insertion accompanied by buckling of the EA away from the modiolus and against the lateral wall. Once the base of the array has been inserted to the recommended depth, it is likely that the array has returned to its resting shape and the tip of the array has reached the desired angular insertion depth with any further insertion not leading to further advancement of the tip. A clinical example case where this has likely occurred is shown in FIG. 22A where the basal depth marker was inserted about 2 mm past the recommended depth. Advancement of the base of the array beyond the recommend depth resulted in the lateral displacement of the EA away from the modiolar wall in the mid region. On the other hand, inserting the base of the array shallower than the recommended depth may lead to shallower depth of the tip of the array, which also could be detrimental to outcome as the range of nerves stimulated may be reduced.

A potential drawback of our approach which tends to recommend shallower insertion depths is that the most basal electrodes (e.g., E15, E16) are more distant from the modiolus (FIG. 24). However, these electrodes could be deactivated with recent research studies supporting improvement in outcomes with deactivation of suboptimally positioned electrodes [19-21]. We hypothesize that the benefits of better perimodiolar positioning of the rest of the array will outweigh this potential drawback.

Figure 25:
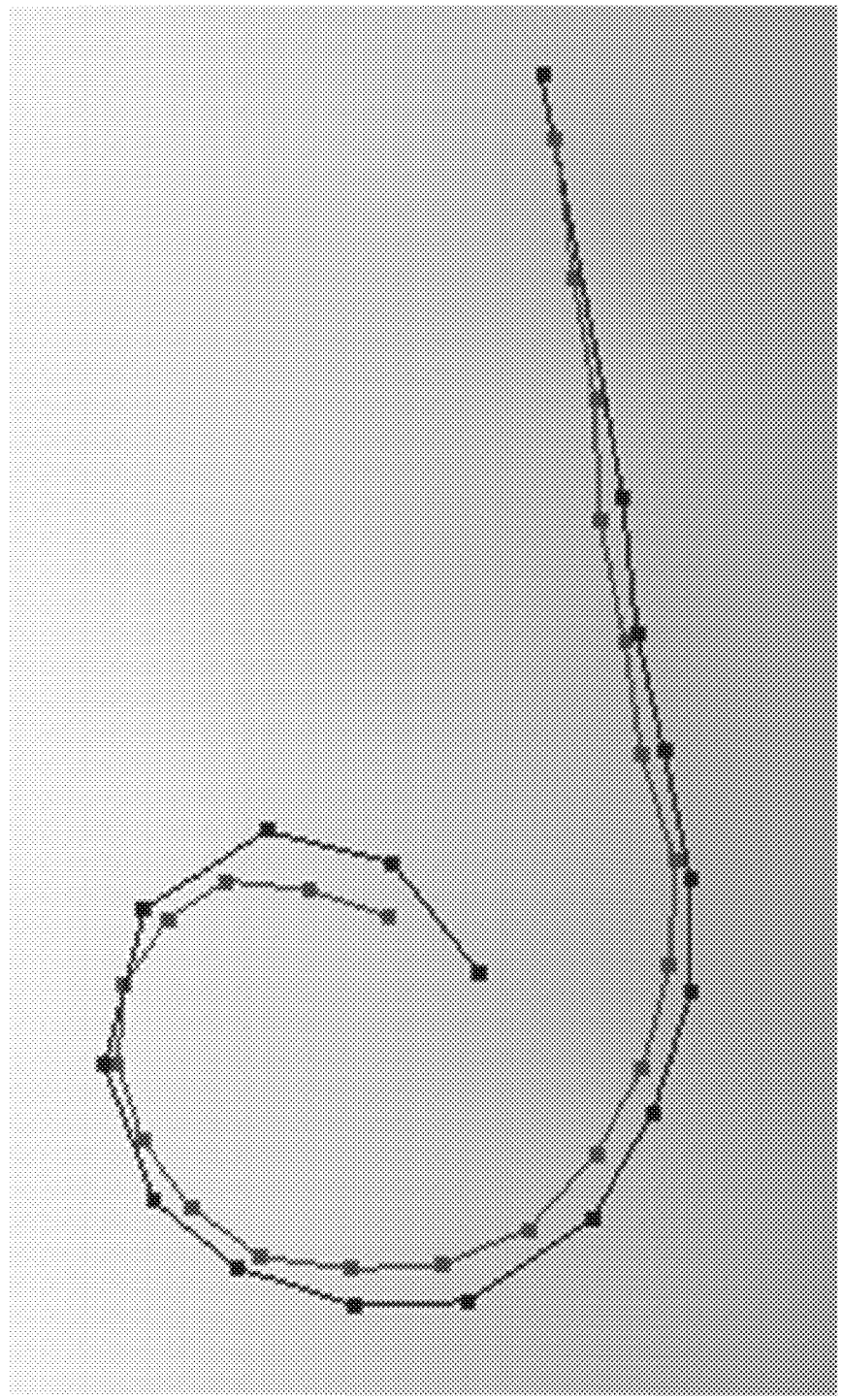
FIG. 25 shows resting state shapes of the MS (blue) and CA (red) arrays.

One limitation of our approach as it was initially implemented is that it references a surgically created space, the facial recess, whose shape cannot be precisely predicted from pre-operative CT scans. We used relatively coarse instructions (e.g., hug the posterior wall, the anterior wall, or remain in the mid region of the facial recess) but found that such instructions correlated with final electrode positioning as assessed by general linear modeling. To further explore this, in future work we will evaluate how well the surgically implemented vector agrees with the planned one using optically tracked insertion tools. Another limitation is the use of a single EA. In future studies, we plan to evaluate our techniques with additional EAs including the Contour Advance (CA) and 532 (Cochlear Corporation; Sydney, Australia). Towards this end, we have already created an array trajectory model for the CA similar to the one used in this study for the MS. In FIG. 25, we have registered the MS and CA models and found the resting-state shape of the two to be quite similar. We also have performed retrospective analysis the CA and MS EA's using post-operative CT scans of CI patients in our imaging database and have found positioning of the two arrays to be quite similar (MS: average insertion depth=393°, average modiolar distance=0.54 mm (N=17); CA: average insertion depth=377°, average modiolar distance=0.48 mm (N=79)). Thus, we anticipate that the methods we have evaluated in this study will lead to similar results with CA arrays. Yet another limitation is that our patient-customized, image-guided insertion plan is only applicable for *cochleae* free of anatomical malformations. And, while pre-curved arrays were the focus of this work, our techniques could also be applied to straight EAs with slightly different strategies necessary to recommend overall insertion depth and angle of insertion.

CONCLUSIONS

In this work, we have proposed and implemented a simple, image-guided approach for patient-customized CI electrode insertion. Preliminary results indicate that this method results in significantly higher rates of ST placement and better perimodiolar positioning of the middle section of the EA. We plan to confirm these exciting preliminary findings in a larger study and explore the potential impact on hearing outcomes.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

LIST OF REFERENCES

[1] National Institute on Deafness and Other Communication Disorders, "Cochlear Implants," No. 11-4798, 2014.

[2] Buss E, Pillsbury H C, Buchman C A, Pillsbury C H, Clark M S, Haynes D S, Labadie R F, Amberg S, Roland P S, Kruger P, Novak M A, Wirth J A, Black J M, Peters R, Lake J, Wackym P A, Firszt J B, Wilson B S, Lawson D T, Schatzer R, S. DHP, Barco A L: Multicenter U. S. Bilateral med-el cochlear implantation study: Speech perception over the first year of use. Ear Hear 2008; 29:20-32.

[3] Dorman M F, Yost W, Wilson B S, Gifford R H: Speech perception and sound localization by adults with bilateral cochlear implants. Seminars in Hearing 2009; 32:73-89.

[4] Gifford R H, Shallop J K, Peterson A M. (2008). Speech Recognition Materials and Ceiling Effects: Considerations for Cochlear Implant Programs. Audiol Neurotol, 13:193-205.

[5] Gifford R H, Dorman M F, Sheffield S W, Teece K, Olund A P. "Availability of binaural cues for bilateral cochlear implant recipients and bimodal listeners with and without hearing preservation." Audiol Neurotol. 2014; 19(1):57-71

[6] Litovsky R Y, Parkinson A, Arcaroli J, Sammeth C: Simultaneous bilateral cochlear implantation in adults: A multicenter clinical study. Ear Hear 2006; 27:714-730.

[7] Carlson M L, Driscoll C L, Gifford R H, Service G J, Tombers N M, Hughes-Borst B J, Neff B A, Beatty C W.

Implications of minimizing trauma during conventional cochlear implantation. Otol Neurotol. 32(6):962-8, 2011.

[8] Holden L K, Finley C C, Firszt J B, Holden T A, Brenner C, Potts L G, Gotter B D, Vanderhoof S S, Mispagel K, Heydebrand G, Skinner M W., "Factors affecting open-set word recognition in adults with cochlear implants," Ear Hear. 34(3):342-60, 2013.

[9] Wanna, G. B., Noble J. H., Carlson, M. L., Gifford, R. H., Dietrich, M. S., Haynes, D. S. Dawant, B. M., and Labadie, R. F., "Impact of Electrode Design and Surgical Approach on Scalar Location and Cochlear Implant Outcomes," Laryngoscope, vol. 124(S6), pp. S1-7, 2014.

[10] Wanna G B, Noble J H, Gifford R H, Dietrich M S, Sweeney A D, Zhang D, Dawant B M, Rivas A, Labadie R F. "Impact of Intrascalar Electrode Location, Electrode Type, and Angular Insertion Depth on Residual Hearing in Cochlear Implant Patients: Preliminary Results." Otol Neurotol. 36(8):1343-8, 2015.

[11] Noble, J. H., Labadie, R. F., Majdani, O and Dawant, B. M., "Automatic segmentation of intra-cochlear anatomy in conventional CT", IEEE Trans. Biomedical.Eng., vol. 58, no. 9, pp. 2625-2632, 2011.

[12] Noble, J. H., Gifford, R. H., Labadie, R. F., Dawant, B. M., 2012, "Statistical Shape Model Segmentation and Frequency Mapping of Cochlear Implant Stimulation Targets in C T," N. Ayache et al. (Eds.): MICCAI 2012, Part II, LNCS 7511, pp. 421-428. 2012.

[13] The Length of the Organ of *Corti* in Man, Hardy M, American Journal of Anatomy, 62(2), 1938, p. 179-311.

[14] Pelosi S and Noble J (co-first authors), Dawant B, and Labadie R F. "Analysis of inter-subject variations in promontory and intracochlear anatomy for cochlear implantation," Otology and Neurotology vol. 34(9), pp. 1675-1680, 2013.

[15] Zhao, Y., Dawant, B. M., Labadie, R. F., and Noble, J. H., "Automatic Localization of Cochlear Implant Electrodes in C T," Lecture Notes in Computer Science-Proceedings of MICCAI, vol. 8673, pp. 331-8, 2014.

[16] Noble, J. H. and Dawant, B. M., "Automatic graph-based localization of cochlear implant electrodes in C T," Lecture Notes in Computer Science-Proceedings of MICCAI, vol. 9350, pp. 152-9, 2015.

[17] Stakhovskaya O, Spridhar D, Bonham B H, Leake P A. Frequency Map for the Human Cochlear Spiral Ganglion: Implications for Cochlear Implants. Journ. Assoc. Res. Otol. 8, 2007.: 220-233.

[18] Rubenstein J. T., "How cochlear implants encode speech," Curr Opin Otolaryngol Head Neck Surg. 12(5): 444-8, 2004.

[19] Noble J H, Labadie R F, Gifford R H, Dawant B M, "Image-guidance enables new methods for customizing cochlear implant stimulation strategies," IEEE Trans Neural Syst Rehabil Eng. vol. 21(5):820-9, 2013.

[20] Noble J H, Gifford R H, Hedley-Williams A J, Dawant B M, and, Labadie R F, "Clinical evaluation of an image-guided cochlear implant programming strategy," Audiology & Neurotology, vol. 19, pp. 400-11, 2014.

[21] Noble J. H., Hedley-Williams A. J., Sunderhaus L. W., Dawant B. M., Labadie R. F., Gifford R. H., "Initial results with image-guided cochlear implant programming in children," in press in Otology & Neurotology, 2015.

[22] Skinner M W, Arndt P L, Staller S J. Nucleus 24 advanced encoder conversion study: performance versus preference. Ear Hear 2002. 23(1 Suppl):2S-17S.

[23] Yukawa K, Cohen L, Blamey P, Pyman B, Tungvachirakul V, O'Leary S. Effects of insertion depth of cochlear implant electrodes upon speech perception, Audiology and Neuro-Otology, 9(3), pp. 163-172, 2004.

[24] Verbist, B. M., Frijns, J. H. M., Geleijns, J., van Buchem, M. A., "Multisection C T as a Valuable Tool in the Postoperative Assessment of Cochlear Implant Patients," AJNR Am J Neuroradiol 26:424-429, February 2005.

[25] Aschendorff A, Kubalek R, Turowski B, Zanella F, Hochmuth A, Schumacher M, Klenzner T, Laszig R. Quality control after cochlear implant surgery by means of rotational tomography. Otol Neurotol. 2005; 26:34-37.

[26] Skinner M W, Holden T A, Whiting B R, Voie A H, Brundsen B, Neely G J, Saxon E A, Hullar T E, Finley C C: In vivo estimates of the position of advanced bionics electrode arrays in the human cochlea. Annals of Otology, Rhinology and Laryngology Supplement 2007; 197:2-24.

[27] T. F. Cootes, C. J. Taylor, D. H. Cooper, J. Graham, "Active Shape Models-Their Training and Application," Computer Vision and Image Understanding 61(1), pp. 38-59, 1995.

[28] Cakir A, Labadie R F, Dawant B M, Noble J H, "Utility of non-rigid cochlear models for evaluating intra-cochlear electrode position," under review at Otology & Neurotology (2016).

[29] Reda, F. A., McRackan T. R., Labadie, R. F., Dawant, B. M., Noble J H, "Automatic segmentation of intra-cochlear anatomy in post-implantation C T of unilateral cochlear implant recipients," Medical Image Analysis, vol. 18(3), pp. 605-15, 2014.

[30] Reda F A, Noble J H, Labadie R F, Dawant B M, "An artifact-robust technique for automatically segmenting the labyrinth in post-cochlear-implantation C T," Proceedings of the SPIE Conf. on Medical Imaging, 9034, 9034V, 2014.

[31] Finley C C, Holden T A, Holden L K, et al. "Role of electrode placement as a contributor to variability in cochlear implant outcomes," Otol Neurotol 29:920-928, 2008.

[32] Peterson G E, Lehiste I. (1962). Revised CNC lists for auditory tests. J Speech Hear Disord. 27:62-70.

[33] Wang, J., Dawant, B. M., Labadie, R. F., Noble, J. H., "Retrospective Evaluation of a Technique for Patient-Customized Placement of Precurved Cochlear Implant Electrode Arrays," Otolaryngology—Head and Neck Surgery, epub ahead of print, 2017.

[34] W. H. Press, B. P. Flannery, S. A. Teukolsky, and W. T. Vetterling, Numerical Recipes in C, 2nd ed. Cambridge, U. K.: Cambridge Univ. Press, 1992, ch. 10, pp. 412-419.

[35] Goshtasgy, A. "Registration of images with geometric distortions", IEEE Transactions on Geoscience and Remote Sensing, 26(1), pp. 60-64, 1988.

[36] Bench J., Kowal A., Bamford J., "The BKB (Bamford-Kowal-Bench) sentences lists for partially-hearing children," Br. J. Audiol. 13: 108-12, 1979.

[37] Besl P. J. and McKay N. D., "A method for registration of 3-D shapes," IEEE Trans. on Patt. Anal. Mach. Intel., vol. 14(2), pp. 239-56, 1992.

[38] Schonemann, P. H., "A generalized solution of the orthogonal Procrustes problem," Psychometrika, vol. 31, pp. 1-10, 1966.

[39] McBrayer K., Wanna G. B., Labadie R. F., Dawant B. M., Noble J. H., "Analysis of patient-specific variability in optimal cochlear implant insertion depths," Oral presentation at the American Neurotology Society, 2015.

[40] Noble, J. H., F. M. Warren, R. F. Labadie, and B. M. Dawant. "Automatic Segmentation of the Facial Nerve and Chorda Tympani in Ct Images Using Spatially Dependent Feature Values." Med Phys 35, no. 12 (December 2008): 5375-84, PMC3208411

[41] Noble, J. H., Dawant, B. M., Warren, F. M., Labadie, R. F., 2009, "Automatic Identification and 3D Rendering of Temporal Bone Anatomy," Otol Neurotol., 30(4):436-42. PMCID 19339909

[42] Noble, J. H., Majdani, O., Labadie, R. F., Dawant, B. M., Fitzpatrick, J. M., "Automatic Determination of Optimal Linear Drilling Trajectories for Cochlear Access Accounting for Drill-Positioning Error," Intl. J. of Med. Robotics and Comp. Assist. Surg., 6(3):281-290, 2010.

[43] Noble J H, Labadie R F, Wanna G B, Dawant B M, "Image guidance could aid performance of atraumatic cochlear implantation surgical techniques," Proc. of the SPIE conf. on Medical Imaging, 8671, 86711T, 2013.

[44] Labadie R F, Chodhury P, Cetinkaya E, Balachandran R, Haynes D S, Fenlon M, Jusczyzck A S, Fitzpatrick J M, "Minimally Invasive, Image-Guided, Facial-Recess Approach to the Middle Ear: Demonstration of the Concept of Percutaneous Cochlear Access In Vitro," Otology & Neurotology 26(4), pp 557-562, 2005.

[45] Lahiri U, Labadie R F, Changchun Liu, Balachandran R, Majdani O, Sarkar N, "A step toward identification of surgical actions in mastoidectomy," IEEE Trans. On Biom. Eng. 57(2), pp. 479-87, 2010.

[46] Danilchenko A, Balachandran R, Toennies J L, Baron S, Munske B, Fitzpatrick J M, Withrow, T J, Webster R J III, Labadie R F, "Robotic Mastoidectomy," Otology & Neurotology 32(1)-pp 11-16, 2011.

[47] Alexiades, G, Dhanasingh, A, Jolly, C, "Method to Estimate the Complete and Two-Turn Cochlear Duct Length," Otology & Neurotology 36(5), p 904-907, 2015.

[48] Riva A., Cakir A. (co-first authors), Hunter J., Labadie R. F., Zuniga G. M., Wanna G. B., Dawant B. M., Noble J. H., "Automatic cochlear duct length estimation for selection of cochlear implant electrode arrays," under review at Otology & Neurotology (2016).

[49] McBrayer K. L., Wanna G. B, Dawant B. M., Balachandran R., Labadie R. F., and Noble J. H., "Resection Planning for Robotic Acoustic Neuroma Surgery," Journal of Medical Imaging, 2017(in press).

[50] Maurer C R Jr, Fitzpatrick J M, Wang M Y, Galloway R L Jr, Maciunas R J, Allen G S. Registration of head volume images using implantable fiducial markers. IEEE Trans Med Imaging. 1997; 16(4):447-462.

[51] Maurer C R Jr, Maciunas R J, Fitzpatrick J M. Registration of head C T images to physical space using a weighted combination of points and surfaces. IEEE Trans Med Imaging. 1998; 17(5):753-761.

[52] Kumar A N, Miga M I, Pheiffer T S, Chambless L B, Thompson R C, Dawant B M. "Persistent and automatic intraoperative 3D digitization of surfaces under dynamic magnifications of an operating microscope," Med Image Anal. 19(1):30-45, 2015.

[53] Wardrop P, Whinney D, Rebscher S J, Roland J T Jr, Luxford W, Leake P A, "A temporal bone study of insertion trauma and intracochlear position of cochlear implant electrodes. I: Comparison of Nucleus banded and Nucleus Contour electrodes," Hear Res. vol. 203(1-2), pp. 54-67, 2005.

[54] Schipper J, Klenzner T, Aschendorff A, Arapakis I, Ridder G J. Navigiert-kontrollierte Kochleostomie. Ist eine Verbesserung der Ergebnisqualitat in der Kochleaimplantatchirurgie möglich? [Navigation-controlled cochleostomy. Is an improvement in the quality of results for cochlear implant surgery possible?] HNO. 2004; 52(4): 329-335.

[55] Kratchman L, Schurzig D, McRackan T, Balachandran R, Noble J, Webster R, Labadie R, "A Manually-Operated, Advance Off-Stylet Insertion Tool for Minimally-Invasive Cochlear Implantation Surgery," IEEE Trans on Biomed Eng. Vol. 59(10), 2792-800, 2012.

[56] Spahr A J, Dorman M F, Litvak L M, Van Wie S, Gifford R H, Loizou P C, Loiselle L M, Oakes T, Cook S., "Development and validation of the AzBio sentence lists", Ear & Hearing 33(1):112-7, 2012.

[57] Zuniga M G, Rivas A, Hedley-Williams A J, Gifford R H, Dwyer R, Dawant B M, Wanna G B, Noble J H Labadie R F, "Tip fold-over in cochlear implantation: case series," Otology & Neurotology, vol. 38(2), pp. 199-206, 2017.

[58] Kesler K, Dillon N P, Fichera L, Labadie R F, "Human Kinematics of Cochlear Implant Surgery: An Investigation of Insertion Micro-Motions and Speed Limitations," Otolaryngol Head Neck Surg. 2017 (in press)

[59] Mendel L L, Mustain W D, Magro J, "Normative Data for the Maryland CNC Test," Journ. Of Am. Acad. Audiol., vol. 25, pp. 775-781, 2014.

[60] Kochkin S, "The efficacy of hearing aids in achieving compensation equity in the workplace," The Hearing Journal, vol. 63 (10), pp. 19-28, 2010.

What is claimed is:

1. A method for designing a patient-customized electrode array (EA) or selecting an existing EA that fits the patient best, comprising:
  acquiring information of the patient-specific cochlear size and/or shape of the cochlea; and
  designing a patient-customized electrode array (EA) or selecting an existing EA that fits the patient best based on the acquired information of the patient-specific cochlear size and/or shape of the cochlea,
  wherein the acquiring step comprises:
  segmenting shapes of structures of interest (SOIs) of a cochlea of the patient in a pre-operative computed tomography (CT) image of the cochlea using a shape model, wherein the EA is to be placed in the cochlea;
  defining a three dimensional (3D) curve of interest within the shape model of the SOIs as a sequence of points, $\{P_i\}$, wherein i=1, 2, 3, ... N, N is an integer greater than zero;
  automatically transforming the defined 3D curve to the pre-operative CT image so as to obtain a structure curve in the cochlea; and
  determining a length and curvatures of the structure curve at the sequence of points $\{P_i\}$.

2. The method of claim 1, wherein the selecting/designing step comprises:
  designing a patient-customized electrode array (EA) or selecting an existing EA that fits the patient best based on the determined length and curvatures of the structure curve in cochlea such that after the EA shape model, which estimates the resting state shape of the EA, is rigidly registered to the structure curve in the cochlea, the EA shape model has a registration error smaller than a preset value.

3. The method of claim 1, wherein the SOIs are temporal bone anatomy.

4. The method of claim 1, wherein the structure curve is a modiolar curve or a lateral wall curve in the cochlea.

5. The method of claim 4, wherein the straight EA has a length determined such that when placed along the lateral wall curve, an angular insertion depth of the distal electrode reaches about 500°, while a proximal electrode falls safely within the cochlea being greater than 30°.

6. The method of claim 1, wherein the EA comprises a plurality of electrodes, $\{E_i\}$, wherein the i-th electrode $E_i$ is to be placed in a location corresponding to the i-th point $P_i$ of the structure curve in the cochlea, wherein i=1, 2, 3, . . . N, N is an integer greater than zero.

7. The method of claim 1, wherein the shape model is a non-rigid statistical shape model created with μCT images of a plurality of cochlea specimens in which intra-cochlear structures are visible.

8. The method of claim 1, wherein the defined 3D structure curve is automatically transformed to the pre-operative CT image using a thin plate spline registration.

9. The method of claim 1, wherein the EA shape model is rigidly registered to the structure curve in the cochlea using an iterative closest point registration, thereby placing the resting state shape of the EA within the SOIs in the cochlea such that the EA matches the structure curve in the cochlea.

10. The method of claim 1, further comprising determining a patient-customized insertion plan for electrode insertion using the registered EA shape model, wherein the patient-customized insertion plan comprises at least a recommended depth.

11. The method of claim 10, wherein when inserted, the base depth of electrode insertion of the EA matches the recommended depth.

12. The method of claim 1, wherein the segmenting step comprises automatically fitting the shape model to an external boundary of the cochlea that is visible in the pre-operative CT, thereby allowing highly accurate estimation of positions and shapes of intra-cochlear structures of the cochlea that are not visible in the pre-operative CT.

13. The method of claim 1, wherein the curvature of the EA at the i-th electrode $E_i$ is characterized with a curvature $R_i$ that matches the curvature of the i-th point Pi of the structure curve in the cochlea.

14. The method of claim 13, wherein the i-th electrode $E_i$ is a flat electrode, or a curved electrode that is characterized with a curvature that matches the curvature of the i-th point $P_i$ of the structure curve in the cochlea.

* * * * *